US008846700B2

(12) United States Patent
Iino et al.

(10) Patent No.: US 8,846,700 B2
(45) Date of Patent: *Sep. 30, 2014

(54) HETEROARYL QUINAZOLINE DERIVATIVES

(71) Applicant: MSD K.K., Chiyoda-Ku (JP)

(72) Inventors: Tomoharu Iino, Koto-ku (JP); Akio Ohno, Machida (JP); Norikazu Otake, Tsukuba (JP); Takuya Suga, Tsukuba (JP); Masanori Asai, Tsukuba (JP)

(73) Assignee: MSD K.K., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,639

(22) Filed: Sep. 9, 2013

(65) Prior Publication Data

US 2014/0011801 A1    Jan. 9, 2014

Related U.S. Application Data

(63) Continuation of application No. 13/539,878, filed on Jul. 2, 2012, now abandoned, which is a continuation of application No. 12/742,113, filed as application No. PCT/JP2008/070396 on Nov. 10, 2008, now Pat. No. 8,232,284.

(30) Foreign Application Priority Data

Nov. 12, 2007   (JP) ................. 2007-293256

(51) Int. Cl.
*A61K 31/517*   (2006.01)

(52) U.S. Cl.
USPC ...................... 514/266.2; 544/284

(58) Field of Classification Search
CPC .................................... C07D 401/14
USPC ......................................... 544/284
See application file for complete search history.

(56) References Cited

U.S. PATENT DOCUMENTS

| 7,687,502 | B2 | 3/2010 | Mitsuya et al. |
| 2006/0167053 | A1 | 7/2006 | Iino et al. |
| 2006/0258701 | A1 | 11/2006 | Mitsuya et al. |
| 2008/0070928 | A1 | 3/2008 | Nonoshita et al. |
| 2008/0090799 | A1 | 4/2008 | Hashimoto et al. |
| 2008/0125429 | A1 | 5/2008 | Hashimoto et al. |
| 2009/0018056 | A1 | 1/2009 | Iino et al. |
| 2009/0118304 | A1 | 5/2009 | Takahashi et al. |
| 2010/0041660 | A1 | 2/2010 | Mitsuya et al. |

FOREIGN PATENT DOCUMENTS

| WO | 2005/090332 | 9/2005 |
| WO | 2010/107610 | 9/2010 |

OTHER PUBLICATIONS

Garfinkel et al., "Computer modeling identifies glucokinase as glucose sensor of pancreatic beta cells", Am. J. Physiol. (1984), vol. 247, pp. R527-R536.
Vionnet et al., "Nonsense mutation in the glucokinase gene causes early-onset non-insulin-dependent diabetes mellitus", Nature (1992), vol. 356, pp. 721-722.
Glaser et al., "Familial hyperinsulinism caused by an activating glucokinase mutation", New England J. of Medicine (1998), vol. 338, pp. 226-230.
Ferre et al., "Correction of diabetic alterations by glucokinase", PNAS (1996), vol. 93, pp. 7225-7230.
Grupe et al., "Transgenic knockouts reveal a critical requirement for pancreatic beta cell glucokinase . . . ", Cell (1995), vol. 83, pp. 69-78.
Green, Protective Groups in Organic Synthesis, 2nd ed., John Wiley & Sons (1991).
Mitsunobu, "The use of diethyl azodicarboxylate and triphenylphosphine . . . ", Synthesis (1981), vol. 1, pp. 1-28.
Int'l Search Report of PCT/JP2008/070396, dated Nov. 26, 2008.

*Primary Examiner* — Brian McDowell
(74) *Attorney, Agent, or Firm* — Anna L. Cocuzzo; Catherine D. Fitch

(57) ABSTRACT

Disclosed are compounds of the following formula and their pharmaceutically-acceptable salts, which have an effect of glucokinase activation and are useful in the field of medicines for treatment for diabetes, obesity, etc.

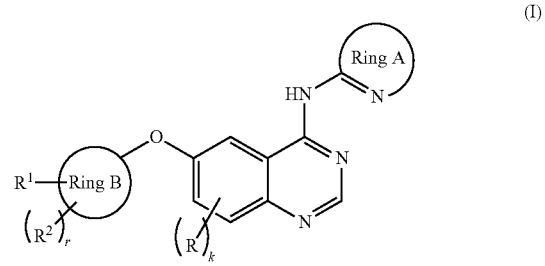

(I)

(wherein ring A represents a pyrazolyl group optionally having a lower alkyl group, etc.; ring B represents a heteroaryl group; R represents a lower alkyl group, etc.; $R^1$ represents a group of a formula:

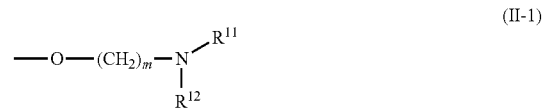

(II-1)

(wherein $R^{11}$ and $R^{12}$ each independently represent a hydrogen atom, etc.; m indicates an integer of from 2 to 6, etc.; $R^2$ represents a lower alkyl group, etc.; r indicates an integer of from 0 to 3; k indicates an integer of from 0 to 4).

16 Claims, No Drawings

HETEROARYL QUINAZOLINE DERIVATIVES

CROSS-REFERENCE TO RELATED APPLICATIONS

This application is a continuation of U.S. application Ser. No. 13/539,878, filed Jul. 2, 2012, pending, which is a continuation of U.S. application Ser. No. 12/742,113, now U.S. Pat. No. 8,232,284, which is a U.S. National Phase application under 35 U.S.C. §371 of PCT Application No. PCT/JP2008/070396, filed Nov. 10, 2008, which published as WO 2009/063821 on May 22, 2009, and claims priority under 35 U.S.C. §365(b) from Japanese Patent Application No. JP 2007-293256, filed Nov. 12, 2007, now abandoned.

FIELD OF THE INVENTION

The present invention relates to glucokinase activators containing heteroaryloxy quinazoline derivatives as active ingredients. The present invention further relates to novel heteroaryloxy quinazoline derivatives.

BACKGROUND OF THE INVENTION

Glucokinase (GK) (ATP: D-hexose 6-phosphotransferase, EC 2.7.1.1) is one of four mammalian hexokinases (hexokinase IV). Hexokinases are enzymes in the first step of the glycolytic pathway and catalyze the reaction from glucose to glucose-6-phosphate. Glucokinase is expressed principally in the liver and pancreatic beta cells and plays an important role in whole-body glucose metabolism by controlling the rate-determining step in glucose metabolism in these cells. The glucokinases expressed in the liver and pancreatic beta cells differ in the sequence of the 15 N-terminal amino acids due to a difference in splicing, respectively, whereas their enzymatic characteristics are identical. The enzyme activities of the three hexokinases (I, II, and III) other than the glucokinase become saturated at a glucose concentration of 1 mM or lower, whereas the Km of glucokinase to glucose is 8 mM, which is close to the physiological blood glucose level. Accordingly, glucokinase-mediated intracellular glucose metabolism is accelerated in response to blood glucose level changes by postprandial glucose level increase (10-15 mM) from normal glucose (5 mM).

It has been hypothesized for around 10 years that glucokinase serves as a glucose sensor for pancreatic beta cells and the liver (for example, see non-patent document 1). Recent results in glucokinase gene-manipulated mice have confirmed that glucokinase does in fact play an important role in systemic glucose homeostasis. Mice lacking a functional glucokinase gene die shortly after birth (for example, see non-patent document 2), while healthy and diabetic mice overexpressing glucokinase have lower blood glucose levels (for example, see non-patent document 3). With glucose level increase, the reactions of pancreatic beta- and liver cells, while differing, both act toward lowering blood glucose. Pancreatic beta cells secrete more insulin, while the liver takes up glucose and stores it as glycogen while also reducing glucose release.

Such variation in glucokinase enzyme activity is important for liver and pancreatic beta cell-mediated glucose homeostasis in mammals. A glucokinase gene mutation has been found in a case of diabetes which occurs in youth, referred to as MODY2 (maturity-onset diabetes of the young), and the reduced glucokinase activity has been shown to be responsible for blood glucose increase (for example, see non-patent document 4). In contrast, families having a mutation increasing the glucokinase activity has been found, and such individuals exhibit hypoglycemia (for example, see non-patent document 5).

These suggest that in humans as well, glucokinase functions as a glucose sensor and thus plays an important role in glucose homeostasis. Glucose regulation utilizing a glucokinase sensor system is likely to be possible to achieve in most patients with type II diabetes mellitus. Since glucokinase activators should have effects of accelerating insulin secretion by pancreatic beta cells and of promoting glucose uptake and inhibiting glucose release by the liver, they are likely to be useful as therapeutic agents for patients with type II diabetes mellitus.

In recent years, it has been found that pancreatic beta cell glucokinase is expressed locally in rat brain, particularly in the ventromedial hypothalamus (VMH). Around 20% of VMH neurons are referred to as "glucose-responsive neurons", and these have long been considered to play an important role in body weight control. Administration of glucose into rat brain reduces feeding consumption, whereas inhibition of glucose metabolism by intracerebral administration of glucose analog glucosamine produces hyperphagia. Electrophysiological experiments have indicated that glucose-responsive neurons are activated in response to physiological glucose level changes (5-20 mM) but that their activation is inhibited with glucose metabolism inhibition by, e.g., glucosamine. The glucose level-detecting system in the VMH is intended to be based on a glucokinase-mediated mechanism similar to that for insulin secretion by pancreatic beta cells. Accordingly, substances which activate glucokinase in the VMH in addition to the liver and pancreatic beta cells not only exhibit a glucose rectifying effect but can also potentially rectify obesity, which is a problem for most patients with type II diabetes mellitus.

The above description indicates that compounds having glucokinase-activating effects are useful as therapeutic and/or prophylactic agents for diabetes mellitus, as therapeutic and/or prophylactic agents for chronic complications of diabetes mellitus, such as retinopathy, nephropathy, neurosis, ischemic heart disease and arteriosclerosis, and further as therapeutic and/or prophylactic agents for obesity.

As a compound associated with a heteroaryloxy quinazoline derivative according to the present invention, for example, a compound represented by the following formula (A):

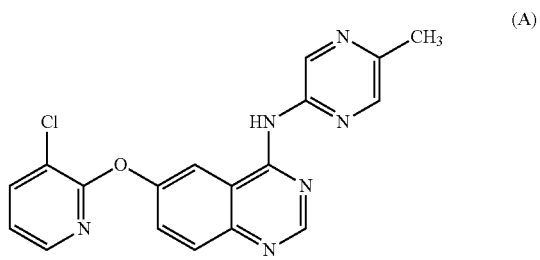 [SMILES: Cc1cnc(Nc2ncnc3ccc(Oc4ncccc4Cl)cc23)cn1]

is disclosed in patent document 1.

Although there is a commonality of having GK activity between the compound represented by the formula (A) and a compound according to the present invention, the compound represented by the formula (A) has no dimethylaminoethoxy group as an essential substituent on a pyridine ring.

patent document 1: WO2005/090332 non-patent document 1: Garfinkel D. et al., Computer modeling identifies glucokinase as glucose sensor of pancreatic beta-cells, American Journal Physiology, vol. 247 (3Pt2) 1984, pp. 527-536 non-patent document 2: Grupe A. et al., Transgenic knockouts reveal a critical requirement for pancreatic beta cell glucokinase in maintaining glucose homeostasis, Cell, vol. 83, 1995, pp. 69-78 non-patent document 3: Ferre T. et al., Correction of diabetic alterations by glucokinase, Proceedings of the National Academy of Sciences of the U.S.A, vol. 93, 1996, pp. 7225-7230 non-patent document 4: Vionnet N. et al., Nonsense mutation in the glucokinase gene causes early-onset non-insulin-dependent diabetes mellitus, Nature Genetics, vol. 356, 1992, pp. 721-722 non-patent document 5: Glaser B. et al., Familial hyperinsulinism caused by an activating glucokinase mutation, New England Journal Medicine, vol. 338, 1998, pp. 226-230

SUMMARY OF THE INVENTION

It is desirable to provide therapeutic and/or prophylactic agents for diabetes mellitus that bind to glucokinase to increase glucokinase activity; and to provide anti-obesity agents that stimulate and act on satiety center by activating glucokinase. The present invention also provides compounds having drug efficacy and/or more excellent properties as medicaments. Further provided are glucokinase activators comprising compounds according to the present invention or pharmaceutically acceptable salts thereof as active ingredients. Also provided are treatments and/or therapeutic agents for diabetes mellitus comprising compounds according to the present invention or pharmaceutically acceptable salts thereof as active ingredients. Also provided are pharmaceutical compositions comprising compounds according to the present invention or pharmaceutically acceptable salts thereof as active ingredients. In addition, the present invention also provides pharmaceutical compositions comprising: compounds according to the present invention used for treating, preventing and/or delaying onset of type 2 diabetes mellitus; other drugs; and pharmaceutically acceptable carriers.

The present inventors undertook thorough research to find that introduction of a dimethylaminoethoxy group or the like as a substituent on a quinazoline ring into quinazoline compounds having GK activation action in related art results in great improvement in drug efficacy and/or properties such as solubility compared to quinazoline compounds in related art, and the invention was thus accomplished.

Specifically, the present invention relates to:
(1) a compound represented by a formula (I):

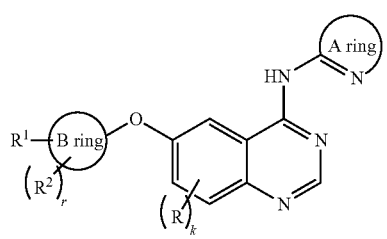

[wherein the A ring represents a 5- or 6-membered heteroaryl ring that is selected from the group consisting of pyrazolyl, pyrazinyl, thiadiazolyl, thiazolyl, pyridinyl, thiatriazolyl, triazolyl, tetrazolyl, imidazolyl, pyrimidinyl, pyridazinyl, triazinyl, oxazolyl, oxadiazolyl and isoxazolyl groups, which may have one or two groups selected from the group consisting of lower alkyl, lower alkoxy, halogen, hydroxy, $C_{3-7}$ cycloalkyl and lower alkyl having 1-3 identical or different lower alkoxy groups, halogen atoms or hydroxy groups, or represents a ring in which the 5- or 6-membered heteroaryl ring and a benzene or pyridine ring are condensed;

the B ring represents a 5- or 6-membered heteroaryl group having 1-3 identical or different hetero atoms selected from the group consisting of nitrogen, sulfur and oxygen atoms;

R represents a group selected from the group consisting of lower alkyl, lower alkoxy, halogen, hydroxy and lower alkyl having 1-3 identical or different lower alkoxy groups, halogen atoms or hydroxy groups;

k represents an integer of from 0 to 4;

$R^1$ denotes a group represented by a formula (II-1)

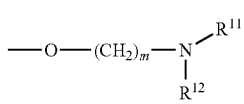

(wherein $R^{11}$ and $R^{12}$ each independently represent hydrogen, lower alkyl or $C_{3-7}$ cycloalkyl, or $R^{11}$ and $R^{12}$, together with the nitrogen atom to which they are bound, constitute 4- to 7-membered nitrogen-containing aliphatic rings (which may be substituted with 1-3 identical or different halogen atoms), or any carbon atom of $(CH_2)_m$, together with $R^{11}$ or $R^{12}$, may constitute 4- to 7-membered nitrogen-containing aliphatic rings;

any carbon atom in $(CH_2)_m$ may be substituted with a lower alkyl group;

the nitrogen atom to which $R^{11}$ and $R^{12}$ are bound may form N-oxide; and m represents an integer of from 2 to 6), a group represented by a formula (II-2)

(wherein $R^{13}$ represents lower alkoxy, hydroxy or carboxyl;

n represents an integer of from 1 to 6;

upon $R^{13}$ being lower alkoxy, the lower alkoxy, together with any carbon atom of $(CH_2)_n$, may form 5- to 7-membered aliphatic rings; and any carbon atom in $(CH_2)_n$ may be substituted with a lower alkyl group), a group represented by a formula (II-3)

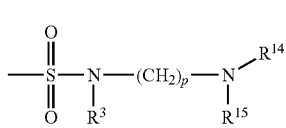

(wherein $R^{14}$ and $R^{15}$ are synonymous with the above $R^{11}$ and $R^{12}$;

p represents an integer of from 2 to 6; and
R³ represents a hydrogen atom or a lower alkyl group), or
a group represented by a formula (II-4)

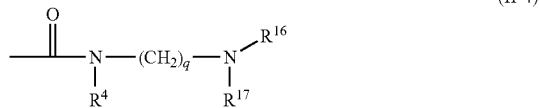
(II-4)

(wherein R¹⁶ and R¹⁷ are synonymous with the above R¹¹ and R¹²;
q represents an integer of from 2 to 6; and
R⁴ represents a hydrogen atom or a lower alkyl group),
and the substituent which the B ring has;
R² is a group selected from the group consisting of lower alkyl, lower alkoxy, halogen, hydroxy, cyano, carboxyl, alkoxycarbonyl, N-alkylcarbamoyl, N,N-dialkylcarbamoyl, lower alkylsulfonyl and lower alkyl having 1-3 identical or different lower alkoxy groups, halogen atoms, hydroxy groups, cyano groups, carboxyl groups, alkoxycarbonyl groups, N-alkylcarbamoyl groups, N,N-dialkylcarbamoyl groups or lower alkylsulfonyl groups, and the substituent which the B ring may have; and
r represents an integer of from 0 to 3] or a pharmaceutically acceptable salt thereof;

(2) the compound according to the above (1), wherein the B ring is a group selected from the group consisting of pyridinyl, pyrazinyl, pyrimidinyl, pyridazinyl, thiazolyl, thiadiazolyl, imidazolyl and isoxazolyl groups, or a pharmaceutically acceptable salt thereof;

(3) the compound according to the above (1), wherein the A ring is a 5- or 6-membered heteroaryl group that is selected from the group consisting of pyrazolyl, pyrazinyl, thiadiazolyl, pyridinyl, triazolyl and isoxazolyl groups, which may have one or two groups selected from the group consisting of lower alkyl, lower alkoxy, halogen, hydroxy, $C_{3-7}$ cycloalkyl and lower alkyl having 1-3 identical or different lower alkoxy groups, halogen atoms or hydroxy groups; and the B ring is a group selected from the group consisting of pyridinyl and pyrimidinyl groups,
or a pharmaceutically acceptable salt thereof;

(4) the compound according to any one of the above (1) to (3), wherein R¹ is a group represented by the formula (II-1) or (II-2), or a pharmaceutically acceptable salt thereof;

(5) the compound according to any one of the above (1) to (3), wherein R¹ is a group represented by the formula (II-1), or a pharmaceutically acceptable salt thereof;

(6) the compound according to any one of the above (1) to (3), wherein R¹ is a group represented by the formula (II-2), or a pharmaceutically acceptable salt thereof;

(7) the compound according to any one of the above (1) to (3), wherein R¹ is a group represented by the formula (II-3), or a pharmaceutically acceptable salt thereof;

(8) the compound according to any one of the above (1) to (3), wherein R¹ is a group represented by the formula (II-4), or a pharmaceutically acceptable salt thereof;

(9) the compound according to the above (5), wherein one of R¹¹ and R¹² is a hydrogen atom; and the other is a lower alkyl or $C_{3-7}$ cycloalkyl group, or a pharmaceutically acceptable salt thereof;

(10) the compound according to the above (5), wherein R¹¹ and R¹² each independently are lower alkyl or $C_{3-7}$ cycloalkyl groups, or a pharmaceutically acceptable salt thereof;

(11) the compound according to the above (5), wherein R¹¹ and R¹² represent 4- to 7-membered nitrogen-containing aliphatic rings constituted by R¹¹ and R¹² together with the nitrogen atom to which they are bound, (the nitrogen atom to which R¹¹ and R¹² are bound may form N-oxide; and the 4- to 7-membered nitrogen-containing aliphatic rings may be substituted with 1-3 identical or different halogen atoms), or a pharmaceutically acceptable salt thereof;

(12) the compound according to the above (5), wherein R¹¹ and R¹² represent a 4- to 7-membered nitrogen-containing aliphatic rings formed by either R¹¹ or R¹² together with any carbon atom of $(CH_2)_m$, (any carbon atom in $(CH_2)_m$ may be substituted with a lower alkyl group), or a pharmaceutically acceptable salt thereof;

(13) the compound according to the above (1), wherein the compound represented by the formula (I) is
6-({3-chloro-5-[2-(dimethylamino)ethoxy]pyridin-2-yl}oxy)-N-(1-methyl-1H-pyrazol-3-yl)quinazolin-4-amine,
6-({2-chloro-5-[2-(dimethylamino)ethoxy]pyridin-3-yl}oxy)-N-(1-methyl-1H-pyrazol-3-yl)quinazolin-4-amine,
6-({6-[2-(dimethylamino)ethoxy]pyridin-3-yl}oxy)-N-(1-methyl-1H-pyrazol-3-yl)quinazolin-4-amine,
6-({5-[3-(dimethylamino)propoxy]pyridin-2-yl}oxy)-N-(1-methyl-1H-pyrazol-3-yl)quinazolin-4-amine,
6-({5-[2-(isopropylamino)ethoxy]pyridin-2-yl}oxy)-N-(1-methyl-1H-pyrazol-3-yl)quinazolin-4-amine,
6-({5-[(1-methylazetidin-3-yl)oxy]pyridin-2-yl}oxy)-N-(1-methyl-1H-pyrazol-3-yl)quinazolin-4-amine,
6-({2-[2-(dimethylamino)ethoxy]pyrimidin-5-yl}oxy)-N-(1-methyl-1H-pyrazol-3-yl)quinazolin-4-amine,
6-({5-[2-(dimethylamino)ethoxy]pyrimidin-2-yl}oxy)-N-(1-methyl-1H-pyrazol-3-yl)quinazolin-4-amine,
N-(1-methyl-1H-pyrazol-3-yl)-6-{[5-(2-piperidin-1-yl)ethoxy)pyridin-2-yl]oxy}quinazolin-4-amine,
6-[(5-{2-[ethyl(methyl)amino]ethoxy}pyridin-2-yl)oxy]-N-(1-methyl-1H-pyrazol-3-yl)quinazolin-4-amine hydrochloride,
6-({5-[2-(diethylamino)ethoxy]pyridin-2-yl}oxy)-N-(1-methyl-1H-pyrazol-3-yl)quinazolin-4-amine hydrochloride,
6-[(5-{2-[(3R)-3-fluoropyrrolidin-1-yl]ethoxy}pyridin-2-yl)oxy]-N-(1-methyl-1H-pyrazol-3-yl)quinazolin-4-amine hydrochloride,
6-[(5-{2-[(3S)-3-fluoropyrrolidin-1-yl]ethoxy}pyridin-2-yl)oxy]-N-(1-methyl-1H-pyrazol-3-yl)quinazolin-4-amine hydrochloride,
N-(1-methyl-1H-pyrazol-3-yl)-6-[(5-{2-[(2R)-2-methylpyrrolidin-1-yl]ethoxy}pyridin-2-yl)oxy]quinazolin-4-amine hydrochloride,
N-(1-methyl-1H-pyrazol-3-yl)-6-[(5-{2-[(2S)-2-methylpyrrolidin-1-yl]ethoxy}pyridin-2-yl)oxy]quinazolin-4-amine hydrochloride,
6-({5-[2-(cyclobutylamino)ethoxy]pyridin-2-yl}oxy)-N-(1-methyl-1H-pyrazol-3-yl)quinazolin-4-amine hydrochloride,
6-({5-[2-(cyclopentylamino)ethoxy]pyridin-2-yl}oxy)-N-(1-methyl-1H-pyrazol-3-yl)quinazolin-4-amine hydrochloride,
6-({3-chloro-5-[2-(ethylamino)ethoxy]pyridin-2-yl}oxy)-N-(1-methyl-1H-pyrazol-3-yl)quinazolin-4-amine hydrochloride,
6-({5-[2-(ethylamino)ethoxy]-3-fluoropyridin-2-yl}oxy)-N-(1-methyl-1H-pyrazol-3-yl)quinazolin-4-amine hydrochloride, 6-({3-chloro-5-[3-(ethylamino)propoxy]pyridin-2-yl}oxy)-N-(1-methyl-1H-pyrazol-3-yl)quinazolin-4-amine hydrochloride,
6-({3-chloro-5-[3-(isopropylamino)propoxy]pyridin-2-yl}oxy)-N-(1-methyl-1H-pyrazol-3-yl)quinazolin-4-amine hydrochloride,
6-({3-chloro-5-[3-(methylamino)propoxy]pyridin-2-yl}oxy)-N-(1-methyl-1H-pyrazol-3-yl)quinazolin-4-amine hydrochloride,
6-{[5-(azetidin-3-yloxy)-3-chloropyridin-2-yl]oxy}-N-(1-methyl-1H-pyrazol-3-yl)quinazolin-4-amine hydrochloride,
6-({5-[(1-isopropylazetidine-3-yl)oxy]pyridin-2-yl}oxy)-N-(1-methyl-1H-pyrazol-3-yl)quinazolin-4-amine hydrochloride,
6-({5-[(1-ethylazetidin-3-yl)oxy]-3-fluoropyridin-2-yl}oxy)-N-(1-methyl-1H-pyrazol-3-yl)quinazolin-4-amine hydrochloride,
6-[(5-{[(2S)-2-(methylamino)propyl]oxy}pyridin-2-yl)oxy]-N-(1-methyl-1H-pyrazol-3-yl)quinazolin-4-amine,
6-[(5-{[(2R)-2-(methylamino)propyl]oxy}pyridin-2-yl)oxy]-N-(1-methyl-1H-pyrazol-3-yl)quinazolin-4-amine,
6-({5-[(1-methylazetidin-3-yl)methoxy]pyridin-2-yl}oxy)-N-(1-methyl-1H-pyrazol-3-yl)quinazolin-4-amine hydrochloride,
N-(1-methyl-1H-pyrazol-3-yl)-6-{[5-(2-pyrrolidin-2-ylethoxy)pyridin-2-yl]oxy}quinazolin-4-amine,
N-(1-methyl-1H-pyrazol-3-yl)-6-({5-[2-(1-methylpyrrolidin-2-yl)ethoxy]pyridin-2-yl}oxy)quinazolin-4-amine hydrochloride,
6-({5-[2-(dimethylamino)ethoxy]pyridin-2-yl}oxy)-N-(5-methylpyrazin-2-yl)quinazolin-4-amine,
6-({3-chloro-5-[2-(methylamino)ethoxy]pyridin-2-yl}oxy)-N-(5-methylpyrazin-2-yl)quinazolin-4-amine hydrochloride,
6-{[3-fluoro-5-(2-pyrrolidin-1-ylethoxy)pyridin-2-yl]oxy}-N-(5-methylpyrazin-2-yl)quinazolin-4-amine,
6-({5-[2-(dimethylamino)ethoxy]-3-methylpyridin-2-yl}oxy)-N-(5-methylpyrazin-2-yl)quinazolin-4-amine hydrochloride,
6-({3-chloro-5-[2-(dimethylamino)ethoxy]pyridin-2-yl}oxy)-N-(5-methylpyrazin-2-yl)quinazolin-4-amine,
6-({5-[2-(ethylamino)ethoxy]pyridin-2-yl}oxy)-N-(5-methylpyrazin-2-yl)quinazolin-4-amine,
6-({5-[2-(isopropylamino)ethoxy]pyridin-2-yl}oxy)-N-(5-methylpyrazin-2-yl)quinazolin-4-amine,
N-(5-methylpyrazin-2-yl)-6-{[5-(2-pyrrolidin-1-ylethoxy)pyridin-2-yl]oxy}quinazolin-4-amine,
6-({3-fluoro-5-[2-(methylamino)ethoxy]pyridin-2-yl}oxy)-N-(5-methylpyrazin-2-yl)quinazolin-4-amine hydrochloride,
6-({3-fluoro-5-[2-(isopropylamino)ethoxy]pyridin-2-yl}oxy)-N-(5-methylpyrazin-2-yl)quinazolin-4-amine hydrochloride,
6-({3-methyl-5-[2-(methylamino)ethoxy]pyridin-2-yl}oxy)-N-(5-methylpyrazin-2-yl)quinazolin-4-amine hydrochloride,
6-{[5-(2-azetidin-1-ylethoxy)pyridin-2-yl]oxy}-N-(5-methylpyrazin-2-yl)quinazolin-4-amine,
6-{[3-chloro-5-(3-pyrrolidin-1-ylpropoxy)pyridin-2-yl]oxy}-N-(5-methylpyrazin-2-yl)quinazolin-4-amine hydrochloride,
6-({3-chloro-5-[2-(dimethylamino)ethoxy]pyridin-2-yl}oxy)-N-pyrazin-2-ylquinazolin-4-amine,
6-({5-[2-(dimethylamino)ethoxy]pyridin-2-yl}oxy)-N-pyrazin-2-ylquinazolin-4-amine,
6-({3-chloro-5-[2-(dimethylamino)ethoxy]pyridin-2-yl}oxy)-N-(5-methoxy[1,3]thiazolo[5,4-b]pyridin-2-yl)quinazolin-4-amine,
6-({5-[2-(dimethylamino)ethoxy]pyridin-2-yl}oxy)-N-(3-methyl)-1,2,4-thiadiazol-5-yl)quinazolin-4-amine,
6-({5-[2-(ethylamino)ethoxy]pyridin-2-yl}oxy)-N-(3-methyl)-1,2,4-thiadiazol-5-yl)quinazolin-4-amine,
2-{[5-chloro-6-({4-[(1-methyl-1H-pyrazol-3-yl)amino]quinazolin-6-yl}oxy)pyridin-3-yl]oxy}ethanol,
6-{[3-chloro-5-(2-methoxyethoxy)pyridin-2-yl]oxy}-N-(1-methyl-1H-pyrazol-3-yl)quinazolin-4-amine,
2-{[6-chloro-5-({4-[(1-methyl-1H-pyrazol-3-yl)amino]quinazolin-6-yl}oxy)pyridin-3-yl]oxy}ethanol,
2-{[6-({4-[(1-methyl-1H-pyrazol-3-yl)amino]quinazolin-6-yl}oxy)pyridin-3-yl]oxy}ethanol,
3-{[6-({4-[(1-methyl-1H-pyrazol-3-yl)amino]quinazolin-6-yl}oxy)pyridin-3-yl]oxy}propan-1-ol,
2-{[5-fluoro-6-({4-[(1-methyl-1H-pyrazol-3-yl)amino]quinazolin-6-yl}oxy)pyridin-3-yl]oxy}ethanol,
(2R)-2-{[5-chloro-6-({4-[(1-methyl-1H-pyrazol-3-yl)amino]quinazolin-6-yl}oxy)pyridin-3-yl]oxy}propan-1-ol,
(2R)-1-{[6-({4-[(1-methyl-1H-pyrazol-3-yl)amino]quinazolin-6-yl}oxy)pyridin-3-yl]oxy}propan-2-ol,
(2S)-1-{[6-({4-[(1-methyl-1H-pyrazol-3-yl)amino]quinazolin-6-yl}oxy)pyridin-3-yl]oxy}propan-2-ol,
2-{[5-chloro-6-({4-[(5-methylpyrazin-2-yl)amino]quinazolin-6-yl}oxy)pyridin-3-yl]oxy}ethanol,
2-[(5-chloro-6-{[4-(pyrazin-2-ylamino)quinazolin-6-yl]oxy}pyridin-3-yl)oxy]ethanol,
2-{[5-fluoro-6-({4-[(5-methylpyrazin-2-yl)amino]quinazolin-6-yl}oxy)pyridin-3-yl]oxy}ethanol,
3-{[5-chloro-6-({4-[(5-methylpyrazin-2-yl)amino]quinazolin-6-yl}oxy)pyridin-3-yl]oxy}propan-1-ol,
{[5-chloro-6-({4-[(5-methylpyrazin-2-yl)amino]quinazolin-6-yl}oxy)pyridin-3-yl]oxy}acetic acid,
5-chloro-N-[2-(dimethylamino)ethyl]-N-methyl-6-({4-[(1-methyl-1H-pyrazol-3-yl)amino]quinazolin-6-yl}oxy)pyridin-3-sulfonamide,
5-chloro-N-[3-(dimethylamino)propyl]-N-methyl-6-({4-[(1-methyl-1H-pyrazol-3-yl)amino]quinazolin-6-yl}oxy)pyridin-3-sulfonamide,
5-chloro-N-[2-(dimethylamino)ethyl]-N-methyl-6-({4-[(1-methyl-1H-pyrazol-3-yl)amino]quinazolin-6-yl}oxy)nicotinamide,
5-chloro-N-methyl-6-({4-[(1-methyl-1H-pyrazol-3-yl)amino]quinazolin-6-yl}oxy)-N-(2-pyrrolidin-1-ylethyl)nicotinamide,
3-chloro-N-[2-(dimethylamino)ethyl]-N-methyl-2-({4-[(1-methyl-1H-pyrazol-3-yl)amino]quinazolin-6-yl}oxy)isonicotinamide,
5-chloro-N-[3-(dimethylamino)propyl]-N-methyl-6-({4-[(1-methyl-1H-pyrazol-3-yl)amino]quinazolin-6-yl}oxy)nicotinamide,
N,N-dimethyl-2-{[5-methyl-6-({4-[(1-methyl-1H-pyrazol-3-yl)amino]quinazolin-6-yl}oxy)pyridin-3-yl]oxy}ethanamine hydrochloride,
N-methyl-2-{[5-methyl-6-({4-[(1-methyl-1H-pyrazol-3-yl)amino]quinazolin-6-yl}oxy)pyridin-3-yl]oxy}ethanamine hydrochloride,
N-ethyl-2-{[5-methyl-6-({4-[(1-methyl-1H-pyrazol-3-yl)amino]quinazolin-6-yl}oxy)pyridin-3-yl]oxy}ethanamine hydrochloride,
N-(2-{[5-methyl-6-({4-[(1-methyl-1H-pyrazol-3-yl)amino]quinazolin-6-yl}oxy)pyridin-3-yl]oxy}ethyl)propan-2-amine hydrochloride, N-{2-[(6-{[4-(pyridin-2-ylamino]quinazolin-6-yl]oxy}pyridin-3-yl)oxy]ethyl}propan-2-amine hydrochloride, N-(2-{[6-({4-[(5-methylpyridin-2-yl)amino)quinazolin-6-yl]oxy)pyridin-3-yl]oxy}ethyl)propan-2-amine hydrochloride, 6-{[5-(2-aminoethoxy)-3-chloropyridin-2-yl]oxy}-N-(5-methylpyrazin-2-yl)quinazolin-4-amine, N-(2-{[6-({4-[(2-methyl-2H-1,2,3-triazol-4-yl)amino]quinazolin-6-yl}oxy)pyridin-3-yl]oxy}ethyl)propan-2-amine hydrochloride, N-ethyl-2-({6-[(4-{[2-(propan-2-yl)-2H-1,2,3-triazol-4-yl]amino}quinazolin-6-yl)oxy]pyridin-3-yl}oxy)ethanamine hydrochloride, N-[2-({6-[(4-{[2-(propan-2-yl)-2H-1,2,3-triazol-4-yl]amino}quinazolin-6-yl)oxy]pyridin-3-yl}oxy)ethyl]cyclopropane amine hydrochloride, N-(2-{[6-({4-[(2-ethyl-2H-1,2,3-triazol-4-yl)amino]quinazolin-6-yl})oxy)pyridin-3-yl]oxy}ethyl)propan-2-amine hydrochloride, N-methyl-2-({6-[(4-{[2-(propan-2-yl)-2H-1,2,3-triazol-4-yl]amino}quinazolin-6-yl)oxy]pyridin-3-yl}oxy)ethanamine hydrochloride, N-(2-{[5-methyl-6-({4-[(2-methyl-2H-1,2,3-triazol-4-yl)amino]quinazolin-6-yl}oxy)pyridin-3-yl]oxy}ethyl)propan-2-amine hydrochloride, N-(2-{[6-({4-[(2-cyclopropyl-2H-1,2,3-triazol-4-yl)amino]quinazolin-6-yl})oxy)pyridin-3-yl]oxy}ethyl)propan-2-amine hydrochloride, (3R)-3-fluoro-1-(2-{[5-methyl-6-({4-[(2-methyl-2H-1,2,3-triazol-4-yl)amino]quinazolin-6-yl}oxy)pyridin-3-yl]oxy}ethyl)pyrrolidine hydrochloride or 2-{[5-methyl-6-({4-[(2-methyl-2H-1,2,3-triazol-4-yl)amino]quinazolin-6-yl}oxy)pyridin-3-yl]oxy}ethanol, or a pharmaceutically acceptable salt thereof;

(14) a pharmaceutical composition comprising (1) to (3), described below, used for treating, preventing and/or delaying the onset of type 2 diabetes mellitus:

(1) the compound according to the above (1) represented by the formula (I):

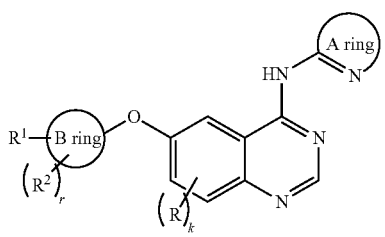

[wherein each symbol has the same definition specified above];

(2) one or more compounds selected from the group consisting of (a) to (i) described below: (a) other glucokinase activators; (b) biguanides; (c) PPAR agonists; (d) insulin; (e) somatostatins; (f) α-glucosidase inhibitors; (g) insulin secretagogues; (h) DPP-IV inhibitors (dipeptidyl peptidase inhibitors); and (i) glucose uptake facilitators; and (3) pharmacologically acceptable carriers;

(15) a glucokinase activator comprising the compound according to any one of the above (1) to (13) or the pharmaceutically acceptable salt thereof as an active ingredient;

(16) a treatment and/or a therapeutic agent for diabetes mellitus comprising the compound according to any one of the above (1) to (13) or the pharmaceutically acceptable salt thereof as an active ingredient; and

(17) a pharmaceutical composition comprising the compound according to any one of the above (1) to (13) or the pharmaceutically acceptable salt thereof.

Heteroaryloxy quinazoline derivatives according to the present invention represented by the formula (I) or pharmaceutically acceptable salts thereof have potent glucokinase-activating effects and are thus useful for treatment and/or prevention of diabetes mellitus, complications of diabetes mellitus, or obesity. The heteroaryloxy quinazoline derivatives according to the present invention are also greatly improved in properties, such as solubility, and/or drug efficacy, compared to 2-pyridinecarboxamide derivatives in related art, and thus more excellent as medicaments.

Compounds according to the present invention are adaptable for both types of diabetes mellitus, insulin dependent diabetes mellitus (IDDM) and non-insulin dependent diabetes mellitus (NIDDM).

As used herein, a diabetes mellitus complication refer to a disease accompanying due to the onset of diabetes mellitus. Specifically, examples of diabetes mellitus complications include diabetic nephropathy, diabetic retinopathy, diabetic neuropathy and diabetic arteriosclerosis.

DETAILED DESCRIPTION OF THE INVENTION

The meanings of terms as used herein are described below, and a compound according to the present invention is described in further detail.

The term "lower alkyl" refers to linear or branched $C_{1-6}$ alkyl and encompasses, for example, methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl and 1-ethyl-2-methylpropyl.

The term "lower alkoxy" refers to a group, in which a hydrogen atom of hydroxy is substituted with the above-mentioned lower alkyl, and encompasses, for example, methoxy, ethoxy, propoxy, isopropoxy, butoxy, sec-butoxy, tert-butoxy, pentyloxy, isopentyloxy, hexyloxy and isohexyloxy.

The term "halogen atom" encompasses, for example, fluorine, chlorine, bromine and iodine atoms.

The term "$C_{3-7}$ cycloalkyl" refers to a cycloalkyl group having 3 to 7 carbon atoms, specifically, e.g., cyclopropyl, cyclobutyl, cyclopentyl, cyclohexyl and cycloheptyl.

In order to further specifically disclose a compound represented by the formula (I) in accordance with the present invention

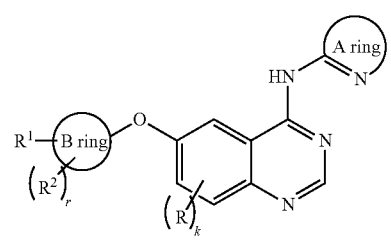

[wherein each symbol has the same definition specified above]
each symbol used in the formula (I) is described referring to specific examples.

The A ring means a 5- or 6-membered heteroaryl group that is selected from the group consisting of pyrazolyl, pyrazinyl, thiadiazolyl, thiazolyl, pyridinyl, thiatriazolyl, triazolyl, tetrazolyl, imidazolyl, pyrimidinyl, pyridazinyl, triazinyl, oxazolyl, oxadiazolyl and isoxazolyl groups, which may have one or two groups selected from the group consisting of lower alkyl, lower alkoxy, halogen, hydroxy, $C_{3-7}$ cycloalkyl and lower alkyl having 1-3 identical or different lower alkoxy groups, halogen atoms or hydroxy groups, or means a ring in which the 5- or 6-membered heteroaryl ring and a benzene or pyridine ring are condensed.

Specifically, the A ring means: a 5- or 6-membered heteroaryl group selected from the group consisting of unsubstituted pyrazolyl, pyrazinyl, thiadiazolyl, thiazolyl, pyridinyl, thiatriazolyl, triazolyl, tetrazolyl, imidazolyl, pyrimidinyl, pyridazinyl, triazinyl, oxazolyl, oxadiazolyl and isoxazolyl groups, or a ring in which the 5- or 6-membered heteroaryl ring and a benzene or pyridine ring are condensed; or a 5- or 6-membered heteroaryl group that is selected from the group consisting of pyrazolyl, pyrazinyl, thiadiazolyl, thiazolyl, pyridinyl, thiatriazolyl, triazolyl, tetrazolyl, imidazolyl, pyrimidinyl, pyridazinyl, triazinyl, oxazolyl, oxadiazolyl and isoxazolyl groups, which may have one or two groups selected from the group consisting of lower alkyl, lower alkoxy, halogen, hydroxy, $C_{3-7}$ cycloalkyl and lower alkyl having 1-3 identical or different lower alkoxy groups, halogen atoms or hydroxy groups.

A lower alkyl group that is a substituent of the A ring encompasses the same groups as the above-defined lower alkyl groups.

A lower alkoxy group that is a substituent of the A ring encompasses the same groups as the above-defined lower alkoxy groups.

A halogen atom that is a substituent of the A ring encompasses the same groups as the above-defined halogen atoms.

A cycloalkyl group that is a substituent of the A ring encompasses the same groups as the above-defined cycloalkyl groups.

A lower alkyl group having 1-3 identical or different lower alkoxy groups, halogen atoms or hydroxy groups that is a substituent of the A ring encompasses the same groups as the above-defined group having 1-3 identical or different lower alkoxy groups, halogen atoms or hydroxy groups The A ring encompasses pyrazolyl, pyrazinyl, thiadiazolyl, pyridinyl, triazolyl and thiazolopyridinyl groups, which may have one or two groups selected from the group consisting of lower alkyl, lower alkoxy, halogen, hydroxy, $C_{3-7}$ cycloalkyl and lower alkyl having 1-3 identical or different lower alkoxy groups, halogen atoms or hydroxy groups, more specifically, e.g., pyrazolyl, 1-methyl-1H-pyrazol-3-yl, 1-ethyl-1H-pyrazol-3-yl, 1-isopropyl-1H-pyrazol-3-yl, 1-propyl-1H-pyrazol-3-yl, pyrazinyl, 5-methylpyrazin-2-yl, 5-ethylpyrazin-2-yl, 5-isopropylpyrazin-2-yl, 5-propylpyrazin-2-yl, [1,3]thiazolo[5,4-b]pyridin-2-yl, 5-methoxy-[1,3]thiazolo[5,4-b]pyridin-2-yl, 5-methyl-[1,3]thiazolo[5,4-b]pyridin-2-yl, pyridin-2-yl, 5-methylpyridin-2-yl, 2-methyl-2H-1,2,3-triazol-4-yl, 2-(propan-2-yl)-2H-1,2,3-triazol-4-yl, 2-ethyl-2H-1,2,3-triazol-4-yl and 2-cyclopropyl-2H-1,2,3-triazol-4-yl groups.

The B ring means a 5- or 6-membered heteroaryl group having 1-3 identical or different hetero atoms selected from the group consisting of nitrogen, sulfur and oxygen atoms.

The B ring encompasses pyridinyl, pyrazinyl, pyrimidinyl, pyridazinyl, thiazolyl, thiadiazolyl, imidazolyl and isoxazolyl groups, among which the pyridinyl, pyrimidinyl and pyrazinyl groups are preferred.

R denotes a group selected from the group consisting of lower alkyl, lower alkoxy, halogen, hydroxy and lower alkyl having 1-3 identical or different lower alkoxy groups, halogen atoms or hydroxy groups.

The symbol k denotes an integer of from 0 to 4.

$R^1$ denotes a group represented by the formula (II-1)

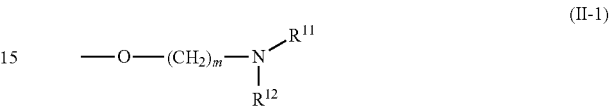

a group represented by the formula (II-2)

a group represented by the formula (II-3)

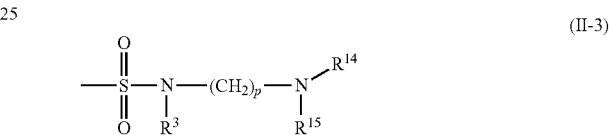

and a group represented by the formula (II-4)

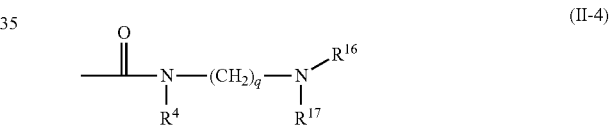

The group represented by the formula (II-1) is described.

$R^{11}$ and $R^{12}$ each independently denote hydrogen, lower alkyl or $C_{3-7}$ cycloalkyl.

The term "lower alkyl" represented by $R^{11}$ and $R^{12}$ refers to an identical group as "lower alkyl" defined above and specifically encompasses, e.g., methyl, ethyl, isopropyl and propyl groups.

The term "$C_{3-7}$ cycloalkyl" represented by $R^{11}$ and $R^{12}$ refers to cyclopropyl, cyclobutyl, cyclopentyl, cyclohexyl and cycloheptyl.

$R^{11}$ and $R^{12}$, together with the nitrogen atom to which they are bound, also form 4- to 7-membered nitrogen-containing aliphatic rings. The 4- to 7-membered nitrogen-containing aliphatic rings may be substituted with 1-3 identical or different halogen atoms.

Examples of 4- to 7-membered nitrogen-containing aliphatic rings specifically include azetidin-1-yl, pyrrolidin-1-yl, 2-methylpyrrolidin-1-yl, piperidin-1-yl, hexamethyleneimin-1-yl and 3-fluoro-pyrrolidin-1-yl.

Any carbon atom of $(CH_2)_m$, together with $R^{11}$ or $R^{12}$, may also form 4- to 7-membered nitrogen-containing aliphatic rings.

Examples of "4- to 7-membered nitrogen-containing aliphatic rings" formed by any carbon atom of $(CH_2)_m$, together with $R^{11}$ or $R^{12}$, specifically include 1-methylazetidin-3-yl, 1-ethylazetidin-3-yl, 1-isopropylazetidin-3-yl, 1-isopropylpyrrolidin-3-yl, 1-methylpyrrolidin-2-yl, pyrrolidin-3-yl, 1-methylpyrrolidin-3-yl, 1-ethylpyrrolidin-3-yl and 1-methylpiperidin-4-yl.

Any carbon atom in the $(CH_2)_m$ may be substituted with the above-defined lower alkyl.

The nitrogen atom to which $R^{11}$ and $R^{12}$ are bound may form N-oxide.

The symbol m refers to an integer of from 2 to 6.

The group represented by the formula (II-2) will now be described.

$R^{13}$ refers to a lower alkoxy, hydroxy or carboxyl group.

The lower alkoxy group represented by $R^{13}$ refers to an identical group as the above-defined lower alkoxy.

In addition, upon $R^{13}$ being lower alkoxy, the lower alkoxy, together with any carbon atom of $(CH_2)_n$, may form 5- to 7-membered aliphatic rings.

Examples of the 5- to 7-membered aliphatic rings specifically include cyclopentyl, cyclohexyl and cycloheptyl groups.

Any carbon atom of $(CH_2)_n$ may be also substituted with a lower alkyl group.

The symbol n refers to an integer of from 1 to 6.

The formula (II-3) is described.

$R^{14}$ and $R^{15}$ are synonymous with the above $R^{11}$ and $R^{12}$.

$R^3$ refers to a hydrogen atom or a lower alkyl group.

The symbol p refers to an integer of from 2 to 6.

The formula (II-4) is described.

$R^{16}$ and $R^{17}$ are synonymous with the above $R^{11}$ and $R^{12}$.

$R^4$ refers to a hydrogen atom or a lower alkyl group.

The symbol q refers to an integer of from 2 to 6.

$R^2$ refers to a group selected from the group consisting of lower alkyl, lower alkoxy, halogen, hydroxy, cyano, carboxyl, alkoxycarbonyl, N-alkylcarbamoyl, N,N-dialkylcarbamoyl, lower alkylsulfonyl and lower alkyl having 1-3 identical or different lower alkoxy groups, halogen atoms, hydroxy groups, cyano groups, carboxyl groups, alkoxycarbonyl groups, N-alkylcarbamoyl groups, N,N-dialkylcarbamoyl groups or lower alkylsulfonyl groups.

$R^1$ is preferably the group represented by the formula (II-1) or (II-2), more preferably the group represented by the formula (II-1).

In a preferred embodiment of the group represented by the formula (II-1), for example, one of $R^{11}$ and $R^{12}$ is a hydrogen atom and the other is a lower alkyl or $C_{3-7}$ cycloalkyl group.

In another preferred embodiment of the group represented by the formula (II-1), for example, $R^{11}$ and $R^{12}$ each independently are lower alkyl or $C_{3-7}$ cycloalkyl groups.

In another preferred embodiment of the group represented by the formula (II-1), for example, $R^{11}$ and $R^{12}$ are 4- to 7-membered nitrogen-containing aliphatic rings formed by $R^{11}$ and $R^{12}$ together with the nitrogen atom to which they are bound, (the 4- to 7-membered nitrogen-containing aliphatic rings may be substituted with 1-3 identical or different halogen atoms; and the nitrogen atom to which $R^{11}$ and $R^{12}$ are bound may form N-oxide).

In another preferred embodiment of the group represented by the formula (II-1), for example, $R^{11}$ and $R^{12}$ are 4- to 7-membered nitrogen-containing aliphatic rings formed by either $R^{11}$ or $R^{12}$ together with any carbon atom of $(CH_2)_m$ (any carbon atom in the $(CH_2)_m$ may be substituted with a lower alkyl group).

Any preferred aspects of R, $R^1$, $R^2$, $R^3$, $R^4$, $R^{11}$, $R^{12}$, $R^{13}$, $R^{14}$, $R^{15}$, $R^{16}$, $R^{17}$, k, m, n, p, q and r may be combined.

Compounds represented by the formula (I) specifically include, for example, 6-({3-chloro-5-[2-(dimethylamino)ethoxy]pyridin-2-yl}oxy)-N-(1-methyl-1H-pyrazol-3-yl)quinazolin-4-amine,
6-({2-chloro-5-[2-(dimethylamino)ethoxy]pyridin-3-yl}oxy)-N-(1-methyl-1H-pyrazol-3-yl)quinazolin-4-amine,
6-({6-[2-(dimethylamino)ethoxy]pyridin-3-yl}oxy)-N-(1-methyl-1H-pyrazol-3-yl)quinazolin-4-amine,
6-({5-[3-(dimethylamino)propoxy]pyridin-2-yl}oxy)-N-(1-methyl-1H-pyrazol-3-yl)quinazolin-4-amine,
6-({5-[2-(isopropylamino)ethoxy]pyridin-2-yl}oxy)-N-(1-methyl-1H-pyrazol-3-yl)quinazolin-4-amine,
6-({5-[(1-methylazetidin-3-yl)oxy]pyridin-2-yl}oxy)-N-(1-methyl-1H-pyrazol-3-yl)quinazolin-4-amine,
6-({2-[2-(dimethylamino)ethoxy]pyrimidin-5-yl}oxy)-N-(1-methyl-1H-pyrazol-3-yl)quinazolin-4-amine,
6-({5-[2-(dimethylamino)ethoxy]pyrimidin-2-yl}oxy)-N-(1-methyl-1H-pyrazol-3-yl)quinazolin-4-amine,
N-(1-methyl-1H-pyrazol-3-yl)-6-{[5-(2-piperidin-1-yl)ethoxy)pyridin-2-yl]oxy}quinazolin-4-amine,
6-[(5-{2-[ethyl(methyl)amino]ethoxy}pyridin-2-yl)oxy]-N-(1-methyl-1H-pyrazol-3-yl)quinazolin-4-amine hydrochloride,
6-({5-[2-(diethylamino)ethoxy]pyridin-2-yl}oxy)-N-(1-methyl-1H-pyrazol-3-yl)quinazolin-4-amine hydrochloride,
6-[(5-{2-[(3R)-3-fluoropyrrolidin-1-yl]ethoxy}pyridin-2-yl)oxy]-N-(1-methyl-1H-pyrazol-3-yl)quinazolin-4-amine hydrochloride,
6-[(5-{2-[(3S)-3-fluoropyrrolidin-1-yl]ethoxy}pyridin-2-yl)oxy]-N-(1-methyl-1H-pyrazol-3-yl)quinazolin-4-amine hydrochloride,
N-(1-methyl-1H-pyrazol-3-yl)-6-[(5-{2-[(2R)-2-methylpyrrolidin-1-yl]ethoxy}pyridin-2-yl)oxy]quinazolin-4-amine hydrochloride,
N-(1-methyl-1H-pyrazol-3-yl)-6-[(5-{2-[(2S)-2-methylpyrrolidin-1-yl]ethoxy}pyridin-2-yl)oxy]quinazolin-4-amine hydrochloride,
6-({5-[2-(cyclobutylamino)ethoxy]pyridin-2-yl}oxy)-N-(1-methyl-1H-pyrazol-3-yl)quinazolin-4-amine hydrochloride,
6-({5-[2-(cyclopentylamino)ethoxy]pyridin-2-yl}oxy)-N-(1-methyl-1H-pyrazol-3-yl)quinazolin-4-amine hydrochloride,
6-({3-chloro-5-[2-(ethylamino)ethoxy]pyridin-2-yl}oxy)-N-(1-methyl-1H-pyrazol-3-yl)quinazolin-4-amine hydrochloride,
6-({5-[2-(ethylamino)ethoxy]-3-fluoropyridin-2-yl}oxy)-N-(1-methyl-1H-pyrazol-3-yl)quinazolin-4-amine hydrochloride,
6-({3-chloro-5-[3-(ethylamino)propoxy]pyridin-2-yl}oxy)-N-(1-methyl-1H-pyrazol-3-yl)quinazolin-4-amine hydrochloride,
6-({3-chloro-5-[3-(isopropylamino)propoxy]pyridin-2-yl}oxy)-N-(1-methyl-1H-pyrazol-3-yl)quinazolin-4-amine hydrochloride,
6-({3-chloro-5-[3-(methylamino)propoxy]pyridin-2-yl}oxy)-N-(1-methyl-1H-pyrazol-3-yl)quinazolin-4-amine hydrochloride,
6-{[5-(azetidin-3-yloxy)-3-chloropyridin-2-yl]oxy}-N-(1-methyl-1H-pyrazol-3-yl)quinazolin-4-amine hydrochloride,
6-({5-[(1-isopropylazetidine-3-yl)oxy]pyridin-2-yl}oxy)-N-(1-methyl-1H-pyrazol-3-yl)quinazolin-4-amine hydrochloride,
6-({5-[(1-ethylazetidin-3-yl)oxy]-3-fluoropyridin-2-yl}oxy)-N-(1-methyl-1H-pyrazol-3-yl)quinazolin-4-amine hydrochloride, 6-[(5-{[(2S)-2-(methylamino)propyl]oxy}pyridin-2-yl)oxy]-N-(1-methyl-1H-pyrazol-3-yl)quinazolin-4-amine,
6-[(5-{[(2R)-2-(methylamino)propyl]oxy}pyridin-2-yl)oxy]-N-(1-methyl-1H-pyrazol-3-yl)quinazolin-4-amine,
6-({5-[(1-methylazetidin-3-yl)methoxy]pyridin-2-yl}oxy)-N-(1-methyl-1H-pyrazol-3-yl)quinazolin-4-amine hydrochloride,
N-(1-methyl-1H-pyrazol-3-yl)-6-{[5-(2-pyrrolidin-2-ylethoxy)pyridin-2-yl]oxy}quinazolin-4-amine,
N-(1-methyl-1H-pyrazol-3-yl)-6-({5-[2-(1-methylpyrrolidin-2-yl)ethoxy]pyridin-2-yl}oxy)quinazolin-4-amine hydrochloride,
6-({5-[2-(dimethylamino)ethoxy]pyridin-2-yl}oxy)-N-(5-methylpyrazin-2-yl)quinazolin-4-amine,
6-({3-chloro-5-[2-(methylamino)ethoxy]pyridin-2-yl}oxy)-N-(5-methylpyrazin-2-yl)quinazolin-4-amine hydrochloride,
6-{[3-fluoro-5-(2-pyrrolidin-1-ylethoxy)pyridin-2-yl]oxy}-N-(5-methylpyrazin-2-yl)quinazolin-4-amine,
6-({5-[2-(dimethylamino)ethoxy]-3-methylpyridin-2-yl}oxy)-N-(5-methylpyrazin-2-yl)quinazolin-4-amine hydrochloride,
6-({3-chloro-5-[2-(dimethylamino)ethoxy]pyridin-2-yl}oxy)-N-(5-methylpyrazin-2-yl)quinazolin-4-amine,
6-({5-[2-(ethylamino)ethoxy]pyridin-2-yl}oxy)-N-(5-methylpyrazin-2-yl)quinazolin-4-amine,
6-({5-[2-(isopropylamino)ethoxy]pyridin-2-yl}oxy)-N-(5-methylpyrazin-2-yl)quinazolin-4-amine,
N-(5-methylpyrazin-2-yl)-6-{[5-(2-pyrrolidin-1-ylethoxy)pyridin-2-yl]oxy}quinazolin-4-amine,
6-({3-fluoro-5-[2-(methylamino)ethoxy]pyridin-2-yl}oxy)-N-(5-methylpyrazin-2-yl)quinazolin-4-amine hydrochloride,
6-({3-fluoro-5-[2-(isopropylamino)ethoxy]pyridin-2-yl}oxy)-N-(5-methylpyrazin-2-yl)quinazolin-4-amine hydrochloride,
6-({3-methyl-5-[2-(methylamino)ethoxy]pyridin-2-yl}oxy)-N-(5-methylpyrazin-2-yl)quinazolin-4-amine hydrochloride,
6-{[5-(2-azetidin-1-ylethoxy)-pyridin-2-yl]oxy}-N-(5-methylpyrazin-2-yl)quinazolin-4-amine,
6-{[3-chloro-5-(3-pyrrolidin-1-ylpropoxy)pyridin-2-yl]oxy}-N-(5-methylpyrazin-2-yl)quinazolin-4-amine hydrochloride,
6-({3-chloro-5-[2-(dimethylamino)ethoxy]pyridin-2-yl}oxy)-N-pyrazin-2-ylquinazolin-4-amine,
6-({5-[2-(dimethylamino)ethoxy]pyridin-2-yl}oxy)-N-pyrazin-2-ylquinazolin-4-amine,
6-({3-chloro-5-[2-(dimethylamino)ethoxy]pyridin-2-yl}oxy)-N-(5-methoxy[1,3]thiazolo[5,4-b]pyridin-2-yl)quinazolin-4-amine,
6-({5-[2-(dimethylamino)ethoxy]pyridin-2-yl}oxy)-N-(3-methyl-1,2,4-thiadiazol-5-yl)quinazolin-4-amine,
6-({5-[2-(ethylamino)ethoxy]pyridin-2-yl}oxy)-N-(3-methyl-1,2,4-thiadiazol-5-yl)quinazolin-4-amine,
2-{[5-chloro-6-({4-[(1-methyl-1H-pyrazol-3-yl)amino]quinazolin-6-yl}oxy)pyridin-3-yl]oxy}ethanol,
6-{[3-chloro-5-(2-methoxyethoxy)pyridin-2-yl]oxy}-N-(1-methyl-1H-pyrazol-3-yl)quinazolin-4-amine,
2-{[6-chloro-5-({4-[(1-methyl-1H-pyrazol-3-yl)amino]quinazolin-6-yl}oxy)pyridin-3-yl]oxy}ethanol,
2-{[6-({4-[(1-methyl-1H-pyrazol-3-yl)amino]quinazolin-6-yl}oxy)pyridin-3-yl]oxy}ethanol,
3-{[6-({4-[(1-methyl-1H-pyrazol-3-yl)amino]quinazolin-6-yl}oxy)pyridin-3-yl]oxy}propan-1-ol,
2-{[5-fluoro-6-({4-[(1-methyl-1H-pyrazol-3-yl)amino]quinazolin-6-yl}oxy)pyridin-3-yl]oxy}ethanol,
(2R)-2-{[5-chloro-6-({4-[(1-methyl-1H-pyrazol-3-yl)amino]quinazolin-6-yl}oxy)pyridin-3-yl]oxy}propan-1-ol,
(2R)-1-{[6-({4-[(1-methyl-1H-pyrazol-3-yl)amino]quinazolin-6-yl}oxy)pyridin-3-yl]oxy}propan-2-ol,
(2S)-1-{[6-({4-[(1-methyl-1H-pyrazol-3-yl)amino]quinazolin-6-yl}oxy)pyridin-3-yl]oxy}propan-2-ol,
2-{[5-chloro-6-({4-[(5-methylpyrazin-2-yl)amino]quinazolin-6-yl}oxy)pyridin-3-yl]oxy}ethanol,
2-[(5-chloro-6-{[4-(pyrazin-2-ylamino)quinazolin-6-yl]oxy}pyridin-3-yl)oxy]ethanol,
2-{[5-fluoro-6-({4-[(5-methylpyrazin-2-yl)amino]quinazolin-6-yl}oxy)pyridin-3-yl]oxy}ethanol,
3-{[5-chloro-6-({4-[(5-methylpyrazin-2-yl)amino]quinazolin-6-yl}oxy)pyridin-3-yl]oxy}propan-1-ol,
{[5-chloro-6-({4-[(5-methylpyrazin-2-yl)amino]quinazolin-6-yl}oxy)pyridin-3-yl]oxy}acetic acid,
5-chloro-N-[2-(dimethylamino)ethyl]-N-methyl-6-({4-[(1-methyl-1H-pyrazol-3-yl)amino]quinazolin-6-yl}oxy)pyridin-3-sulfonamide,
5-chloro-N-[3-(dimethylamino)propyl]-N-methyl-6-({4-[(1-methyl-1H-pyrazol-3-yl)amino]quinazolin-6-yl}oxy)pyridin-3-sulfonamide,
5-chloro-N-[2-(dimethylamino)ethyl]-N-methyl-6-({4-[(1-methyl-1H-pyrazol-3-yl)amino]quinazolin-6-yl}oxy)nicotinamide,
5-chloro-N-methyl-6-({4-[(1-methyl-1H-pyrazol-3-yl)amino]quinazolin-6-yl}oxy)-N-(2-pyrrolidin-1-ylethyl)nicotinamide,
3-chloro-N-[2-(dimethylamino)ethyl]-N-methyl-2-({4-[(1-methyl-1H-pyrazol-3-yl)amino]quinazolin-6-yl}oxy)isonicotinamide,
5-chloro-N-[3-(dimethylamino)propyl]-N-methyl-6-({4-[(1-methyl-1H-pyrazol-3-yl)amino]quinazolin-6-yl}oxy)nicotinamide,
N,N-dimethyl-2-{[5-methyl-6-({4-[(1-methyl-1H-pyrazol-3-yl)amino]quinazolin-6-yl}oxy)pyridin-3-yl]oxy}ethanamine hydrochloride,
N-methyl-2-{[5-methyl-6-({4-[(1-methyl-1H-pyrazol-3-yl)amino]quinazolin-6-yl}oxy)pyridin-3-yl]oxy}ethanamine hydrochloride,
N-ethyl-2-{[5-methyl-6-({4-[(1-methyl-1H-pyrazol-3-yl)amino]quinazolin-6-yl}oxy)pyridin-3-yl]oxy}ethanamine hydrochloride,
N-(2-{[5-methyl-6-({4-[(1-methyl-1H-pyrazol-3-yl)amino]quinazolin-6-yl}oxy)pyridin-3-yl]oxy}ethyl)propan-2-amine hydrochloride,
N-{2-[(6-{[4-(pyridin-2-ylamino)quinazolin-6-yl]oxy}pyridin-3-yl)oxy]ethyl}propan-2-amine hydrochloride,
N-(2-{[6-({4-[(5-methylpyridin-2-yl)amino]quinazolin-6-yl}oxy)pyridin-3-yl]oxy}ethyl)propan-2-amine hydrochloride,
6-{[5-(2-aminoethoxy)-3-chloropyridin-2-yl]oxy}-N-(5-methylpyrazin-2-yl)quinazolin-4-amine,
N-(2-{[6-({4-[(2-methyl-2H-1,2,3-triazol-4-yl)amino]quinazolin-6-yl}oxy)pyridin-3-yl]oxy}ethyl)propan-2-amine hydrochloride,
N-ethyl-2-({6-[(4-{[2-(propan-2-yl)-2H-1,2,3-triazol-4-yl]amino}quinazolin-6-yl)oxy]pyridin-3-yl}oxy)ethanamine hydrochloride,
N-[2-({6-[(4-{[2-(propan-2-yl)-2H-1,2,3-triazol-4-yl]amino}quinazolin-6-yl)oxy]pyridin-3-yl}oxy)ethyl]cyclopropane amine hydrochloride,
N-(2-{[6-({4-[(2-ethyl-2H-1,2,3-triazol-4-yl)amino]quinazolin-6-yl}oxy)pyridin-3-yl]oxy}ethyl)propan-2-amine hydrochloride, N-methyl-2-({6-[(4-{[2-(propan-2-yl)-2H-1,2,3-triazol-4-yl]amino}quinazolin-6-yl)oxy]pyridin-3-yl}oxy)ethanamine hydrochloride,
N-(2-{[5-methyl-6-({4-[(2-methyl-2H-1,2,3-triazol-4-yl)amino]quinazolin-6-yl}oxy)pyridin-3-yl]oxy}ethyl)propan-2-amine hydrochloride,
N-(2-{[6-({4-[(2-cyclopropyl-2H-1,2,3-triazol-4-yl)amino]quinazolin-6-yl}oxy)pyridin-3-yl]oxy}ethyl)propan-2-amine hydrochloride,
(3R)-3-fluoro-1-(2-{[5-methyl-6-({4-[(2-methyl-2H-1,2,3-triazol-4-yl)amino]quinazolin-6-yl}oxy)pyridin-3-yl]oxy}ethyl)pyrrolidine hydrochloride and
2-{[5-methyl-6-({4-[(2-methyl-2H-1,2,3-triazol-4-yl)amino]quinazolin-6-yl}oxy)pyridin-3-yl]oxy}ethanol.

The compounds of the formula (I) of the present invention can be produced, for example, according to the method mentioned below.

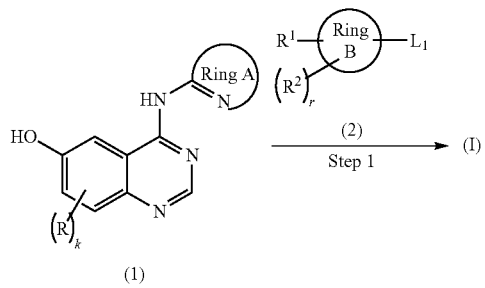

[In the formula, $L_1$ represents a leaving group, and the other symbols are the same as above.]

(Step 1)

This step is a method of reacting a compound (1) and a compound (2) in the presence of a base to produce the compound (I) of the invention.

The compound (1) to be used can be produced according to the method described in literature (e.g., WO2005/090332), or according to a method similar to it, or according to a combination thereof with an ordinary method.

The base to be used includes, for example, potassium tert-butoxide, lithium diisopropylamide, sodium tert-pentoxide, cesium carbonate, sodium hydrogencarbonate.

The amount of the base to be used may be generally from 1 to 10 equivalents relative to 1 equivalent of the compound (1), preferably from 1 to 3 equivalents.

The leaving group for $L_1$ is, for example, preferably a fluorine atom, a chlorine atom, a bromine atom, or an iodine atom.

The amount of the compound (2) to be used may be generally from 1 to 10 equivalents relative to 1 equivalent of the compound (1), preferably from 1 to 3 equivalents.

Not specifically defined, the reaction solvent may be any one not interfering with the reaction, and includes, for example, dimethylacetamide (this may be referred to as DMA), N,N-dimethylformamide (this may be referred to as DMF), dimethyl sulfoxide (this may be referred to as DMSO).

The reaction temperature may be generally from 80 to 200° C.

The reaction time may be generally from 1 to 50 hours, preferably from 1 to 25 hours.

The reaction in this step may be carried out generally in a sealed tube or under an inert gas atmosphere.

Thus obtained, the compound (I) may be isolated and purified in a known separation and purification method of, for example, concentration, concentration under reduced pressure, reprecipitation, solvent extraction, crystallization or chromatography.

Compounds of a formula (I-1) of the invention:

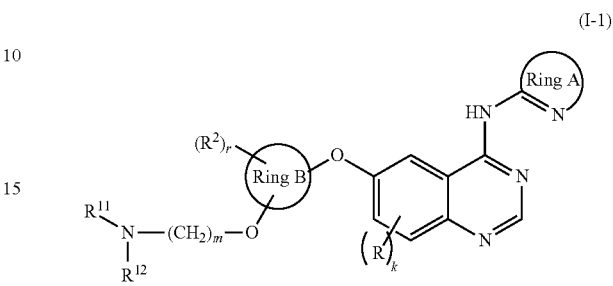

can be produced, for example, according to the following method:

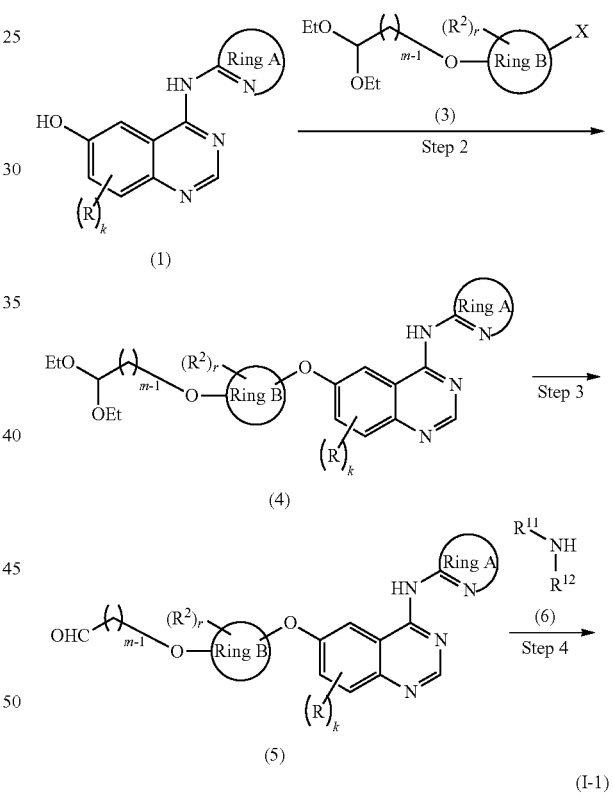

[In the formula, X represents a leaving group, and the other symbols are the same as above.]

(Step 2)

This step is a method of reacting a compound (1) and a compound (3) in the presence of a base to produce a compound (4).

The base to be used includes, for example, potassium tert-butoxide, lithium diisopropylamide, sodium tert-pentoxide, cesium carbonate, sodium hydrogencarbonate.

The amount of the base to be used may be generally from 1 to 10 equivalents relative to 1 equivalent of the compound (1), preferably from 1 to 3 equivalents.

The leaving group for X is, for example, preferably a fluorine atom, a chlorine atom, a bromine atom, or an iodine atom.

The compound (3) to be used includes, concretely for example, 2,3-dichloro-5-(2,2-diethoxyethoxy)pyridine, 5-(2,2-diethoxyethoxy)-2-fluoropyridine, 2-(2,2-diethoxyethoxy)-5-fluoropyrimidine, 2-chloro-5-(2,2-diethoxyethoxy)pyrimidine, 5-(2,2-diethoxyethoxy)-2,3-difluoropyridine, 3-chloro-5-(2,2-diethoxyethoxy)-2-fluoropyridine, 5-(2,2-diethoxyethoxy)-2-fluoro-3-methylpyridine.

The amount of the compound (3) to be used may be generally from 1 to 10 equivalents relative to 1 equivalent of the compound (1), preferably from 1 to 3 equivalents.

Not specifically defined, the reaction solvent may be any one not interfering with the reaction, and includes, for example, DMA, DMF, DMSO.

The reaction temperature may be generally from 100 to 200° C.

The reaction in this step may be carried out, using a microwave reactor.

The reaction time may be generally from 0.1 to 5 hours, preferably from 0.2 to 2 hours.

The reaction in this step may be carried out generally in a sealed tube or under an inert gas atmosphere.

Thus obtained, the compound (4) may be isolated and purified in a known separation and purification method of, for example, concentration, concentration under reduced pressure, reprecipitation, solvent extraction, crystallization or chromatography, or not isolated and purified, this may be subjected to the next step.

(Step 3)

This step is a method of hydrolyzing the compound (4) with an acid to produce a compound (5).

The acid to be used includes formic acid, hydrochloric acid, acetic acid, trifluoroacetic acid.

The amount of the acid to be used may be generally from 1 equivalent to a solvent amount relative to 1 equivalent of the compound (4), preferably from 1 to 100 equivalents.

Not specifically defined, the reaction solvent may be any one not interfering with the reaction, and includes, for example, chloroform, methylene chloride, DMF, methanol, ethanol, water, and their mixed solvents.

The reaction time may be generally from 0.2 to 10 hours, preferably from 0.2 to 5 hours.

Thus obtained, the compound (5) may be isolated and purified in a known separation and purification method of, for example, concentration, concentration under reduced pressure, reprecipitation, solvent extraction, crystallization or chromatography, or not isolated and purified, this may be subjected to the next step.

(Step 4)

This step is a method of reacting the compound (5) obtained in the previous step 3 and a compound (6) in the presence of a reducing agent to produce a compound (I-1) of the invention.

The amount of the compound (6) to be used may be generally from 1 to 20 equivalents relative to 1 equivalent of the compound (5), preferably from 1 to 5 equivalents.

The reducing agent to be used includes sodium triacetoxyborohydride, sodium cyanoborohydride, sodium borohydride.

The amount of the reducing agent to be used may be generally from 1 to 10 equivalents relative to 1 equivalent of the compound (5), preferably from 1 to 5 equivalents.

Zinc chloride, acetic acid, trifluoroacetic acid, magnesium chloride, boron trifluoride or the like may be added to the reaction system, and its amount may be generally from 1 to 10 equivalents relative to 1 equivalent of the compound (5), preferably from 1 to 3 equivalents.

Not specifically defined, the reaction solvent may be any one not interfering with the reaction and includes, for example, methanol, ethanol, acetic acid, tetrahydrofuran (THF), chloroform, dichloromethane. Of those, for example, preferred are chloroform, THF.

The reaction time may be generally from 1 hour to 24 hours, preferably from 1 hour to 8 hours.

The reaction temperature may be generally from 0° C. to 100° C., preferably from 0° C. to 40° C.

Thus obtained, the compound (I-1) of the invention may be isolated and purified in a known separation and purification method of, for example, concentration, concentration under reduced pressure, crystallization, solvent extraction, reprecipitation or chromatography.

Compounds (I-1) of the invention may also be produced according to the following method:

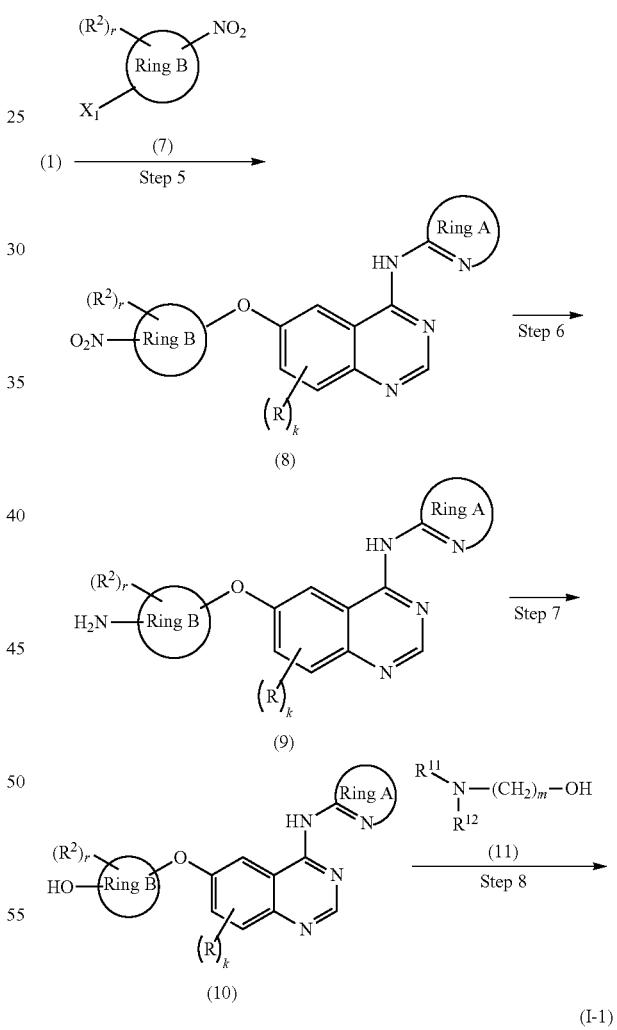

[In the formula, $X_1$ represents a leaving group, and the other symbols have the same meanings as above.]

(Step 5)

This step is a method of reacting the above compound (1) with a compound (7) in the presence of a base to produce a compound (8).

The base to be used includes, for example, sodium hydride, cesium carbonate.

The amount of the base to be used may be generally from 1 to 5 equivalents relative to 1 equivalent of the compound (1), preferably from 1 to 3 equivalents.

The leaving group for $X_1$ includes, for example, a fluorine atom, a chlorine atom, a bromine atom, an iodine atom.

The compound (7) to be used includes, for example, 5-bromo-2-nitropyridine.

The amount of the compound (7) to be used may be generally from 1 to 5 equivalents relative to 1 equivalent of the compound (1), preferably from 1 to 2 equivalents.

Not specifically defined, the reaction solvent may be any one not interfering with the reaction, and includes, for example, DMA, DMF, THF.

The reaction temperature may be generally from 20° C. to 100° C., preferably from 30° C. to 80° C.

The reaction time may be generally from 1 hour to 50 hours, preferably from 1 hour to 20 hours.

Thus obtained, the compound (8) may be isolated and purified in a known separation and purification method of, for example, concentration, concentration under reduced pressure, reprecipitation, solvent extraction, crystallization or chromatography, or not isolated and purified, this may be subjected to the next step.

(Step 6)

This step is a method of reducing the nitro group that the compound (8) has, thereby producing a compound (9).

The reducing agent to be used includes, for example, iron powder, palladium.

The amount of the reducing agent to be used may be generally from 0.01 to 50 equivalents relative to 1 equivalent of the compound (8), preferably from 0.1 to 10 equivalents.

Ammonium chloride or ammonium acetate may be present in the reaction system, and the reaction may be attained under a hydrogen atmosphere.

Not specifically defined, the reaction solvent may be any one not interfering with the reaction, and includes, for example, methanol, ethanol, THF, water or their mixed solvents.

The reaction temperature may be generally from 20° C. to 150° C., preferably from 50° C. to 100° C.

The reaction time may be generally from 0.2 hours to 10 hours, preferably from 0.2 hours to 5 hours.

Thus obtained, the compound (9) may be isolated and purified in a known separation and purification method of, for example, concentration, concentration under reduced pressure, reprecipitation, solvent extraction, crystallization or chromatography, or not isolated and purified, this may be subjected to the next step.

(Step 7)

This step is a method of converting the amino group that the compound (9) has, into a hydroxyl group, thereby producing a compound (10).

The reaction in this step may be attained by reacting the compound (9) with sodium nitrite in the presence of an acid.

The amount of sodium nitrite to be used may be generally from 1 to 5 equivalents relative to 1 equivalent of the compound (9), preferably from 1 to 2 equivalents.

The acid to be used includes sulfuric acid.

The amount of the acid to be used may be generally from 20 to 200 equivalents relative to 1 equivalent of the compound (9), preferably from 50 to 100 equivalents.

The reaction temperature may be generally from −20° C. to 30° C., preferably from −20° C. to 0° C.

The reaction time may be generally from 0.2 hours to 12 hours, preferably from 0.2 hours to 6 hours.

The compound (10) may also be produced by stirring the above compound (5) (where m is 3) in the presence of a base.

The base to be used includes, for example, triethylamine, diisopropylethylamine.

The amount of the base to be used may be generally from 1 to 5 equivalents relative to 1 equivalent of the compound (5), preferably from 2 to 3 equivalents.

Not specifically defined, the reaction solvent may be any one not interfering with the reaction, and includes, for example, THF.

The reaction temperature may be generally from 0° C. to 100° C., preferably from 20° C. to 40° C.

The reaction time may be generally from 1 to 48 hours, preferably from 4 to 12 hours.

Thus obtained, the compound (10) may be isolated and purified in a known separation and purification method of, for example, concentration, concentration under reduced pressure, reprecipitation, solvent extraction, crystallization or chromatography, or not isolated and purified, this may be subjected to the next step.

(Step 8)

This step is a method of reacting the compound (10) with a compound (11) to produce a compound (I-1) of the invention.

The reaction of the compound (10) with a compound (11) is so-called Mitsunobu reaction, which may be effected in the presence of a phosphine compound and an azo compound, according to a method described in literature (e.g., "The use of diethyl azodicarboxylate and triphenylphosphine in synthesis and transformation of natural products", by Mitsunobu O.; Synthesis, Vol. 1, 1981, pp. 1-28), or according to a method similar to it, or according to an ordinary method combined with it.

The amount of the alcohol compound (11) to be used may be generally from 0.5 to 10 equivalents relative to 1 equivalent of the compound (10), preferably from 1 to 3 equivalents.

The phosphine compound to be used in this step is generally, for example, triphenyl phosphine, tributyl phosphine.

The amount of the phosphine compound to be used may be generally from 0.5 to 10 equivalents, preferably from 1 to 3 equivalents relative to 1 equivalent of the compound (10).

The azo compound to be used includes, for example, diethyl azodicarboxylate, diisopropyl azodicarboxylate.

The amount of the azo compound to be used may be generally from 0.5 to 10 equivalents, preferably from 1 to 3 equivalents relative to 1 equivalent of the compound (10).

Not specifically defined, the reaction solvent to be used in this step may be any one not interfering with the reaction, and includes, for example, THF, toluene.

The reaction temperature in this step may be generally from 0° C. to the reflux temperature of the reaction solvent, preferably from 15 to 30° C.

The reaction time in this step may be generally from 1 to 48 hours, preferably from 4 to 12 hours.

Thus obtained, the compound (I-1) may be isolated and purified in a known separation and purification method of, for example, concentration, concentration under reduced pressure, reprecipitation, solvent extraction, crystallization or chromatography.

Compound (I-1) of the invention may also be produced, for example, according to the following method:

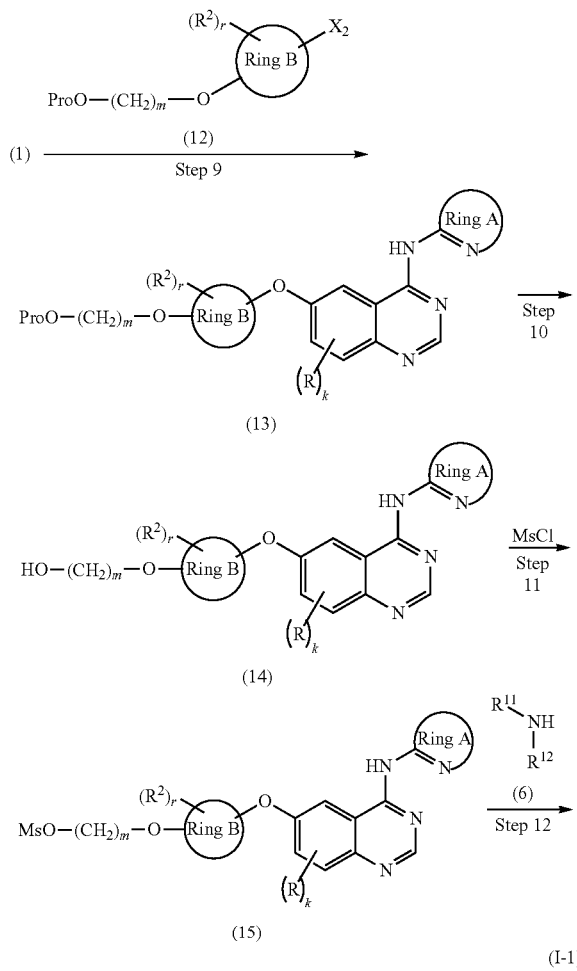

[In the formula, $X_2$ represents a leaving group; Pro represents a hydroxy-protective group; Ms represents a methanesulfonyl group; and the other symbols have the same meanings as above.]

(Step 9)

his step is a method of reacting a compound (1) with a compound (12) in the presence of a base to produce a compound (13). The reaction in this step may be attained according to the method described in the above step 1 or 2, or according to a method similar to it, or according to a combination thereof with an ordinary method.

The compound (12) to be used includes, for example, 2-fluoro-5-[3-(tetrahydro-2H-pyran-2-yloxy)propoxy]pyridine, 3-chloro-2-fluoro-5-[3-(tetrahydro-2H-pyran-2-yloxy)propoxy]pyridine.

The hydroxy-protective group in the compound (12) includes, for example, a tetrahydropyranyl (THP) group, a methoxymethyl (MOM) group, an ethoxyethyl (EE) group.

Thus obtained, the compound (13) may be isolated and purified in a known separation and purification method of, for example, concentration, concentration under reduced pressure, reprecipitation, solvent extraction, crystallization or chromatography, or not isolated and purified, this may be subjected to the next step.

(Step 10)

This step is a method of removing the hydroxyl-protective group Pro from the compound (13) to produce a compound (14).

The removal of the protective group in this step may be attained in the same manner as in the method described in literature (for example, Protective Groups in Organic Synthesis, by T. W. Green, 2nd Ed., John Wiley & Sons, 1991), or in accordance with it, or by combining it with an ordinary method.

For example, when the hydroxyl-protective group is a THP group, then the compound (13) may be reacted with pyridinium p-toluenesulfonate (PPTS) in a solvent such as ethanol, thereby removing the THP group.

The compound (14) may also be produced by reacting the above compound (10) with a compound (12-1):

$$\text{ProO—(CH}_2)_m\text{—OMs} \quad (12\text{-}1)$$

(wherein Ms represents a methanesulfonyl group; and the other symbols have the same meanings as above), in the presence of a base.

The base to be used includes, for example, potassium tert-butoxide, lithium diisopropylamide, cesium carbonate, sodium hydride.

The amount of the base to be used may be generally from 1 to 5 equivalents relative to 1 equivalent of the compound (10), preferably from 2 to 3 equivalents.

The compound (12-1) includes, for example, (2S)-2-(tetrahydro-2H-pyran-2-yloxy)propyl methanesulfonate, (2R)-2-(tetrahydro-2H-pyran-2-yloxy)propyl methanesulfonate, (1S)-2-{[tert-butyl(dimethyl)silyl]oxy}-1-methylethyl methanesulfonate.

Not specifically defined, the reaction solvent may be any one not interfering with the reaction, and includes, for example, DMSO, THF, DMF, DMA.

The reaction temperature may be generally from 20° C. to 150° C., preferably from 50° C. to 100° C.

The reaction time may be generally from 1 to 48 hours, preferably from 4 to 12 hours.

The compound (14) may also be produced through Mitsunobu reaction of the above compound (10) with a compound (12-2):

$$\text{ProO—(CH}_2)_m\text{—OH} \quad (12\text{-}2)$$

(wherein the symbols have the same meanings as above).

The reaction in this step may be attained in the same manner as in the above step 8, or according to a method similar to it, or according to a combination thereof with an ordinary method.

Thus obtained, the compound (14) may be isolated and purified in a known separation and purification method of, for example, concentration, concentration under reduced pressure, reprecipitation, solvent extraction, crystallization or chromatography, or not isolated and purified, this may be subjected to the next step.

(Step 11)

This step is a method of reacting the compound (14) with MsCl (methanesulfonyl chloride) in the presence of a base to produce a compound (15).

In place of MsCl, also usable is TsCl (p-toluenesulfonyl chloride).

The base to be used includes, for example, triethylamine, diisopropylethylamine.

The amount of the base to be used may be generally from 1 to 10 equivalents relative to 1 equivalent of the compound (14), preferably from 1 to 3 equivalents.

Not specifically defined, the reaction solvent may be any one not interfering with the reaction, and includes, for example, dichloromethane, chloroform, THF, acetonitrile, DMF, acetone, ethanol, 2-propanol.

The reaction temperature may be generally from 0° C. to the reflux temperature of the reaction solvent, preferably from 0° C. to 150° C.

The reaction time may be generally from 0.1 hours to 72 hours, preferably from 0.5 hours to 12 hours.

Thus obtained, the compound (15) may be isolated and purified in a known separation and purification method of, for example, concentration, concentration under reduced pressure, reprecipitation, solvent extraction, crystallization or chromatography, or not isolated and purified, this may be subjected to the next step.

(Step 12)

This step is a method of reacting the compound (15) with a compound (6) to produce a compound (I-1) of the invention.

The compound (6) to be used may be generally from 1 to 20 equivalents relative to 1 equivalent of the compound (15), preferably from 1 to 10 equivalents.

Not specifically defined, the reaction solvent may be any one not interfering with the reaction, and includes, for example, dichloromethane, chloroform, THF, DMF, methanol, ethanol, water The reaction temperature may be generally from 0° C. to the reflux temperature of the reaction solvent, preferably from 0° C. to 80° C.

The reaction time may be generally from 1 to 48 hours, preferably from 1 to 24 hours.

Thus obtained, the compound (I-1) of the invention may be isolated and purified in a known separation and purification method of, for example, concentration, concentration under reduced pressure, reprecipitation, solvent extraction, crystallization or chromatography.

Compounds (I-2) of the invention:

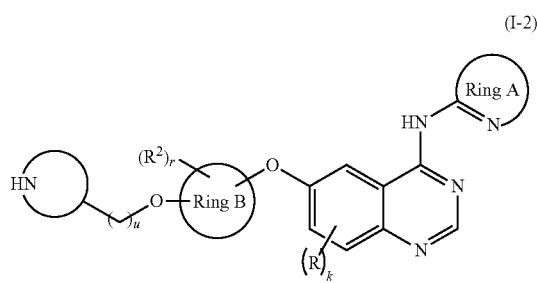

(I-2)

[wherein u indicates an integer of from 0 to 4; and the other symbols have the same meanings as above],
or compounds (I-3):

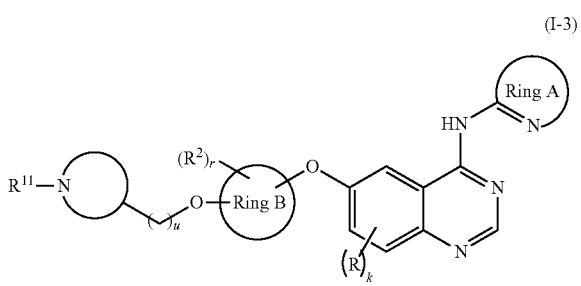

(I-3)

[wherein the symbols have the same meanings as above] can be produced, for example, according to the following method:

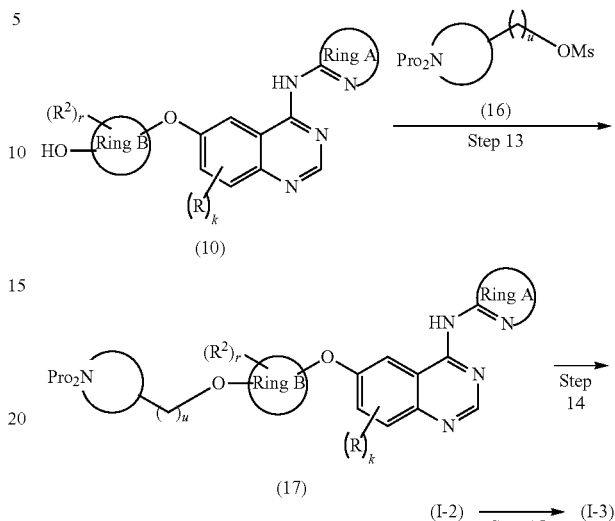

[In the formula, Pro$_2$ represents an amino-protective group; and the other symbols have the same meanings as above.]

(Step 13)

This step is a method of reacting a compound (10) with a compound (16) in the presence of a base to produce a compound (17).

The base to be used includes, for example, potassium tert-butoxide, lithium diisopropylamide, cesium carbonate, sodium hydrogencarbonate, sodium tert-pentoxide.

The amount of the base to be used may be generally from 1 to 5 equivalents relative to 1 equivalent of the compound (10), preferably from 1 to 3 equivalents.

The amino-protective group for Pro$_2$ is, for example, preferably a Boc group.

The compound (16) to be used includes concretely, for example, tert-butyl 3-[(methylsulfonyl)oxy]azetidine-1-carboxylate.

The amount of the compound (16) to be used may be generally from 0.5 to 5 equivalents relative to 1 equivalent of the compound (10), preferably from 1 to 2 equivalents.

Not specifically defined, the reaction solvent may be any one not interfering with the reaction, and includes, for example, DMA, DMF, DMSO.

The reaction temperature may be generally from 80 to 200° C.

The reaction time may be generally from 1 hour to 50 hours, preferably from 1 hour to 20 hours.

Thus obtained, the compound (17) may be isolated and purified in a known separation and purification method of, for example, concentration, concentration under reduced pressure, reprecipitation, solvent extraction, crystallization or chromatography, or not isolated and purified, this may be subjected to the next step.

(Step 14)

This step is a method of removing the amino-protective group from the compound (17) to produce a compound (I-2) of the invention. The removal of the amino-protective group may be attained in the same manner as in the method described in literature (for example, Protective Groups in Organic Synthesis, by T. W. Green, 2nd Ed., John Wiley & Sons, 1991), or in accordance with it, or by combining it with an ordinary method, thereby removing the protective group to convert the compound (17) into a compound (I-2) of the invention. For example, when the amino-protective group is a Boc group, then the compound (17) may be reacted with TFA in a solvent such as chloroform, thereby removing the protective group.

Thus obtained, the compound (I-2) of the invention may be isolated and purified in a known separation and purification method of, for example, concentration, concentration under reduced pressure, reprecipitation, solvent extraction, crystallization or chromatography.

(Step 15)

This step is a method of reacting a compound (I-2) of the invention with a corresponding aldehyde or ketone in the presence of a reducing agent, thereby producing a compound (I-3) of the invention.

The reaction in this step may be attained in the same manner as in the above step 4, or in accordance with a method similar to it, or in accordance with a combination thereof with an ordinary method.

Thus obtained, the compound (I-3) of the invention may be isolated and purified in a known separation and purification method of, for example, concentration, concentration under reduced pressure, reprecipitation, solvent extraction, crystallization or chromatography.

Compounds (I-4) of the invention:

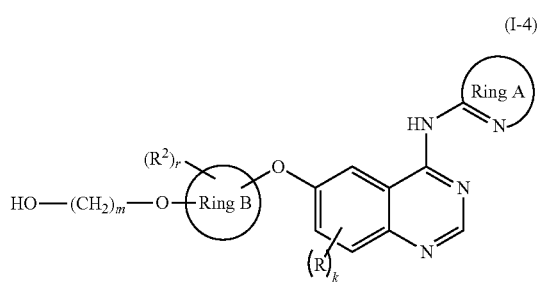

[wherein the symbols have the same meanings as above] can be produced, for example, according to the following method:

[In the formula, $X_3$ represents a leaving group; and the other symbols have the same meanings as above.]

(Step 16)

This step is a method of reacting a compound (1) with a compound (18) in the presence of a base to produce a compound (19).

The leaving group for $X_3$ is preferably a fluorine atom, a chlorine atom, a bromine atom or an iodine atom.

The compound (18) includes, for example, 5-[2-(1,3-dioxolan-2-yl)ethoxy]-2-fluoropyridine, 3-chloro-5-[2-(1,3-dioxolan-2-yl)ethoxy]-2-fluoropyridine, 5-[2-(1,3-dioxolan-2-yl)ethoxy]-2,3-difluoropyridine.

The reaction in this step may be effected in the same manner as in the above step 1 or 2, or according to a method similar to it, or according to a combination thereof with an ordinary method.

Thus obtained, the compound (19) may be isolated and purified in a known separation and purification method of, for example, concentration, concentration under reduced pressure, reprecipitation, solvent extraction, crystallization or chromatography, or not isolated and purified, this may be subjected to the next step.

(Step 17)

This step is a method of reacting the compound (19) with an acid such as TFA to produce the above compound (5).

The amount of the acid such as TFA to be used may be generally from 1 equivalent to a solvent amount relative to 1 equivalent of the compound (19), preferably from 10 to 100 equivalents.

Not specifically defined, the reaction solvent may be any one not interfering with the reaction, and includes, for example, chloroform, methylene chloride, methanol, ethanol, DMF, water or their mixed solvents.

The reaction temperature may be generally from 0° C. to 60° C., preferably from 0° C. to room temperature.

The reaction time may be generally from 1 hour to 72 hours, preferably from 1 hour to 12 hours.

Thus obtained, the compound (5) may be isolated and purified in a known separation and purification method of, for example, concentration, concentration under reduced pres-

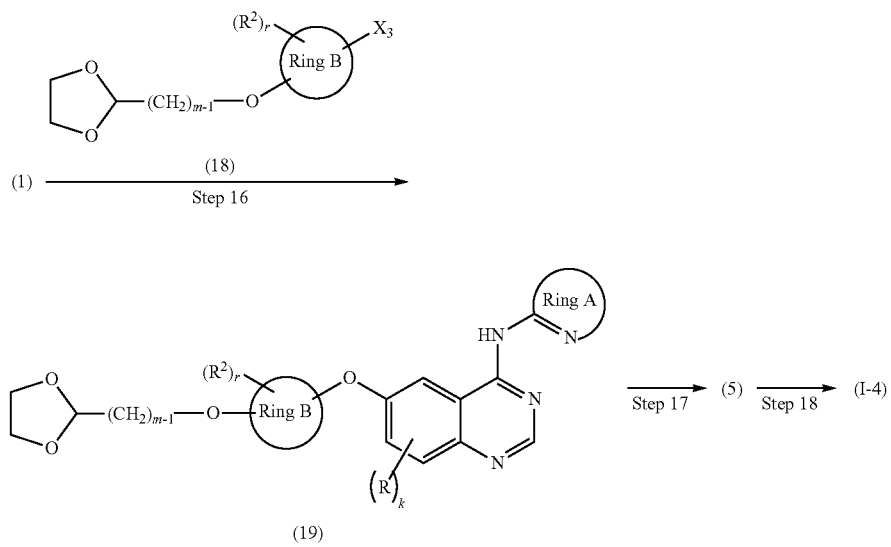

sure, reprecipitation, solvent extraction, crystallization or chromatography, or not isolated and purified, this may be subjected to the next step.
(Step 18)

This step is a method of reducing the aldehyde group that the compound (5) has, thereby producing a compound (I-4).

The reducing agent to be used includes, for example, sodium triacetoxyborohydride, sodium cyanoborohydride, sodium borohydride, lithiumaluminium hydride.

The amount of the reducing agent to be used may be generally from 0.25 to 10 equivalents relative to 1 equivalent of the compound (5), preferably from 1 to 5 equivalents.

Not specifically defined, the reaction solvent may be any one not interfering with the reaction, and includes, for example, methanol, ethanol, chloroform, methylene chloride, THF or their mixed solvents.

The reaction temperature may be generally from 0° C. to 60° C., preferably from 0° C. to room temperature.

The reaction time may be generally from 0.5 to 10 hours, preferably from 0.5 to 5 hours.

Thus obtained, the compound (I-4) may be isolated and purified in a known separation and purification method of, for example, concentration, concentration under reduced pressure, reprecipitation, solvent extraction, crystallization or chromatography.

Compounds (I-5) of the invention:

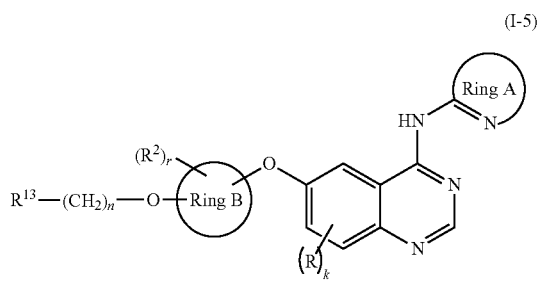

[wherein the symbols have the same meanings as above] can be produced, for example, according to the following method:

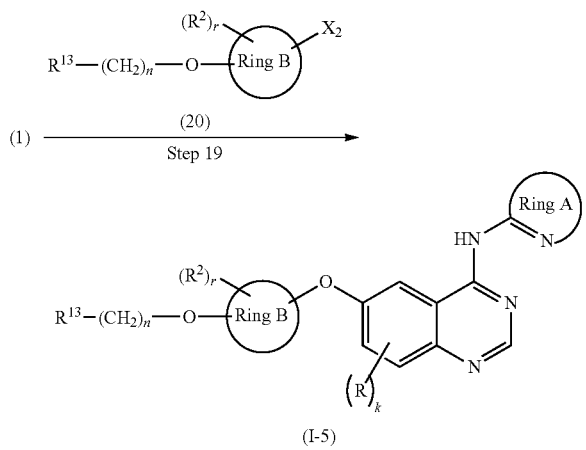

[In the formula, $X_2$ represents a leaving group; and the other symbols have the same meanings as above.]
(Step 19)

This step is a method of reacting a compound (1) with a compound (20) in the presence of a base to produce a compound (I-5) of the invention.

The reaction in this step may be attained in the same manner as in the above step 1 or 2, or according to a method similar to it, or according to a combination thereof with an ordinary method.

The leaving group for $X_2$ includes, for example, a halogen atom, a methanesulfonyloxy group, a p-toluenesulfonyloxy group.

The compound (20) includes, for example, 2,3-dichloro-5-(2-methoxyethoxy)pyridine.

When $R_{13}$ is a hydroxyl group or a carboxyl group, it may be suitably protected or deprotected. The introduction or removal of the protective group may be attained in the same manner as in the method described in literature (for example, Protective Groups in Organic Synthesis, by T. W. Green, 2nd Ed., John Wiley & Sons, 1991), or in accordance with it, or by combining it with an ordinary method.

Thus obtained, the compound (I-5) of the invention may be isolated and purified in a known separation and purification method of, for example, concentration, concentration under reduced pressure, reprecipitation, solvent extraction, crystallization or chromatography.

Compounds (I-6) of the invention:

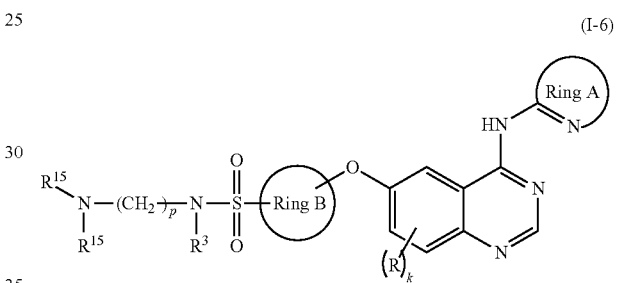

[wherein the symbols have the same meanings as above] can be produced according to the following method:

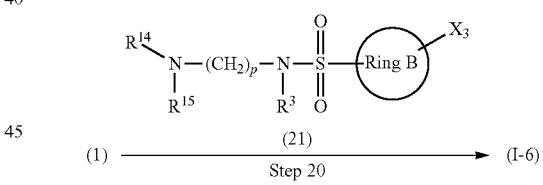

[In the formula, $X_3$ represents a leaving group, and the other symbols have the same meanings as above.]
(Step 20)

This step is a method of reacting a compound (1) with a compound (21) in the presence of a base to produce a compound (I-6) of the invention.

The compound (21) to be used includes, for example, 5,6-dichloro-N-[2-(dimethylamino)ethyl]-N-methylpyridine-3-sulfonamide, 5,6-dichloro-N-[3-(dimethylamino)propyl]-N-methylpyridine-3-sulfonamide.

The reaction in this step may be attained in the same manner as in the above step 1 or 2, or according to a method similar to it, or according to a combination thereof with an ordinary method.

Thus obtained, the compound (I-6) of the invention may be isolated and purified in a known separation and purification method of, for example, concentration, concentration under reduced pressure, reprecipitation, solvent extraction, crystallization or chromatography.

Compounds (I-7) of the invention:

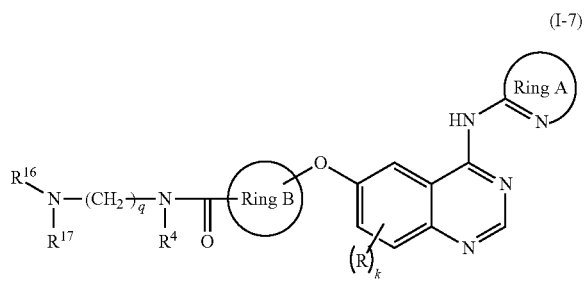

(I-7)

[wherein the symbols have the same meanings as above] can be produced according to the following method:

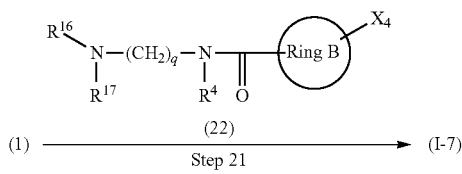

(1) $\xrightarrow[\text{Step 21}]{(22)}$ (I-7)

[In the formula, $X_4$ represents a leaving group, and the other symbols have the same meanings as above.]

(Step 21)

This step is a method of reacting a compound (1) with a compound (22) in the presence of a base to produce a compound (I-7) of the invention.

The compound (22) to be used includes, for example, 5,6-dichloro-N-[2-(dimethylamino)ethyl]-N-methylnicotinamide, 5,6-dichloro-N-methyl-N-(2-pyrrolidin-1-ylethyl)nicotinamide, 3-chloro-N-[2-(dimethylamino)ethyl]-2-fluoro-N-methylisonicotinamide, 5,6-dichloro-N-[3-(dimethylamino)propyl]-N-methylnicotinamide.

The reaction in this step may be attained in the same manner as in the above step 1 or 2, or according to a method similar to it, or according to a combination thereof with an ordinary method.

Thus obtained, the compound (I-7) of the invention may be isolated and purified in a known separation and purification method of, for example, concentration, concentration under reduced pressure, reprecipitation, solvent extraction, crystallization or chromatography.

In the above-mentioned reaction, the protective group may be introduced or removed in any desired manner. Concretely, the introduction or removal of the protective group may be attained in the same manner as in the method described in literature (for example, Protective Groups in Organic Synthesis, by T. W. Green, 2nd Ed., John Wiley & Sons, 1991), or in accordance with it, or by combining it with an ordinary method.

The heteroaryloxyquinazoline derivatives that the invention provides may exist as their pharmaceutically-acceptable salts, and the salts can be produced from the compounds (I) and the compounds of the above-mentioned formula (I-1), (I-2), (I-3), (I-4), (I-5), (I-6) or (I-7) falling within the scope of the compounds (I) of the invention in an ordinary manner.

Concretely, when the compounds of formula (I), (I-1), (I-2), (I-3), (I-4), (I-5), (I-6) or (I-7) have a basic group derived from, for example, an amino group or a pyridyl group in the molecule, then the compounds may be processed with acid so as to convert them into the corresponding pharmaceutically-acceptable salts.

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates. When the compounds of the invention have an acid group in the molecule, for example, when they have a carboxyl group, then the compounds may be processed with a base so as to convert them into the corresponding pharmaceutically-acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc. In addition, the compounds of the invention may also be in any other form of hydrates or solvates of their free compounds or their salts.

Depending on the type of the substituents therein, the compounds of the invention include stereoisomers and tautomers such as optical isomers, diastereomeric isomers and geometrical isomers. Needless-to-say, the compounds of the invention include all these isomers. Further needless-to-say, the compounds of the invention include all mixtures of such isomers.

In producing medicines for prevention and remedy for type II diabetes or diseases or symptoms associated with it, the compounds of formula (I) of the invention may be combined with carrier substances.

The dose of the compounds of formula (I) of the invention for prevention or remedy for diseases naturally varies, depending on the property of the symptom to which the treatment is directed, the specific compound selected for it and the administration route.

In addition, the dose also varies depending on the age, the body weight and the sensitivity of patients. In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 mg. More preferably, the daily dose is from about 10 mg to 100 mg for one-time administration a day.

For intravenous administration or oral administration, a typical dose of the compound (I) may be from about 0.001 mg/day/kg-body weight to about 100 mg/day/kg-body weight (preferably from 0.01 mg/day/kg-body weight to about 10 mg/day/kg-body weight), more preferably from about 0.1 mg/day/kg-body weight to 10 mg/day/kg-body weight.

As so mentioned hereinabove, the pharmaceutical composition of the invention comprises a compound of formula (I) and a pharmaceutically-acceptable carrier. The term "composition" is meant to contain not only a product produced by directly or indirectly combining, hybridizing or aggregating 2 or more ingredients, a product produced as a result of dissociation of one or more ingredients, or a compound produced as a result of reaction or interaction of different types of ingredients, but also an active and inactive ingredient of constituting a carrier (pharmaceutically-acceptable vehicle).

As combined with a pharmaceutically-acceptable carrier, the composition of the invention preferably contains a compound of formula (I) in an amount effective for remedy and prevention of type II diabetes and for retardation of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil, alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administration, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cashews and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets can be produced by mixing the active ingredient optionally with binder, lubricant, inert vehicle, surfactant or dispersant and compressing the resulting mix in any desired manner into powders or granules.

Shaped tablets may be prepared by shaping a mixture of a powdery wet compound and an inert liquid diluent, using a suitable machine.

Preferably, the tablets each contain from about 1 mg to 1 g of the active ingredient; and the cashews and the capsules each contain from about 1 mg to 500 mg of the active ingredient.

Examples of the administration modes of the compounds of formula (I) for pharmaceutical use are as follows:

TABLE 1

| Suspension for Injection (I.M.) | mg/ml |
|---|---|
| compound of formula (I) | 10 |
| methyl cellulose | 5.0 |
| Tween 80 | 0.5 |
| benzyl alcohol | 9.0 |
| benzalkonium chloride | 1.0 |
| water for injection added to make 1.0 ml | |

TABLE 2

| Tablets | mg/tablet |
|---|---|
| compound of formula (I) | 25 |
| methyl cellulose | 415 |
| Tween 80 | 14.0 |
| benzyl alcohol | 43.5 |
| magnesium stearate | 2.5 |
| total | 500 mg |

TABLE 3

| Capsules | mg/capsule |
|---|---|
| compound of formula (I) | 25 |
| lactose powder | 573.5 |
| magnesium stearate | 1.5 |
| total | 600 mg |

TABLE 4

| Aerosol | per one container |
|---|---|
| compound of formula (I) | 24 mg |
| lecithin, NF Liq. Conc. | 1.2 mg |
| trichlorofluoromethane, NF | 4.025 g |
| dichlorodifluoromethane, NF | 12.15 g |

The compounds of the formula (I) may be used, as combined with any other drugs usable not only for type II diabetes-associated diseases or symptoms but also for remedy/prevention/retardation of the onset of type II diabetes. The additional drugs may be administered in any administration route and dose generally employed in the art, simultaneously with or separately from the compound of the formula (I).

In case where the compound of the formula (I) is used along with one or more other drugs, then a pharmaceutical composition comprising the compound of the formula (I) and the additional drug is preferred. Accordingly, the pharmaceutical composition of the invention may comprise not only the compound of the formula (I) but also one or more such active ingredients. Examples of the active ingredients that may be combined with the compounds of the formula (I) are mentioned below, which, however, are not limitative. These may be separately administered or may be administered simultaneously as contained in the same pharmaceutical composition.

(a) other glucokinase activators,
(b) bis-guanides (e.g., buformin, metoformin, fenformin,),
(c) PPAR agonists (e.g., triglytazon, pioglytazon, nosiglytazon),
(d) insulin, (e) somatostatin,
(f) α-glucosidase inhibitors (e.g., boglybose, miglytol, acarbose),
(g) insulin secretion promoters (e.g., acetohexamide, calbutamide, chlorpropamide, glybomlide, glycrazide, glymerpiride, glypidide, glyquidine, glysoxepide, glyburide, glyhexamide, glypinamide, fenbutamide, trazamide, tolbutamide, tolcyclamide, nateglynide, repaglynide),
(h) DPP-IV (dipeptidyl peptidase IV) inhibitors, and
(i) glucose intake promoters.

The weight ratio of the compound of the formula (I) to the second active ingredient may vary within a broad range, and depends on the effective amount of the individual active ingredients. Accordingly, for example, when the compound of the formula (I) is combined with a PPAR agonist, then the weight ratio of the compound of the formula (I) to the PPAR agonist may be generally from about 1000/1 to 1/1000, preferably from about 200/1 to 1/200. The combination of the compound of the formula (I) and the other active ingredient may be within the above-mentioned range. In any case, an effective amount of the individual ingredients should be in the combination.

The glucokinase-activating potency of the compounds of the formula (I) of the invention and the blood pressure-depressing potency thereof based on it are verified, for example, by the following pharmacological experiments mentioned below.

Pharmacological Experiment 1 (Glucokinase-Activating Effect)

The glucokinase-activating potency of the compounds of the formula (I) of the invention and a test method for it are described below.

The excellent glucokinase-activating effect of the compounds of the formula (I) may be determined by a method described in literature (for example, Diabetes, Vol. 45, pp. 1671-1677, 1996), or in accordance with it.

The glucokinase activity may be determined not by directly measuring glucose-6-phosphate but by measuring the level of Thio-NADH, which is produced when a reporter enzyme, glucose-6-phosphate dehydrogenase produces phosphoglu-conolactone from glucose-6-phosphate, and based on the level, the degree of glucokinase activation by the compound tested may be determined In this assay, used was a recombinant human liver GK, which was expressed by $E.$ $coli$ as a FLAG fusion protein therein and was purified by ANTIFLAG M2 AFFINITY GEL (Sigma).

Using a flat-bottomed 96-well plate, the assay was carried out at 30° C. 69 μl of an assay buffer (25 mM Hepes Buffer/pH=7.2, 2 mM $MgCl_2$, 1 mM ATP, 0.5 mM TNAD, 1 mM dithiothreitol) was put into the plate, and 1 μl of a DMSO solution of the compound or DMSO alone as a control was added thereto. Next, 20 μl of an enzyme mixture (FLAG-GK, 20 U/ml G6PDH) cooled in ice was added to it, and 10 μl of a substrate, 25 mM glucose was added to it, and the reaction was initiated (final glucose concentration=2.5 mM).

After the start of the reaction, the increase in the absorbance at 405 nm was measured for 12 minutes at intervals of 30 seconds, and the increase for the first 5 minutes was used for assessing the compound tested. FLAG-GK was added so that the absorbance increase after 5 minutes in the presence of 1% DMSO could be from 0.04 to 0.06.

The OD level of the DMSO control was set as 100%; and the OD level of the test compound at different concentrations was determined. From the OD level at each concentration, Emax (%) and EC50 (μM) were computed and used as the index of the GK-activating potency of the compound.

The GK activity of the compound of the present invention was measured according to the method. The result are shown in table 5.

TABLE 5

| example | Emax (%) | EC50 (μM) |
|---|---|---|
| example 1 | 1322 | 0.08 |
| example 2 | 1587 | 0.42 |
| example 3 | 918 | 1.74 |
| example 4 | 1659 | 0.38 |
| example 5 | 1838 | 0.26 |
| example 7 | 695 | 6.93 |
| example 8 | 1067 | 1.32 |
| example 18 | 1583 | 0.03 |
| example 20 | 1338 | 0.04 |
| example 23 | 1013 | 0.05 |
| example 25 | 1308 | 0.23 |
| example 31 | 1464 | 0.44 |
| example 32 | 1314 | 0.04 |
| example 34 | 1103 | 0.07 |
| example 35 | 1379 | 0.1 |
| example 37 | 1356 | 0.38 |
| example 40 | 1503 | 0.35 |
| example 44 | 1530 | 0.26 |
| example 46 | 1080 | 0.11 |
| example 47 | 1198 | 0.29 |
| example 54 | 1409 | 0.36 |
| example 58 | 1284 | 0.2 |
| example 61 | 888 | 0.41 |
| example 64 | 1174 | 1.14 |
| example 65 | 1232 | 0.41 |
| example 67 | 598 | 6.09 |
| example 70 | 979 | 0.026 |
| example 76 | 1354 | 0.23 |
| example 81 | 1216 | 0.013 |
| example 84 | 1414 | 0.04 |

The compounds of the present invention have excellent GK activity as the index of the Emax (%) and EC50 (μM) value as shown in above table.

comparative Test

The compounds of the present invention improved the pharmacological activity compared with the compounds described in the patent document 1. The comparative test was conducted to compare the compound of example 18, 31 and 32 in this invention with the compound (A) in the patent document 1. The test method in vitro was similar to pharmacological experiment 1 (glucokinase-activating effect).

GK activity EC50 (mM) of the compound of example 18, 31 and 32 in this invention and the compound (A) in the patent document 1 are 0.03, 0.44, 0.04 and 0.21 respectively.

The test method in vivo is shown as follow.

Pharmacological Test Example 2 (Drug Efficacy Test in Dogs)

From the cephalic vein of male beagles fasted overnight (10.4-13.7 kg body weight), blood was collected prior to administration, followed by oral administration of the test drug suspended in a 0.5% methyl cellulose solution (1 mg/kg in both of the compounds of Example A and Example 18), while a 0.5% methyl cellulose solution was orally administered to the control group. The blood was collected every 0.5 or 1 hour after the administration of the test drug. Plasma was separated from the obtained blood to determine a plasma glucose level using Determina-GL-E (Kyowa Medics). Percentage reductions in plasma glucose level AUC compared to the control group up to 4 hours after the administration were described below.

TABLE 6

| Example No. | Dose (mg/kg) | Percentage reduction (%) in plasma glucose level AUC |
|---|---|---|
| Example 18 | 1 | 26 |
| Compound A | 1 | −1 |

Pharmacological Test Example 3 (Drug Efficacy Test in Dogs)

From the cephalic vein of male beagles fasted overnight (8.5-13.7 kg body weight), blood was collected prior to administration, followed by oral administration of the test drug suspended in a 0.5% methyl cellulose solution (1 mg/kg in both of Examples 30 and 31), while a 0.5% methyl cellulose solution was orally administered to the control group. The blood was collected every 0.5 or 1 hour after the administration of the test drug. Plasma was separated from the obtained blood to determine a plasma glucose level using Determina-GL-E (Kyowa Medics).

Percentage reductions in plasma glucose level AUC compared to the control group up to 4 hours after the administration were described below.

TABLE 7

| Example No. | Dose (mg/kg) | Percentage reduction (%) in plasma glucose level AUC |
|---|---|---|
| Example 31 | 1 | 7.9 |
| Example 32 | 1 | 17.5 |
| Compound A | 1 | −1 |

As shown above, the compounds according to the present invention were greatly improved in pharmacological activity compared to the compound according to the patent document. Particularly, the in vivo tests exhibited that the compounds according to the present invention showed excellent drug efficacy whereas the compound (A) showed no drug efficacy in the dogs.

EXAMPLES

The invention is described more concretely with reference to the following Preparation Examples, Examples and Reference Examples, by which, however, the invention should not be limited at all.

In Examples, Silicagel 60F$_{245}$ (Merck) was used for the plate in thin-layer chromatography, PLC05 NH (FUJI Silysia) was used for the plate in amine-type thin-layer chromatography, and a UV detector was used for detection. For the column silica gel, used was Wakogel™ C-300 (Wako Pure Chemical); and for the reversed-phase column silica gel, used was LC-SORB™ SP-B-ODS (Chemco) or YMC-GEL™ ODS-AQ 120-S50 (Yamamura Chemical Laboratory).

The meanings of the abbreviations in the following Examples are shown below.
i-Bu: isobutyl
n-Bu: n-butyl
t-Bu: t-butyl
Me: methyl
Et: ethyl
Ph: phenyl
i-Pr: isopropyl
n-Pr: n-propyl
CDCl$_3$: heavy chloroform
CD$_3$OD: heavy methanol
DMSO-d$_6$: heavy dimethylsulfoxide The meanings of the abbreviations in the following nuclear magnetic resonance spectra are shown below.
s: singlet
d: doublet
dd: double-doublet
t: triplet
m: multiplet
br: broad
brs: broad singlet
q: quartet
J: coupling constant
Hz: hertz Example 1

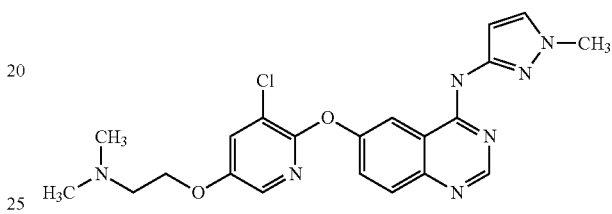

Preparation of 6-({3-chloro-5-[2-(dimethylamino)ethoxy]pyridin-2-yl}oxy)-N-(1-methyl-1H-pyrazol-3-yl)quinazoline-4-amine 1) 2,3-Dichloro-5-(2,2-diethoxyethoxy)pyridine (641 mg, 2.29 mmol) and potassium tert-butoxide (279 mg, 2.49 mmol) were added to an N,N-dimethylacetamide solution (3 ml) of 4-[(1-methyl-1H-pyrazol-3-yl)amino]quinazolin-6-ol (240 mg, 1.00 mmol), and stirred at 170° C. for 14 hours under a nitrogen atmosphere in a sealed tube. The reaction solution was cooled with ice, then saline water and chloroform were added, the organic layer was washed with water, dried over anhydrous magnesium sulfate, and concentrated under reduced pressure. The obtained residue was purified by reversed-phase liquid chromatography (YMC CombiPrep Pro C18 AS-360-CC) to obtain 6-{[3-chloro-5-(2,2-diethoxyethyl)pyridin-2-yl]oxy}-N-(1-methyl-1H-pyrazol-3-yl)quinazoline-4-amine (217 mg, yield: 45%) as an orange oil and 6-{[2-chloro-5-(2,2-diethoxyethoxy)pyridin-3-yl]oxy}-N-(1-methyl-1H-pyrazol-3-yl)quinazoline-4-amine (136 mg, yield: 28%) as an orange oil.

2) A chloroform (3 ml) solution of 6-{[3-chloro-5-(2,2-diethoxyethyl)pyridin-2-yl]oxy}-N-(1-methyl-1H-pyrazol-3-yl)quinazoline-4-amine (210 mg, 0.35 mmol) obtained in the above reaction was added to a mixed solution of trifluoroacetic acid (3 ml) and water (0.5 ml) cooled with ice, and stirred at room temperature for 4 hours. With cooling with ice, aqueous saturated sodium hydrogencarbonate solution was added to the reaction solution, and extracted with chloroform/methanol (9:1). The organic layer was dried over anhydrous sodium sulfate, and concentrated under reduced pressure to obtain a crude product (135 mg) containing {[5-chloro-6-({4-[(1-methyl-1H-pyrazol-3-yl)amino]quinazolin-6-yl}oxy)pyridin-3-yl]oxy}acetaldehyde as a pale orange amorphous solid.

3) 2 M dimethylamine/tetrahydrofuran solution (0.11 ml, 0.21 mmol) was added to a tetrahydrofuran solution (2 ml) of the crude aldehyde product (58 mg, 0.14 mmol) obtained in the above reaction, and stirred under a nitrogen atmosphere at room temperature for 10 minutes, then sodium triacetoxyborohydride (90 mg, 0.42 mmol) was added, and the reaction solution was further stirred at room temperature for 20 minutes. Saturated saline water was added to the reaction solution, extracted with chloroform/methanol (9:1), the organic layer was dried over anhydrous sodium sulfate and concentrated under reduced pressure. The obtained residue was purified by amine-type silica gel column chromatography (Biotage NH, hexane:ethyl acetate:chloroform to ethyl acetate:chloroform=2:6:1 to 5:1) to obtain the entitled compound (42 mg, yield: 68%) as a white amorphous solid.

The analytical data of the entitled compound are shown below.

$^1$H-NMR (DMSO-$d_6$) δ: 2.21 (6H, s), 2.62 (2H, t, J=5.6 Hz), 3.80 (3H, s), 4.14 (2H, t, J=5.6 Hz), 6.79 (1H, d, J=2.0 Hz), 7.62-7.65 (2H, m), 7.81 (1H, d, J=9.3 Hz), 7.89 (1H, d, J=2.9 Hz), 7.91 (1H, d, J=2.9 Hz), 8.33 (1H, d, J=2.4 Hz), 8.57 (1H, s), 10.29 (1H, s).

ESI-MS (m/e): 440 [M+H]$^+$

Preparation of 2,3-dichloro-5-(2,2-diethoxyethoxy)pyridine

Bromoacetaldehyde diethyl acetal (2.74 ml, 18.3 mmol) and cesium carbonate (9.93 g, 30.5 mmol) were added to an N,N-dimethylacetamide solution (10 ml) of 5,6-dichloropyridin-3-ol (1.0 g, 6.10 mmol), and stirred under a nitrogen atmosphere at 100° C. for 16 hours. Saline solution and ethyl acetate were added to the reaction solution, the organic layer was washed with water, dried over anhydrous sodium sulfate, and concentrated under reduced pressure. The obtained residue was purified by silica gel column chromatography (Biotage, hexane:ethyl acetate=11:1 to 9:1) to obtain 2,3-dichloro-5-(2,2-diethoxyethoxy)pyridine (1.51 g, yield: 88%) as an orange oil.

Example 2

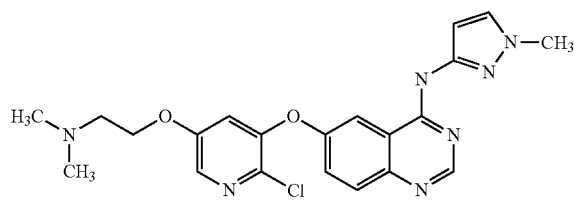

Preparation of 6-({2-chloro-5-[2-(dimethylamino) ethoxy]pyridin-3-yl}oxy)-N-(1-methyl-1H-pyrazol-3-yl)quinazoline-4-amine 1) A chloroform (2 ml) solution of 6-{[2-chloro-5-(2,2-diethoxyethoxy)pyridin-3-yl]oxy}-N-(1-methyl-1H-pyrazol-3-yl)quinazoline-4-amine (132 mg, 0.27 mmol) obtained in Example 1 was added to a mixed solution of trifluoroacetic acid (2 ml) and water (0.2 ml) cooled with ice, and stirred at room temperature for 2 hours. With cooling with ice, aqueous saturated sodium hydrogencarbonate solution was added to the reaction solution, and extracted with chloroform/methanol (9:1). The organic layer was dried over anhydrous sodium sulfate, and concentrated under reduced pressure to obtain a crude product (144 mg) containing {[6-chloro-5-({4-[(1-methyl-1H-pyrazol-3-yl)amino]quinazolin-6-yl}oxy)pyridin-3-yl]oxy}acetaldehyde as a pale orange amorphous solid.

2) 2 M dimethylamine/tetrahydrofuran solution (0.10 ml, 0.19 mmol) was added to a tetrahydrofuran solution (2 ml) of the crude aldehyde product (68 mg) obtained in the above reaction, and stirred under a nitrogen atmosphere at room temperature for 10 minutes, then sodium triacetoxyborohydride (82 mg, 0.39 mmol) was added, and the reaction solution was further stirred at room temperature for 20 minutes. Saturated saline water was added to the reaction solution, extracted with chloroform/methanol (9:1), the organic layer was dried over anhydrous sodium sulfate and concentrated under reduced pressure. The obtained residue was purified by amine-type silica gel column chromatography (Biotage NH, hexane:ethyl acetate to hexane:ethyl acetate:chloroform=2:3 to 2:6:1) to obtain the entitled compound (41 mg, yield: 72%, 2 steps from 1)) as a yellow white solid.

The analytical data of the entitled compound are shown below.

$^1$H-NMR (DMSO-$d_6$) δ: 2.15 (6H, s), 2.58 (2H, t, J=5.6 Hz), 3.79 (3H, s), 4.11 (2H, t, J=5.6 Hz), 6.77 (1H, d, J=2.0 Hz), 7.41 (1H, d, J=2.4 Hz), 7.64-7.69 (2H, m), 7.84 (1H, d, J=8.8 Hz), 8.08 (1H, d, J=2.9 Hz), 8.13 (1H, d, J=2.4 Hz), 8.56 (1H, s), 10.33 (1H, s).

ESI-MS (m/e): 440 [M+H]$^+$

Example 3

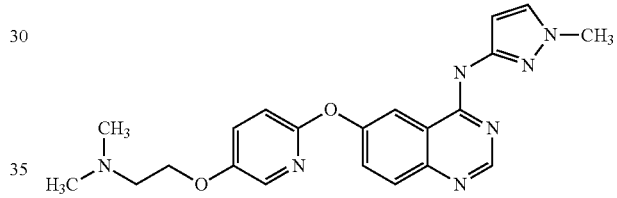

Preparation of 6-({6-[2-(dimethylamino)ethoxy] pyridin-3-yl}oxy)-N-(1-methyl-1H-pyrazol-3-yl) quinazoline-4-amine 1) 5-Bromo-2-nitropyridine (460 mg, 2.3 mmol) and sodium hydride (120 mg, 3.1 mmol) were added to an N,N-dimethylformamide suspension (10 ml) of 4-[(1-methyl-1H-pyrazol-3-yl)amino]quinazolin-6-ol (500 mg, 2.1 mmol), and stirred at 60° C. for 14 hours. The reaction solution was cooled to room temperature, the precipitate was collected by filtration, washed with water. The obtained precipitate was dried, then purified by silica gel column chromatography (chloroform:methanol=96:4) to obtain N-(1-methyl-1H-pyrazol-3-yl)-6-[(6-nitropyridin-3-yl)oxy]quinazoline-4-amine (580 mg, yield: 77%) as a pale yellow solid.

2) Iron powder (880 mg, 16 mmol) and ammonium chloride (420 mg, 7.8 mmol) were added to a tetrahydrofuran/methanol/water mixed solution (9 ml/3 ml/3 ml) of the nitropyridine product (570 mg, 1.6 mmol) obtained in the above reaction, and the reaction solution was stirred at 80° C. for 30 minutes. The reaction solution was cooled to room temperature, and the precipitate was separated by filtration followed by concentration under reduced pressure. The obtained residue was dissolved in chloroform, then the organic layer was washed with aqueous saturated sodium hydrogencarbonate solution and saturated saline water, dried over anhydrous sodium sulfate, and concentrated under reduced pressure. The obtained residue was purified by silica gel column chromatography (chloroform:methanol=94:6) to obtain a crude product (580 mg) containing 6-[(6-aminopyridin-3-yl)oxy]-N-(1-methyl-1H-pyrazol-3-yl)quinazoline-4-amine as a pale yellow solid.

3) With cooling with ice, aqueous 5.7 M sodium nitrite solution (0.3 ml, 1.7 mmol) was added to a concentrated sulfuric acid solution (6 ml) of the crude aminopyridine product (580 mg) obtained in the above reaction. The reaction solution was stirred at room temperature for 30 minutes. With cooling with ice, water (10 ml) was added to the reaction solution, then neutralized with potassium carbonate added, and extracted with a mixed solution of chloroform/methanol (5:1). The organic layer was washed with saturated saline water, dried over anhydrous sodium sulfate, and concentrated under reduced pressure. The obtained residue was purified by silica gel column chromatography (chloroform:methanol=90:10) to obtain 5-({4-[(1-methyl-1H-pyrazol-3-yl)amino]quinazolin-6-yl}oxy)pyridin-2-ol (360 mg, yield: 70%) as a pale yellow solid.

4) 2-(Dimethylamino)ethanol (20 mg, 0.22 mmol), triphenyl phosphine (59 mg, 0.22 mmol) and diethyl azodicarboxylate (0.036 ml, 0.22 mmol) were added to a tetrahydrofuran solution (2 ml) of the alcohol product (50 mg, 0.15 mmol) obtained in the above reaction, and the reaction solution was stirred at room temperature for 18 hours. The reaction solution was diluted with chloroform, the organic layer was washed with water and saturated saline water, dried over anhydrous sodium sulfate, and concentrated under reduced pressure. The obtained residue was purified by silica gel column chromatography (chloroform:methanol=98:2) to obtain the entitled compound (46 mg, yield: 76%) as a pale brown oil.

The analytical data of the entitled compound are shown below.

¹HNMR (DMSO-d6) δ: 2.21 (s, 6H), 2.62 (t, 2H, J=5.9 Hz), 3.78 (s, 3H), 4.33 (t, 2H, J=5.9 Hz), 6.76 (d, 1H, J=2.2 Hz), 6.89 (d, 1H, J=8.3 Hz), 7.55-7.64 (m, 3H), 7.78 (d, 1H, J=9.0 Hz), 8.09-8.07 (m, 2H), 8.51 (s, 1H), 10.31 (s, 1H)

ESI-MS (m/e): 406 [M+H]⁺

Example 4

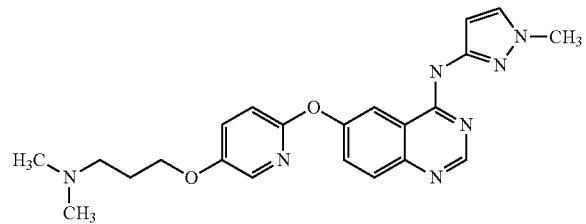

Preparation of 6-({5-[3-(dimethylamino)propoxy]pyridin-2-yl}oxy)-N-(1-methyl-1H-pyrazol-3-yl)quinazoline-4-amine 1) 2-Fluoro-5-[3-(tetrahydro-2H-pyran-2-yloxy)propoxy]pyridine (305 mg, 1.10 mmol) and potassium tert-butoxide (140 mg, 1.24 mmol) were added to an N,N-dimethylacetamide solution (1 ml) of 4-[(1-methyl-1H-pyrazol-3-yl)amino]quinazolin-6-ol (120 mg, 0.50 mmol), and stirred at 180° C. for 14 hours under a nitrogen atmosphere in a sealed tube. The reaction solution was cooled with ice, then saline water was added, and extracted with chloroform. The organic layer was washed with water, dried over anhydrous magnesium sulfate, and concentrated under reduced pressure. The obtained residue was purified by silica gel column chromatography (Biotage, chloroform:methanol=100:3) to obtain N-(1-methyl-1H-pyrazol-3-yl)-6-({5-[3-(tetrahydro-2H-pyran-2-yloxy)propoxy]pyridin-2-yl}oxy)quinazoline-4-amine (230 mg, yield: 97%) as a pale orange amorphous solid.

2) Pyridinium p-toluenesulfonate (243 mg, 0.97 mmol) was added to an ethanol solution (2 ml) of N-(1-methyl-1H-pyrazol-3-yl)-6-({5-[3-(tetrahydro-2H-pyran-2-yloxy)propoxy]pyridin-2-yl}oxy)quinazoline-4-amine (230 mg, 0.48 mmol) obtained in the above reaction, and stirred under reflux for 2 hours. The reaction solution was cooled to room temperature, saline water was added, and extracted with chloroform/methanol (9:1), the organic layer was dried over anhydrous sodium sulfate, and concentrated under reduced pressure. The obtained residue was purified by silica gel column chromatography (Biotage, chloroform:methanol=100:5) to obtain 3-{[6-({4-[(1-methyl-1H-pyrazol-3-yl)amino]quinazolin-6-yl}oxy)pyridin-3-yl]oxy}propan-1-ol (131 mg, yield: 69%) as a pale yellow amorphous solid.

3) With cooling with ice, triethylamine (0.13 ml, 0.89 mmol) and methanesulfonyl chloride (0.046 ml, 0.60 mmol) were added to a chloroform solution (3 ml) of the hydroxy product (117 mg, 0.30 mmol) obtained in the above reaction, and the reaction solution was stirred for 20 minutes. Water was added to the reaction solution, extracted with chloroform, the organic layer was dried over anhydrous sodium sulfate, and concentrated under reduced pressure to obtain a crude product (283 mg) containing 3-{[6-({4-[(1-methyl-1H-pyrazol-3-yl)amino]quinazolin-6-yl}oxy)pyridin-3-yl]oxy}propyl methanesulfonate as a pale orange oil.

4) 2 M dimethylamine/tetrahydrofuran solution (4 ml, 8.00 mmol) was added to a tetrahydrofuran solution (1 ml) of the crude methanesulfonate product (283 mg) obtained in the above reaction, and stirred under a nitrogen atmosphere at 55° C. for 16 hours. Saturated saline water was added to the reaction solution, extracted with chloroform/methanol (9:1), the organic layer was dried over anhydrous sodium sulfate, and concentrated under reduced pressure. The obtained residue was purified by amine-type silica gel column chromatography (Biotage NH, hexane:ethyl acetate to ethyl acetate:methanol=1:2 to 100:2) to obtain the entitled compound (96 mg, yield: 77%, 2 steps from 3)) as a yellow amorphous solid.

The analytical data of the entitled compound are shown below.

¹H-NMR (DMSO-d₆) δ: 1.81-1.88 (2H, m), 2.14 (6H, s), 2.35 (2H, t, J=7.1 Hz), 3.80 (3H, s), 4.05 (2H, t, J=6.3 Hz), 6.79 (1H, d, J=2.0 Hz), 7.11 (1H, d, J=8.8 Hz), 7.54-7.60 (2H, m), 7.65 (1H, d, J=2.4 Hz), 7.79 (1H, d, J=8.8 Hz), 7.90 (1H, d, J=3.4 Hz), 8.34 (1H, d, J=2.4 Hz), 8.56 (1H, s), 10.30 (1H, s).

ESI-MS (m/e): 420 [M+H]⁺

Preparation of 2-fluoro-5-[3-(tetrahydro-2H-pyran-2-yloxy)propoxy]pyridine

Bromoacetaldehyde diethyl acetal (2.29 ml, 13.3 mmol) and cesium carbonate (10.08 g, 30.9 mmol) were added to an N,N-dimethylacetamide solution (20 ml) of 6-fluoropyridin-3-ol (1 g, 8.84 mmol), and stirred under a nitrogen atmosphere at 100° C. for 6 hours. The reaction solution was cooled to room temperature, water was added, and extracted with ethyl acetate. The organic layer was washed with water and saturated saline water, dried over anhydrous sodium sulfate, and concentrated under reduced pressure. The obtained residue was purified by silica gel column chromatography

Example 5

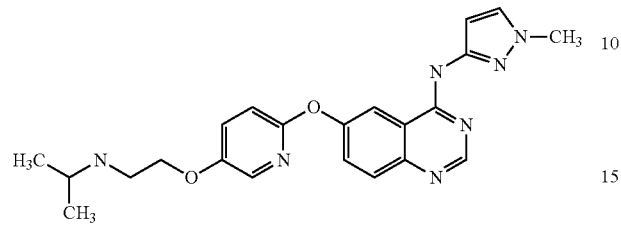

Preparation of 6-({5-[2-(isopropylamino)ethoxy]pyridin-2-yl}oxy)-N-(1-methyl-1H-pyrazol-3-yl)quinazoline-4-amine 1) 5-(2,2-diethoxyethoxy)-2-fluoropyridine (502 mg, 2.19 mmol) and potassium tert-butoxide (279 mg, 2.49 mmol) were added to an N,N-dimethylacetamide solution (1 ml) of 4-[(1-methyl-1H-pyrazol-3-yl)amino]quinazolin-6-ol (240 mg, 1.00 mmol), and stirred at 170° C. for 15 hours under a nitrogen atmosphere in a sealed tube. The reaction solution was cooled to room temperature, then water was added, and extracted with chloroform. The organic layer was washed with water, dried over anhydrous sodium sulfate, and concentrated under reduced pressure. The obtained residue was purified by silica gel column chromatography (Biotage, chloroform:methanol=100:3) to obtain 6-{[5-(2,2-diethoxyethoxy)pyridin-2-yl]oxy}-N-(1-methyl-1H-pyrazol-3-yl)quinazoline-4-amine (292 mg, yield: 65%) as a brown oil.

2) A chloroform solution (3 ml) of 6-{[5-(2,2-diethoxyethoxy)pyridin-2-yl]oxy}-N-(1-methyl-1H-pyrazol-3-yl)quinazoline-4-amine (292 mg, 0.65 mmol) obtained in the above reaction was added to a mixed solution of trifluoroacetic acid (3 ml) and water (0.3 ml) cooled with ice, and stirred at room temperature for 3 hours. With cooling with ice, aqueous saturated sodium hydrogencarbonate solution was added to the reaction solution, and extracted with chloroform/methanol (9:1). The organic layer was dried over anhydrous sodium sulfate, and concentrated under reduced pressure to obtain a crude product (283 mg) containing {[6-({4-[(1-methyl-1H-pyrazol-3-yl)amino]quinazolin-6-yl}oxy)pyridin-3-yl]oxy}acetaldehyde as a brown amorphous solid.

3) Isopropylamine (0.045 ml, 0.52 mmol) was added to a tetrahydrofuran solution (3 ml) of the crude aldehyde product (153 mg) obtained in the above reaction, and stirred under a nitrogen atmosphere at room temperature for 10 minutes, then sodium triacetoxyborohydride (222 mg, 1.049 mmol) was added, and the reaction solution was further stirred at room temperature for 20 minutes. Saturated saline water was added to the reaction solution, then extracted with chloroform/methanol (9:1), and the organic layer was dried over anhydrous sodium sulfate and concentrated under reduced pressure. The obtained residue was purified by amine-type silica gel column chromatography (Biotage NH, hexane:ethyl acetate to ethyl acetate:methanol=1:2 to 100:2) to obtain the entitled compound (105 mg, yield: 72%, 2 steps from 2)) as a pale orange amorphous solid.

The analytical data of the entitled compound are shown below.

$^1$H-NMR (DMSO-$d_6$) δ: 0.99 (6H, d, J=5.9 Hz), 2.74-2.78 (1H, m), 2.86 (2H, t, J=5.4 Hz), 3.80 (3H, s), 4.05 (2H, t, J=5.6 Hz), 6.79 (1H, d, J=2.0 Hz), 7.12 (1H, d, J=8.8 Hz), 7.56-7.60 (2H, m), 7.65 (1H, d, J=2.0 Hz), 7.79 (1H, d, J=8.8 Hz), 7.91 (1H, d, J=2.9 Hz), 8.34 (1H, d, J=2.9 Hz), 8.56 (1H, s), 10.30 (1H, s).

ESI-MS (m/e): 420 [M+H]$^+$

Preparation of 5-(2,2-diethoxyethoxy)-2-fluoropyridine

Bromoacetaldehyde diethyl acetal (6.75 ml, 44.9 mmol) and cesium carbonate (30.9 g, 95.0 mmol) were added to an N,N-dimethylacetamide solution (60 ml) of 6-fluoropyridin-3-ol (3.0 g, 24.9 mmol, purity: at most 94%), and stirred under a nitrogen atmosphere at 100° C. for 15 hours. The reaction solution was cooled with ice, water was added, and extracted with ethyl acetate. The organic layer was washed with water and saturated saline water, dried over anhydrous sodium sulfate, and concentrated under reduced pressure. The obtained residue was purified by silica gel column chromatography (Biotage, hexane:ethyl acetate=17:1 to 6:1) to obtain 5-(2,2-diethoxyethoxy)-2-fluoropyridine (5.67 g, yield: 99%) as a pale yellow oil.

Example 6

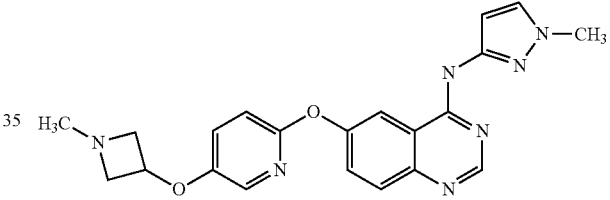

Preparation of 6-({5-[(1-methylazetidin-3-yl)oxy]pyridin-2-yl}oxy)-N-(1-methyl-1H-pyrazol-3-yl)quinazoline-4-amine 1) 5-[2-(1,3-Dioxolan-3-yl)ethoxy]-2-fluoropyridine (800 mg, 3.7 mmol) and potassium tert-butoxide (280 mg, 2.5 mmol) were added to an N,N-dimethylacetamide suspension (3 ml) of 4-[(1-methyl-1H-pyrazol-3-yl)amino]quinazolin-6-ol (300 mg, 1.2 mmol), and reacted under a nitrogen atmosphere at 200° C. for 30 minutes, using microwaves. The reaction solution was cooled to room temperature, diluted with chloroform, and the organic layer was washed with water and saturated saline water, dried over anhydrous sodium sulfate, and concentrated under reduced pressure. The obtained residue was purified by silica gel column chromatography (chloroform:methanol=96:4) to obtain 6-({5-[2-(1,3-dioxolan-2-yl)ethoxy]pyridin-2-yl}oxy)-N-(1-methyl-1H-pyrazol-3-yl)quinazoline-4-amine (530 mg, yield: 99%) as a pale yellow solid.

2) Trifluoroacetic acid (6 ml) and water (0.6 ml) were added to a chloroform solution (6 ml) of the acetal product (530 mg, 1.2 mmol) obtained in the above reaction, and stirred at room temperature for 4 hours. The reaction solution was diluted with chloroform, the organic layer was washed with aqueous saturated sodium hydrogencarbonate solution and saturated saline water, dried over anhydrous sodium sulfate, and concentrated under reduced pressure to obtain a crude product containing 6-({5-[2-(formyl)ethoxy]pyridin-2-yl}oxy)-N-(1-methyl-1H-pyrazol-3-yl)quinazoline-4-amine.

3) Triethylamine (0.34 ml, 2.5 mmol) was added to a tetrahydrofuran (10 ml) solution of the crude product obtained in the above reaction, and stirred for 24 hours at room temperature. The reaction solution was concentrated under reduced pressure, then suspended in ethyl acetate, and the precipitate was collected by filtration to obtain 6-({4-[(1-methyl-1H-pyrazol-3-yl)amino]quinazolin-6-yl}oxy)pyridin-3-ol (310 mg, yield: 76%) as a brown solid.

4) Tert-butyl 3-[(methylsulfonyl)oxy]azetidine-1-carboxylate (230 mg, 0.90 mmol) and potassium tert-butoxide (200 mg, 1.8 mmol) were added to a dimethyl sulfoxide solution (10 ml) of the alcohol product (300 mg, 0.90 mmol) obtained in the above reaction, and stirred at 100° C. for 24 hours. The reaction solution was cooled to room temperature, and diluted with chloroform. The organic layer was washed with aqueous saturated sodium hydrogencarbonate solution and saturated saline water, dried over anhydrous sodium sulfate, and concentrated under reduced pressure. The obtained residue was purified by silica gel column chromatography (hexane:ethyl acetate=70:30) to obtain a crude product (440 mg) containing tert-butyl 3-{[6-({4-[(1-methyl-1H-pyrazol-3-yl)amino]quinazolin-6-yl}oxy)pyridin-3-yl]oxy}azetidine-1-carboxylate, as a pale yellow oil.

5) Trifluoroacetic acid (4 ml) was added to a chloroform solution (4 ml) of the crude azetidine product (440 mg) obtained in the above reaction, and stirred at room temperature for 1 hour. The reaction solution was concentrated under reduced pressure, and a mixed solution of chloroform/methanol (5:1) and aqueous saturated sodium hydrogencarbonate solution were added to the obtained residue. The organic layer was washed with saturated saline water, dried over anhydrous sodium sulfate, and concentrated under reduced pressure. The obtained residue was purified by amine-type silica gel column chromatography (chloroform:methanol=94:6) to obtain a crude product (270 mg) containing 6-{[5-(azetidin-3-yloxy)pyridin-2-yl]oxy}-N-(1-methyl-1H-pyrazol-3-yl)quinazoline-4-amine, as a pale yellow solid.

6) 37% Formaldehyde solution (0.046 ml, 0.62 mmol) and sodium cyanotrihydroborate (19 mg, 0.31 mmol) were added to a methanol solution (2 ml) of the crude amine product (60 mg) obtained in the above reaction, and stirred at room temperature for 1 hour. Water was added to the reaction solution, then extracted with a mixed solution of chloroform/methanol (9:1). The organic layer was washed with saturated saline water, dried over anhydrous sodium sulfate, and concentrated under reduced pressure. The obtained residue was purified by thin-layer silica gel column chromatography (chloroform:methanol=90:10) and amine-type thin-layer silica gel column chromatography (chloroform:methanol=98:2) to obtain the entitled compound (26 mg, yield: 42%) as a colorless amorphous solid.

The analytical data of the entitled compound are shown below.

$^1$HNMR (CD$_3$OD) δ: 2.32 (s, 3H), 3.16-3.19 (m, 2H), 3.68-3.73 (m, 2H), 3.76 (s, 3H), 4.76-4.71 (m, 1H), 6.62 (s, 1H), 6.97 (d, 1H, J=8.8 Hz), 7.33 (dd, 1H, J=8.9, 3.0 Hz), 7.45 (d, 1H, J=2.0 Hz), 7.52 (d, 1H, J=8.3 Hz), 7.64 (d, 1H, J=2.7 Hz), 7.73 (d, 1H, J=9.0 Hz), 7.80 (s, 1H), 7.94 (d, 1H, J=2.0 Hz), 8.43 (s, 1H)

ESI-MS (m/e): 404 [M+H]$^+$

Preparation of 5-[2-(1,3-dioxolan-2-yl)ethoxy]-2-fluoropyridine 2-(2-Bromoethyl)-1,3-dioxolane (2.49 ml, 19.9 mmol) and cesium carbonate (15.1 g, 46.4 mmol) were added to an N,N-dimethylacetamide solution (25 ml) of 6-fluoropyridin-3-ol (1.5 g, 13.3 mmol), and stirred under a nitrogen atmosphere at 100° C. for 12 hours. The reaction solution was cooled with ice, water and ethyl acetate were added, and the organic layer was washed with water and saturated saline water, dried over anhydrous sodium sulfate, and concentrated under reduced pressure. The obtained residue was purified by silica gel column chromatography (Biotage, hexane:ethyl acetate=5:1 to 1:1) to obtain 5-[2-(1,3-dioxolan-2-yl)ethoxy]-2-fluoropyridine (2.43 g, yield: 86%) as a colorless oil.

Example 7

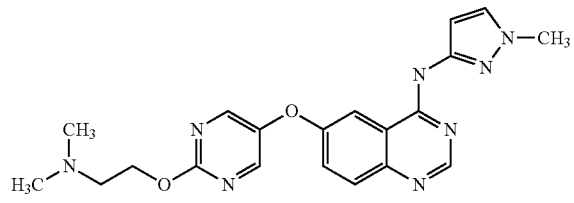

Preparation of 6-({2-[2-(dimethylamino)ethoxy]pyrimidin-5-yl}oxy)-N-(1-methyl-1H-pyrazol-3-yl)quinazoline-4-amine 1) 2-(2,2-Diethoxyethoxy)-5-fluoropyrimidine (168 mg, 0.73 mmol) and potassium tert-butoxide (93 mg, 0.83 mmol) were added to an N,N-dimethylacetamide solution (1 ml) of 4-[(1-methyl-1H-pyrazol-3-yl)amino]quinazolin-6-ol (80 mg, 0.33 mmol), and stirred at 190° C. for 14 hours under a nitrogen atmosphere in a sealed tube. The reaction solution was cooled with ice, water was added, and extracted with chloroform. The organic layer was washed with water, dried over anhydrous sodium sulfate, and concentrated under reduced pressure. The obtained residue was purified by silica gel column chromatography (Moritex, acetone:hexane=1:2) to obtain 6-{[2-(2,2-diethoxyethoxy)pyrimidin-5-yl]oxy}-N-(1-methyl-1H-pyrazol-3-yl)quinazoline-4-amine (56 mg, yield: 37%) as a pale brown amorphous solid.

2) Using the pyrimidine product obtained in the above reaction and in the same manner as in Example 1-2) and 1-3) or according to a method similar to it or according to a combination thereof with an ordinary method, the entitled compound (34 mg) was obtained as a yellow amorphous solid.

The analytical data of the entitled compound are shown below.

$^1$H-NMR (DMSO-d$_6$) δ: 2.23 (6H, s), 2.67 (2H, t, J=5.9 Hz), 3.79 (3H, s), 4.42 (2H, t, J=5.9 Hz), 6.78 (1H, d, J=2.0 Hz), 7.64 (1H, d, J=2.4 Hz), 7.71 (1H, dd, J=2.7, 9.0 Hz), 7.82 (1H, d, J=8.8 Hz), 8.02 (1H, d, J=2.9 Hz), 8.54 (1H, s), 8.63 (2H, s), 10.28 (1H, s).

ESI-MS (m/e): 407 [M+H]$^+$

Preparation of 2-(2,2-diethoxyethoxy)-5-fluoropyrimidine and 2-chloro-5-(2,2-diethoxyethoxy)pyrimidine With cooling with ice, a tetrahydrofuran solution (2 ml) of 2,2-diethoxyethanol (668 mg, 4.98 mmol) was added to a mixed tetrahydrofuran (4 ml)/N,N-dimethylacetamide (2 ml) solution of 2-chloro-5-fluoropyrimidine (600 mg, 4.53 mmol), and stirred under a nitrogen atmosphere for 1 hour. Water was added to the reaction solution, and extracted with ethyl acetate. Next, the organic layer was washed with saturated saline water, dried over anhydrous sodium sulfate, and concentrated under reduced pressure. The obtained residue was purified by silica gel column chromatography (Moritex, acetone:hexane=1:25) to obtain 2-(2,2-diethoxyethoxy)-5-fluoropyrimidine (699 mg, yield: 67%) as a colorless oil, and 2-chloro-5-(2,2-diethoxyethoxy)pyrimidine (233 mg, 21%) as a colorless solid.

Example 8

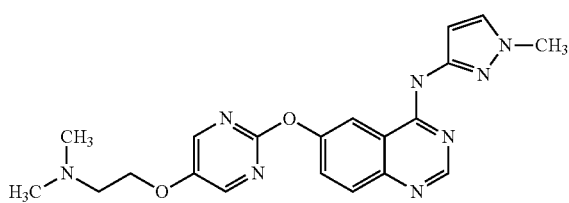

Preparation of 6-({5-[2-(dimethylamino)ethoxy]pyrimidin-2-yl}oxy)-N-(1-methyl-1H-pyrazol-3-yl)quinazoline-4-amine 1) 2-Chloro-5-(2,2-diethoxyethoxy)pyrimidine (225 mg, 0.91 mmol) obtained in Example 7 and potassium tert-butoxide (116 mg, 1.04 mmol) were added to an N,N-dimethylacetamide solution (1 ml) of 4-[(1-methyl-1H-pyrazol-3-yl)amino]quinazolin-6-ol (100 mg, 0.42 mmol), and stirred at 200° C. for 18 hours under a nitrogen atmosphere in a sealed tube. The reaction solution was cooled with ice, water was added, and extracted with chloroform. The organic layer was washed with water, dried over anhydrous sodium sulfate, and concentrated under reduced pressure. The obtained residue was purified by silica gel column chromatography (Moritex, acetone:hexane=2:3) to obtain 6-{[5-(2,2-diethoxyethoxy)pyrimidin-2-yl]oxy}-N-(1-methyl-1H-pyrazol-3-yl)quinazoline-4-amine (177 mg, yield: 95%) as a pale orange amorphous solid.

2) Using 6-{[5-(2,2-diethoxyethoxy)pyrimidin-2-yl]oxy}-N-(1-methyl-1H-pyrazol-3-yl)quinazoline-4-amine obtained in the above reaction and in the same manner as in Example 1-2) and 1-3) or according to a method similar to it or according to a combination thereof with an ordinary method, the entitled compound (62 mg) was obtained as a pale yellow amorphous solid.

The analytical data of the entitled compound are shown below.

$^1$H-NMR (DMSO-$d_6$) δ: 2.21 (6H, s), 2.63 (2H, t, J=5.6 Hz), 3.80 (3H, s), 4.17 (2H, t, J=5.6 Hz), 6.81 (1H, d, J=2.4 Hz), 7.65-7.69 (2H, m), 7.82 (1H, d, J=8.8 Hz), 8.44-8.47 (3H, m), 8.58 (1H, s), 10.29 (1H, s).

ESI-MS (m/e): 407 [M+H]$^+$

Example 9

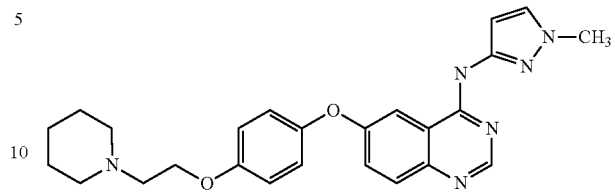

Preparation of N-(1-methyl-1H-pyrazol-3-yl)-6-{[5-(2-piperidin-1-yl)ethoxy)pyridin-2-yl]oxy}quinazoline-4-amine Using 6-{[5-(2,2-diethoxyethoxy)pyridin-2-yl]oxy}-N-(1-methyl-1H-pyrazol-3-yl)quinazoline-4-amine obtained in Example 5-1) and piperidine, and in the same manner as in Example 5-2) and 5-3) or according to a method similar to it or according to a combination thereof with an ordinary method, the entitled compound (59 mg) was obtained as a yellow amorphous solid.

The analytical data of the entitled compound are shown below.

$^1$HNMR (DMSO-$d_6$) δ: 1.30-1.70 (m, 2H), 1.72-1.82 (m, 4H), 2.92-3.02 (m, 2H), 3.42-3.56 (m, 4H), 3.79 (s, 3H), 4.42-4.48 (m, 2H), 6.78 (brs, 1H), 7.18 (d, 2H, J=8.8 Hz), 7.55-7.66 (m, 3H), 7.80 (d, 2H, J=8.8 Hz), 7.96 (brs, 1H), 8.37 (brs, 1H), 8.55 (brs, 1H)

ESI-MS (m/e): 446 [M+H]$^+$

Example 10

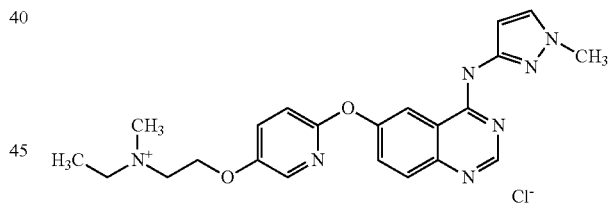

Preparation of 6-[(5-{2-[ethyl(methyl)amino]ethoxy}pyridin-2-yl)oxy]-N-(1-methyl-1H-pyrazol-3-yl)quinazoline-4-amine hydrochloride 1) Using 6-{[5-(2,2-diethoxyethoxy)pyridin-2-yl]oxy}-N-(1-methyl-1H-pyrazol-3-yl)quinazoline-4-amine obtained in Example 5-1) and ethyl(methyl)amine, and in the same manner as in Example 5-2) and 5-3) or according to a method similar to it or according to a combination thereof with an ordinary method, 6-[(5-{2-[ethyl(methyl)amino]ethoxy}pyridin-2-yl)oxy]-N-(1-methyl-1H-pyrazol-3-yl)quinazoline-4-amine (76 mg) was obtained.

2) The amine product (76 mg) obtained in the above reaction was dissolved in methanol (1 ml), and aqueous 1 M hydrochloric acid solution (0.179 ml, 0.179 mmol) was added and concentrated under reduced pressure to obtain the entitled compound (66 mg, yield: 59.5) as a pale yellow solid.

The analytical data of the entitled compound are shown below.

¹HNMR (DMSO-d₆) δ: 1.21 (t, 3H, J=7.2 Hz), 2.75 (s, 3H), 3.00-3.60 (m, 4H), 3.77 (s, 3H), 4.40 (brs, 2H), 6.73 (s, 1H), 7.14 (d, 1H, J=9.1 Hz), 7.58-7.66 (m, 3H), 7.81 (d, 1H, J=9.1 Hz), 7.93 (d, 1H, J=3.2 Hz), 8.38 (s, 1H), 8.62 (s, 1H).

ESI-MS (m/e): 420 [M+H]⁺

Example 11

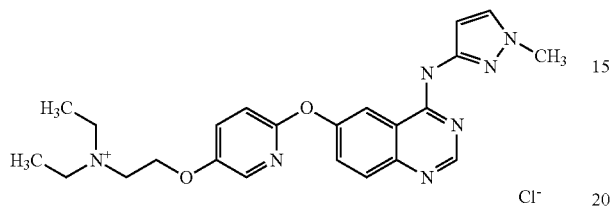

Preparation of 6-({5-[2-(diethylamino)ethoxy]pyridin-2-yl}oxy)-N-(1-methyl-1H-pyrazol-3-yl)quinazoline-4-amine hydrochloride Using 6-{[5-(2,2-diethoxyethoxy)pyridin-2-yl]oxy}-N-(1-methyl-1H-pyrazol-3-yl)quinazoline-4-amine obtained in Example 5-1) and diethylamine, and in the same manner as in Example 5-2) and 5-3) and Example 10-2), or according to a method similar to it or according to a combination thereof with an ordinary method, the entitled compound (55 mg) was obtained as a pale yellow solid.

The analytical data of the entitled compound are shown below.

¹HNMR (DMSO-d₆) δ: 1.20 (t, 6H, J=7.2 Hz), 3.25-3.36 (m, 4H), 3.42-3.50 (m, 2H), 3.75 (s, 3H), 4.39 (brs, 2H), 6.73 (brs, 1H), 7.12 (d, 1H, J=8.8 Hz), 7.64-7.51 (m, 3H), 7.75 (d, 1H, J=9.1 Hz), 7.92 (d, 1H, J=2.9 Hz), 8.32 (s, 1H), 8.52 (s, 1H).

ESI-MS (m/e): 434 [M+H]⁺

Example 12

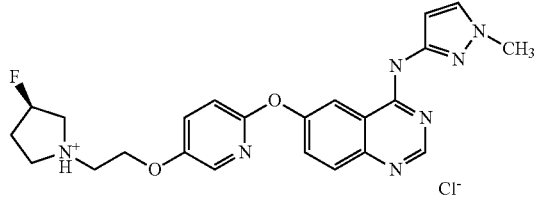

Preparation of 6-[(5-{2-[(3R)-3-fluoropyrrolidin-1-yl]ethoxy}pyridin-2-yl)oxy]-N-(1-methyl-1H-pyrazol-3-yl)quinazoline-4-amine hydrochloride Using 6-{[5-(2,2-diethoxyethoxy)pyridin-2-yl]oxy}-N-(1-methyl-1H-pyrazol-3-yl)quinazoline-4-amine obtained in Example 5-1) and (3R)-3-fluoropyrrolidine, and in the same manner as in Example 5-2) and 5-3) and Example 10-2), or according to a method similar to it or according to a combination thereof with an ordinary method, the entitled compound (40 mg) was obtained as a pale yellow solid.

The analytical data of the entitled compound are shown below.

¹HNMR (DMSO-d₆) δ: 2.07-2.36 (m, 2H), 3.07-3.71 (m, 6H), 3.76 (s, 3H), 4.38 (t, 2H, J=4.7 Hz), 5.40 (d, 1H, J=52.2 Hz), 6.72 (s, 1H), 7.13 (d, 1H, J=8.8 Hz), 7.66-7.54 (m, 3H), 7.77 (d, 1H, J=8.8 Hz), 7.94 (d, 1H, J=2.9 Hz), 8.34 (s, 1H), 8.56 (s, 1H).

ESI-MS (m/e): 450 [M+H]⁺

Example 13

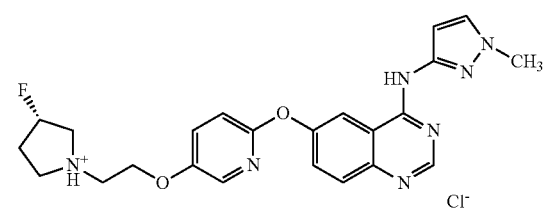

Preparation of 6-[(5-{2-[(3S)-3-fluoropyrrolidin-1-yl]ethoxy}pyridin-2-yl)oxy]-N-(1-methyl-1H-pyrazol-3-yl)quinazoline-4-amine hydrochloride Using 6-{[5-(2,2-diethoxyethoxy)pyridin-2-yl]oxy}-N-(1-methyl-1H-pyrazol-3-yl)quinazoline-4-amine obtained in Example 5-1) and (3S)-3-fluoropyrrolidine, and in the same manner as in Example 5-2) and 5-3) and Example 10-2), or according to a method similar to it or according to a combination thereof with an ordinary method, the entitled compound (29 mg) was obtained as a pale yellow solid.

The analytical data of the entitled compound are shown below.

¹HNMR (DMSO-d₆) δ: 2.07-2.36 (m, 2H), 3.07-3.71 (m, 6H), 3.76 (s, 3H), 4.38 (t, 2H, J=4.7 Hz), 5.40 (d, 1H, J=52.2 Hz), 6.72 (s, 1H), 7.13 (d, 1H, J=8.8 Hz), 7.66-7.54 (m, 3H), 7.77 (d, 1H, J=8.8 Hz), 7.94 (d, 1H, J=2.9 Hz), 8.34 (s, 1H), 8.56 (s, 1H).

ESI-MS (m/e): 450 [M+H]⁺

Example 14

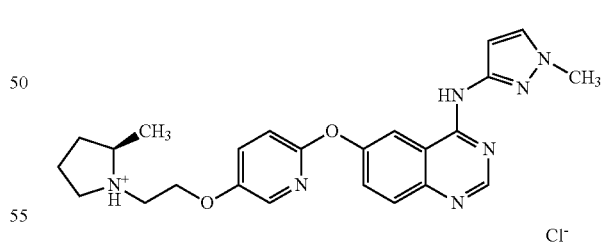

Preparation of N-(1-methyl-1H-pyrazol-3-yl)-6-{[5-{2-[(2R)-2-methylpyrrolidin-1-yl]ethoxy}pyridin-2-yl)oxy]quinazoline-4-amine hydrochloride Using 6-{[5-(2,2-diethoxyethoxy)pyridin-2-yl]oxy}-N-(1-methyl-1H-pyrazol-3-yl)quinazoline-4-amine obtained in Example 5-1) and (2R)-2-methylpyrrolidine, and in the same manner as in Example 5-2) and 5-3) and Example 10-2), or according to a method similar to it or according to a combination thereof with an ordinary method, the entitled compound (23 mg) was obtained as a pale yellow solid.

The analytical data of the entitled compound are shown below.

$^1$HNMR (DMSO-$d_6$) δ: 1.34 (d, 3H, J=6.5 Hz), 1.54-1.65 (m, 1H), 1.86-1.96 (m, 2H), 2.11-2.19 (m, 1H), 3.12-3.47 (m, 4H), 3.56-3.72 (m, 1H), 3.76 (s, 3H), 4.35 (brs, 2H), 6.75 (s, 1H), 7.15 (d, 1H, J=8.8 Hz), 7.57-7.64 (m, 3H), 7.78 (d, 1H, J=7.9 Hz), 7.93 (d, 1H, J=2.9 Hz), 8.39 (brs, 1H), 8.61 (brs, 1H).

ESI-MS (m/e): 446 [M+H]$^+$

Example 15

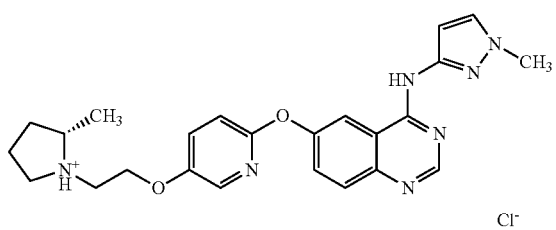

Preparation of N-(1-methyl-1H-pyrazol-3-yl)-6-{[5-{2-[(2S)-2-methylpyrrolidin-1-yl]ethoxy}pyridin-2-yl)oxy]quinazoline-4-amine hydrochloride Using 6-{[5-(2,2-diethoxyethoxy)pyridin-2-yl]oxy}-N-(1-methyl-1H-pyrazol-3-yl)quinazoline-4-amine obtained in Example 5-1) and (2S)-2-methylpyrrolidine, and in the same manner as in Example 5-2) and 5-3) and Example 10-2), or according to a method similar to it or according to a combination thereof with an ordinary method, the entitled compound (24 mg) was obtained as a pale yellow solid.

The analytical data of the entitled compound are shown below.

$^1$HNMR (DMSO-$d_6$) δ: 1.34 (d, 3H, J=6.5 Hz), 1.54-1.65 (m, 1H), 1.86-1.96 (m, 2H), 2.11-2.19 (m, 1H), 3.12-3.47 (m, 4H), 3.56-3.72 (m, 1H), 3.76 (s, 3H), 4.35 (brs, 2H), 6.75 (s, 1H), 7.15 (d, 1H, J=8.8 Hz), 7.57-7.64 (m, 3H), 7.78 (d, 1H, J=7.9 Hz), 7.93 (d, 1H, J=2.9 Hz), 8.39 (brs, 1H), 8.61 (brs, 1H).

ESI-MS (m/e): 446 [M+H]$^+$

Example 16

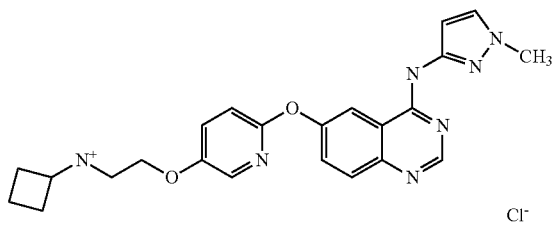 [SMILES: Cn1ccc(Nc2ncnc3ccc(Oc4ccc(OCC[NH2+]C5CCC5)cn4)cc23)n1 ; [Cl-]]

Preparation of 6-({5-[2-(cyclobutylamino)ethoxy]pyridin-2-yl}oxy)-N-(1-methyl-1H-pyrazol-3-yl)quinazoline-4-amine hydrochloride Using 6-{[5-(2,2-diethoxyethoxy)pyridin-2-yl]oxy}-N-(1-methyl-1H-pyrazol-3-yl)quinazoline-4-amine obtained in Example 5-1) and cyclobutylamine, and in the same manner as in Example 5-2) and 5-3) and Example 10-2), or according to a method similar to it or according to a combination thereof with an ordinary method, the entitled compound (69 mg) was obtained as a pale yellow solid.

The analytical data of the entitled compound are shown below.

$^1$H-NMR (CD$_3$OD) δ: 1.40-1.50 (2H, m), 1.77-1.89 (4H, m), 2.80-2.82 (1H, m), 2.86 (4H, m), 3.37 (3H, s), 3.83 (2H, t, J=4.9 Hz), 6.20 (1H, d, J=2.3 Hz), 6.60 (1H, d, J=8.6 Hz), 7.04 (1H, d, J=2.3 Hz), 7.13 (2H, dd, J=2.7, 9.0, Hz), 7.28 (1H, d, J=9.0 Hz), 7.44 (1H, d, J=2.7 Hz), 7.59 (1H, d, J=2.3 Hz), 7.95-8.12 (1H, m).

ESI-MS m/z=432.3 (M+H)$^+$

Example 17

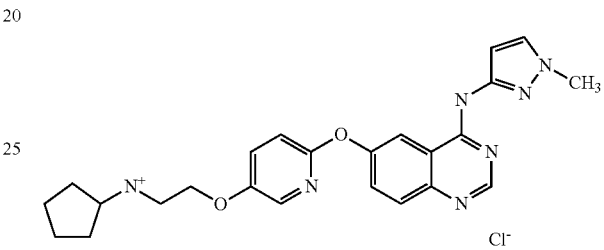

Preparation of 6-({5-[2-(cyclopentylamino)ethoxy]pyridin-2-yl}oxy)-N-(1-methyl-1H-pyrazol-3-yl)quinazoline-4-amine hydrochloride Using 6-{[5-(2,2-diethoxyethoxy)pyridin-2-yl]oxy}-N-(1-methyl-1H-pyrazol-3-yl)quinazoline-4-amine obtained in Example 5-1) and cyclopentylamine, and in the same manner as in Example 5-2) and 5-3) and Example 10-2), or according to a method similar to it or according to a combination thereof with an ordinary method, the entitled compound (94 mg) was obtained as a pale yellow solid.

The analytical data of the entitled compound are shown below.

$^1$H-NMR (CD$_3$OD) δ: 1.25 (8H, m), 2.99 (2H, t, J=5.1 Hz), 3.16 (1H, m), 3.34 (3H, s), 3.87 (2H, t, J=5.1 Hz), 6.19 (1H, d, J=1.2 Hz), 6.59 (1H, d, J=9.0 Hz), 7.04 (1H, d, J=2.0 Hz), 7.10-7.14 (2H, m), 7.28 (1H, dd, J=9.0, 1.2 Hz), 7.43 (1H, t, J=4.5 Hz), 7.58 (1H, s), 8.04 (1H, s).

ESI-MS m/z=446.3 (M+H)$^+$

Example 18

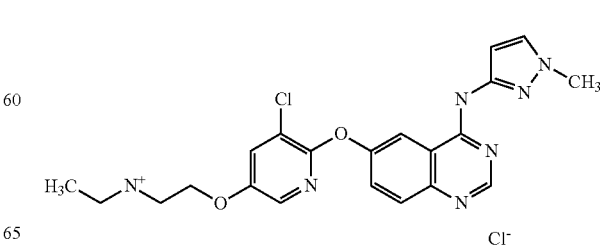

Preparation of 6-({3-chloro-5-[2-(ethylamino) ethoxy]pyridin-2-yl}oxy)-N-(1-methyl-1H-pyrazol-3-yl)quinazoline-4-amine hydrochloride Using 4-[(1-methyl-1H-pyrazol-3-yl)amino]quinazolin-6-ol obtained in Example 1-1) and 2), and 2,3-dichloro-5-(2,2-diethoxyethoxy)pyridine and 2 M ethylamine/tetrahydrofuran solution, and in the same manner as in Example 1-3) and Example 10-2), or according to a method similar to it or according to a combination thereof with an ordinary method, the entitled compound (223 mg) was obtained as a pale yellow solid.

The analytical data of the entitled compound are shown below.

$^1$H-NMR (DMSO-D$_6$) δ: 1.22 (3H, t, J=7.1 Hz), 2.99-3.05 (2H, m), 3.31-3.34 (2H, m), 3.80 (3H, s), 4.34-4.37 (2H, m), 6.78 (1H, d, J=2.2 Hz), 7.65-7.67 (2H, m), 7.82 (1H, d, J=8.8 Hz), 7.94-7.95 (2H, m), 8.38 (1H, d, J=2.2 Hz), 8.60 (1H, s), 8.90-8.99 (2H, brs), 10.40-10.45 (1H, brs)

ESI-MS (m/e): 440 [M+H]$^+$

Example 19

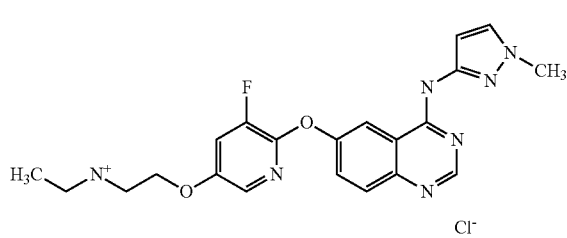 [SMILES: CC[NH2+]CCOc1cnc(Oc2ccc3ncnc(Nc4ccn(C)n4)c3c2)c(F)c1 ; [Cl-]]

Preparation of 6-({5-[2-(ethylamino)ethoxy]-3-fluoropyridin-2-yl}oxy)-N-(1-methyl-1H-pyrazol-3-yl)quinazoline-4-amine hydrochloride Using 4-[(1-methyl-1H-pyrazol-3-yl)amino]quinazolin-6-ol, 5-(2,2-diethoxyethoxy)-2,3-difluoropyridine and 2 Methylamine/tetrahydrofuran solution, and in the same manner as in Example 1 and Example 10-2), or according to a method similar to it or according to a combination thereof with an ordinary method, the entitled compound (104 mg) was obtained as a pale yellow solid.

The analytical data of the entitled compound are shown below.

$^1$H-NMR (CD$_3$OD) δ: 1.33 (3H, t, J=7.2 Hz), 3.15 (2H, q, J=7.2 Hz), 3.45 (2H, t, J=4.7 Hz), 3.83 (3H, s), 4.33 (2H, t, J=4.7 Hz), 6.67-6.69 (1H, m), 7.53 (1H, d, J=2.7 Hz), 7.57 (1H, dd, J=2.7, 11.0 Hz), 7.65 (1H, dd, J=2.7, 9.0 Hz), 7.77 (1H, d, J=2.7 Hz), 7.80 (1H, d, J=9.0 Hz), 8.08-8.10 (1H, m), 8.52 (1H, s).

ESI-MS (m/e): 424 [M+H]$^+$

Preparation of 5-(2,2-diethoxyethoxy)-2,3-difluoropyridine

1) A 1,4-dioxane solution (30 ml) of tris(dibenzylideneacetone)dipalladium(0) (115 mg, 0.20 mmol) and tricyclohexyl phosphine (135 mg, 0.48 mmol) was degassed, then stirred at room temperature for 30 minutes. To the reaction solution, added were bis(pinacolato)diboron (1.87 g, 7.36 mmol), potassium acetate (985 mg, 10.0 mmol) and 5-chloro-2,3-difluoropyridine (1.0 g, 6.69 mmol), then degassed and stirred at 80° C. for 10 hours. The reaction solution was cooled to room temperature, water was added, the insoluble matter was separated by filtration, and the filtrate was extracted with ethyl acetate. The organic layer was washed with saturated saline water, then dried over anhydrous sodium sulfate, and concentrated under reduced pressure to obtain a crude product (2.6 g) containing 2,3-difluoro-5-(4,4,5,5-tetramethyl-1,3,2-dioxaborolan-2-yl)pyridine as an orange oil.

2) Hydrogen peroxide water (1.37 ml, 13.4 mmol) was added to a tetrahydrofuran solution (15 ml) of the crude pyridine product (2.6 g) obtained in the above, and stirred at room temperature for 2 hours. Water was added to the reaction solution, and extracted with ethyl acetate. The organic layer was washed with aqueous 5% sodium thiosulfate solution and saturated saline water, dried over anhydrous sodium sulfate, and concentrated under reduced pressure. The obtained residue was purified by silica gel column chromatography (Biotage, hexane:ethyl acetate=5:1 to 3:1) to obtain an yellow gum (1.0 g) containing 5,6-difluoropyridin-3-ol.

3) Bromoacetaldehyde diethyl acetal (1.41 ml, 9.40 mol) and cesium carbonate (7.44 g, 22.8 mmol) were added to an N,-dimethyl acetamide solution (10 ml) of the phenol product (1.0 g) obtained n the above reaction, and stirred under a nitrogen atmosphere at 100° C. for 3 hours. The reaction solution was cooled with ice, water was added, and extracted with ethyl acetate. Next, the organic layer was washed with water, dried over anhydrous sodium sulfate, and concentrated under reduced pressure. The obtained residue was purified by silica gel column chromatography (Biotage, hexane:ethyl acetate=20:1 to 10:1) to obtain 5-(2,2-diethoxyethoxy)-2,3-difluoropyridine (914 mg, yield: 55%, 3 steps from 1)), as a pale orange oil.

Example 20

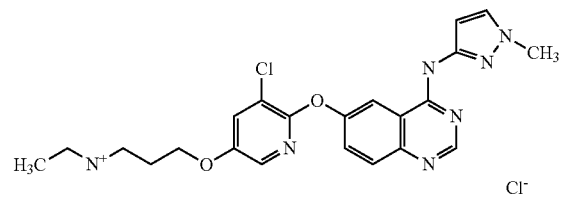 [SMILES: CC[NH2+]CCCOc1cnc(Oc2ccc3ncnc(Nc4ccn(C)n4)c3c2)c(Cl)c1 ; [Cl-]]

Preparation of 6-({3-chloro-5-[3-(ethylamino)propoxy]pyridin-2-yl}oxy)-N-(1-methyl-1H-pyrazol-3-yl)quinazoline-4-amine hydrochloride 1) 3-Chloro-5-[2-(1,3-dioxolan-2-yl)ethoxy]-2-fluoropyridine (4.6 g, 18.4 mmol) and potassium tert-butoxide (2.6 g, 23 mmol) were added to an N,N-dimethylacetamide suspension (5 ml) of 4-[(1-methyl-1H-pyrazol-3-yl)amino]quinazolin-6-ol (2.2 g, 9.1 mmol), and reacted at 200° C. for 2 hours, using microwaves. The reaction solution was cooled to room temperature, aqueous saturated ammonium chloride solution was added, and extracted with ethyl acetate. The organic layer was washed with water and saturated saline water, dried over anhydrous sodium sulfate, and concentrated under reduced pressure. The obtained residue was purified by silica gel column chromatography (hexane:ethyl acetate=75:25) to obtain 6-({3-chloro-5-[2-(1,3-dioxolan-2-yl)ethoxy]pyridin-2-yl}oxy)-N-(1-methyl-1H-pyrazol-3-yl)quinazoline-4-amine (3.1 g, yield: 73%) as a yellow solid.

2) Trifluoroacetic acid (4 ml) and water (0.4 ml) were added to a chloroform solution (4 ml) of the acetal product (2.4 g, 5.1 mmol) obtained in the above reaction, and stirred at room temperature for 2 days. Aqueous 0.7 M sodium carbonate solution (90 ml, 63 mmol) was added to the reaction solution, then extracted with a mixed solution of chloroform/methanol (9:1). The organic layer was washed with saturated saline water, dried over anhydrous sodium sulfate, and concentrated under reduced pressure to obtain 6-({3-chloro-5-[2-(formyl)ethoxy]pyridin-2-yl}oxy)-N-(1-methyl-1H-pyrazol-3-yl)quinazoline-4-amine (1.57 g) as a crude product.

3) With cooling with ice, sodium borohydride (37 mg, 1.0 mmol) was added to a methanol/tetrahydrofuran (4:1) solution (5 ml) of the crude product (416 mg) obtained in the above reaction, and stirred at room temperature for 2 hours. Saturated ammonium chloride was added to the reaction solution, then extracted with a mixed solution of chloroform/methanol (9:1), and the organic layer was washed with saturated saline water, dried over anhydrous sodium sulfate, and concentrated under reduced pressure. The obtained residue was purified by silica gel column chromatography (hexane:ethyl acetate=50:50 to 0:100) to obtain 3-{[5-chloro-6-({4-[(1-methyl-1H-pyrazol-3-yl)amino]quinazolin-6-yl}oxy)pyridin-3-yl]oxy}propan-1-ol (148 mg, yield: 35%) as a pale yellow solid.

4) With cooling with ice, triethylamine (0.17 ml, 1.3 mmol) and methanesulfonyl chloride (0.072 ml, 0.80 mmol) were added to a tetrahydrofuran solution (1 ml) of the alcohol product (147 mg, 0.34 mmol) obtained in the above reaction, and stirred for 24 hours at room temperature. The precipitate of the reaction solution was separated by filtration followed by dilution with a mixed solution of chloroform/methanol (4:1). The organic layer was washed with aqueous saturated sodium hydrogencarbonate solution and saturated saline water, dried over anhydrous sodium sulfate, and concentrated under reduced pressure to obtain 6-({3-chloro-5-[2-(methylsulfonyloxy)ethoxy]pyridin-2-yl}oxy)-N-(1-methyl-1H-pyrazol-3-yl)quinazoline-4-amine (174 mg) as a crude product.

5) 2 Methylamine/tetrahydrofuran solution (11 ml, 23 mmol) was added to a tetrahydrofuran solution (1 ml) of the crude product (55 mg) obtained in the above reaction, and stirred for 24 hours at 80° C. in a sealed tube. The reaction solution was concentrated under reduced pressure, and the obtained residue was purified by amine-type silica gel column chromatography (chloroform:methanol=98:2), then dissolved in methanol, and aqueous 5 M hydrochloric acid solution (0.0065 ml, 0.032 mmol) was added, and concentrated under reduced pressure to obtain the entitled compound (13 mg, yield: 30%) as a yellow solid.

The analytical data of the entitled compound are shown below.

$^1$H-NMR (DMSO-D$_6$) δ: 1.19 (3H, t, J=6.3 Hz), 2.03-2.10 (2H, m), 2.91-3.08 (4H, m), 3.79 (3H, s), 4.14-4.20 (2H, m), 6.78 (1H, d, J=2.2 Hz), 7.60-7.67 (2H, m), 7.79-7.81 (1H, d, J=8.0 Hz), 7.88-7.90 (2H, m), 834 (1H, d, J=2.2 Hz), 8.57 (1H, s), 8.71-8.83 (2H, m), 10.30-10.34 (1H, brs).

ESI-MS (m/e): 454 [M+H]$^+$

Preparation of 3-chloro-5-[2-(1,3-dioxolan-2-yl)ethoxy]-2-fluoropyridine

1) With cooling with ice, 1-chloropyrrolidine-2,5-dione (10 g, 76 mmol) was added to an N,N-dimethylformamide solution (30 ml) of 5-bromopyridine-2-amine (12 g, 69 mmol), and stirred for 4 hours. The reaction solution was diluted with water, neutralized with aqueous 5 N sodium hydroxide solution, and extracted with diethyl ether. The organic layer was washed with saturated saline water, dried over anhydrous sodium sulfate, and concentrated under reduced pressure. The obtained residue was purified by silica gel column chromatography (hexane:chloroform:ethyl acetate=25:25:50) to obtain 5-bromo-3-chloropyridine-2-amine (12.6 g, yield: 88%) as a brown solid.

2) With cooling with ice, sodium nitrite (4.8 g, 70 mmol) was added to a hydrogen fluoride/pyridine (70% HF) solution (91 ml) of the amine product (12.6 g, 61 mmol) obtained in the above reaction, and stirred at room temperature for 30 minutes. Ice was added to the reaction solution, neutralized with sodium carbonate, extracted with diethyl ether. The organic layer was washed with water and saturated saline water, dried over anhydrous sodium sulfate, and concentrated under reduced pressure. The obtained residue was purified by silica gel column chromatography (hexane:ethyl acetate=80:20) to obtain 5-bromo-3-chloro-2-fluoropyridine (11.1 g, yield: 87%) as a white solid.

3) At −78° C., 1.6 M n-butyllithium (31 ml, 49 mmol) was dropwise added to a diethyl ether solution (150 ml) of the fluoropyridine product (9.9 g, 47 mmol) obtained in the above reaction. The reaction solution was stirred at −78° C. for 15 minutes, then triisopropyl boronate (13 ml, 57 mmol) was dropwise added and heated up to room temperature, taking 1 hour. Aqueous 1 N sodium hydroxide solution (40 ml, 40 mmol) was added to the reaction solution, then 30% hydrogen peroxide water (9.6 ml, 94 mmol) was dropwise added, and stirred at room temperature for 30 minutes. With cooling with ice, this was processed with excessive hydrogen peroxide and aqueous saturated sodium thiosulfate solution, and then water was added. The aqueous layer and the organic layer were washed with aqueous 1 N sodium hydroxide solution, the obtained aqueous layers were combined, and made to have a pH of 1 with 5H hydrochloric acid. The aqueous solution was extracted with ethyl acetate, the organic layer was washed with saturated saline water, dried over anhydrous sodium sulfate, and concentrated under reduced pressure. The obtained residue was suspended in a small amount of chloroform, filtered and dried to obtain 5-chloro-6-fluoropyridin-3-ol (4.0 g, yield: 58%) as a colorless solid.

4) Cesium carbonate (14 g, 44 mmol) and 2-(2-bromoethyl)-1,3-dioxolane (4.5 g, 25 mmol) were added to an N,N-dimethylformamide suspension (16 ml) of the alcohol product (2.8 g, 19 mmol) obtained in the above reaction, and stirred at 100° C. for 4 hours. The reaction solution was cooled to room temperature, water was added, and extracted with ethyl acetate. The organic layer was washed with water and saturated saline water, dried over anhydrous sodium sulfate, and concentrated under reduced pressure. The obtained residue was purified by silica gel column chromatography (hexane:ethyl acetate=75:25) to obtain 3-chloro-5-[2-(1,3-dioxolan-2-yl)ethoxy]-2-fluoropyridine (3.9 g, yield: 83%) as a colorless oil.

Example 21

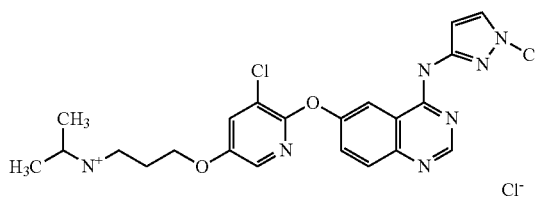

Preparation of 6-({3-chloro-5-[3-(isopropylamino)propoxy]pyridin-2-yl}oxy)-N-(1-methyl-1H-pyrazol-3-yl)quinazoline-4-amine hydrochloride Using the methanesulfonate product obtained in Example 20-4) and isopropylamine, and in the same manner as in Example 20-5) or according to a method similar to it or according to a combination thereof with an ordinary method, the entitled compound (17 mg) was obtained as a yellow amorphous solid.

The analytical data of the entitled compound are shown below.

$^1$H-NMR (DMSO-D$_6$) δ: 1.24 (6H, d, J=6.3 Hz), 2.05-2.15 (2H, m), 3.00-3.15 (2H, m), 3.30-3.34 (1H, m), 3.81 (3H, s), 4.15-4.20 (2H, m), 6.77 (1H, d, J=2.2 Hz), 7.68-7.70 (2H, m), 7.82 (1H, d, J=8.0 Hz), 7.90-7.91 (2H, m), 8.38 (1H, d, J=2.2 Hz), 8.65 (1H, s), 8.81-8.83 (2H, m), 10.50-10.70 (1H, brs)

ESI-MS (m/e): 468 [M+H]$^+$

Example 22

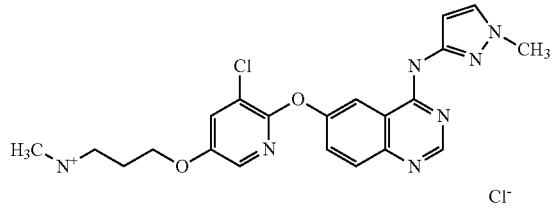

Preparation of 6-({3-chloro-5-[3-(methylamino)propoxy]pyridin-2-yl}oxy)-N-(1-methyl-1H-pyrazol-3-yl)quinazoline-4-amine hydrochloride 1) Using 4-[(1-methyl-1H-pyrazol-3-yl)amino]quinazolin-6-ol and 3-chloro-5-[2-(1,3-dioxolan-2-yl)ethoxy]-2-fluoropyridine, and in the same manner as in Example 6-2) and 6-3) or according to a method similar to it or according to a combination thereof with an ordinary method, 5-chloro-6-({4-[(1-methyl-1H-pyrazol-3-yl)amino]quinazolin-6-yl}oxy)pyridin-3-ol (738 mg) was obtained as a pale yellow amorphous solid.

2) Tert-butyl (3-chloropropyl)methyl carbamate (61 mg, 0.29 mmol) and potassium tert-butoxide (55 mg, 0.49 mmol) were added to a dimethyl sulfoxide solution (3 ml) of the alcohol product (90 mg, 0.24 mmol) obtained in the above reaction, and stirred at 100° C. for 12 hours. The reaction solution was cooled to room temperature, then diluted with chloroform. The organic layer was washed with aqueous saturated sodium hydrogencarbonate solution and saturated saline water, then dried over anhydrous sodium sulfate, and concentrated under reduced pressure. The obtained residue was purified by silica gel column chromatography to obtain tert-butyl (3-{[5-chloro-6-({4-[(1-methyl-1H-pyrazol-3-yl)amino]quinazolin-6-yl}oxy)pyridin-3-yl]oxy}propyl)methylcarboxylate (50 mg, yield: 40%) as a pale yellow amorphous solid.

3) Using (3-{[5-chloro-6-({4-[(1-methyl-1H-pyrazol-3-yl)amino]quinazolin-6-yl}oxy)pyridin-3-yl]oxy}propyl)methylcarboxylate obtained in the above reaction and in the same manner as in Example 6-4) and 6-5) and Example 10-2), or according to a method similar to it or according to a combination thereof with an ordinary method, the entitled compound (19 mg) was obtained as a pale yellow solid.

The analytical data of the entitled compound are shown below.

$^1$H-NMR (DMSO-D$_6$) δ: 2.04-2.07 (2H, m), 2.56 (3H, s), 3.00-3.05 (2H, m), 3.79 (3H, s), 4.16 (2H, t, J=6.1 Hz), 6.78 (1H, d, J=2.2 Hz), 7.62-7.65 (2H, m), 7.81 (1H, d, J=8.0 Hz), 7.88-7.90 (2H, m), 8.33 (1H, d, J=2.2 Hz), 858 (1H, s), 8.68-8.70 (2H, m), 10.30-10.40 (1H, brs)

ESI-MS (m/e): 440 [M+H]$^+$

Example 23

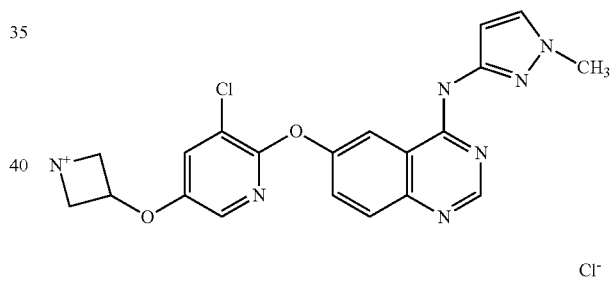

Preparation of 6-{[5-(azetidin-3-yloxy)-3-chloropyridin-2-yl]oxy}-N-(1-methyl-1H-pyrazol-3-yl)quinazoline-4-amine hydrochloride Using 5-chloro-6-({4-[(1-methyl-1H-pyrazol-3-yl)amino]quinazolin-6-yl}oxy)pyridin-3-ol obtained in Example 22 and tert-butyl 3-[(methylsulfonyl)oxy]azetidine-1-carboxylate, and in the same manner as in Example 6-4) and 6-5) and Example 10-2), or according to a method similar to it or according to a combination thereof with an ordinary method, the entitled compound (86 mg) was obtained as a pale yellow solid.

The analytical data of the entitled compound are shown below.

$^1$H-NMR (DMSO-D$_6$) δ: 3.80 (3H, s), 3.90-4.06 (2H, m), 4.42-4.44 (2H, m), 5.12-5.15 (1H, m), 6.77 (1H, d, J=2.2 Hz), 7.66-7.72 (2H, m), 7.80-7.92 (3H, m), 8.52 (1H, d, J=2.2 Hz), 8.58-8.70 (1H, s), 9.20-9.50 (2H, m), 10.05-10.750 (1H, brs)

ESI-MS (m/e): 424 [M+H]$^+$

Example 24

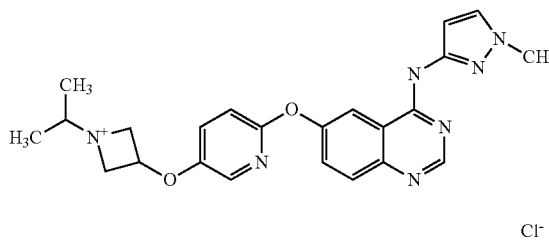

Preparation of 6-({5-[(1-isopropylazetidin-3-yl)oxy]pyridin-2-yl}oxy)-N-(1-methyl-1H-pyrazol-3-yl)quinazoline-4-amine hydrochloride Acetone (0.019 ml, 0.26 mmol) was added to a methanol solution (1 ml) of 6-{[5-(azetidin-3-yloxy)pyridin-2-yl]oxy}-N-(1-methyl-1H-pyrazol-3-yl)quinazoline-4-amine (50 mg, 0.13 mmol) obtained in Example 6-5), stirred for 10 minutes, then a methanol solution (1.7 ml, 0.26 mmol) of 0.15 M zinc cyanotrihydroborate was added and stirred for 1 hour. 1 N sodium hydroxide was added to the reaction solution, then extracted with a mixed solution of chloroform/methanol (9:1). The organic layer was washed with saturated saline water, then dried over anhydrous sodium sulfate, and concentrated under reduced pressure. The obtained residue was purified by thin-layer silica gel column chromatography (chloroform:methanol=90:10) to obtain 6-({5-[(1-isopropylazetidin-3-yl)oxy]pyridin-2-yl}oxy)-N-(1-methyl-1H-pyrazol-3-yl)quinazoline-4-amine. The compound was dissolved in methanol, then aqueous 5 M hydrochloric acid solution (0.017 ml, 0.085 mmol) was added and concentrated under reduced pressure to obtain the entitled compound (40 mg, yield: 67%) as a pale yellow solid.

The analytical data of the entitled compound are shown below.

$^1$HNMR (DMSO-$d_6$) δ: 1.16 (d, 6H, J=5.6 Hz), 3.46 (brs, 1H), 3.80 (s, 3H), 4.17 (brs, 2H), 4.42-4.61 (brm, 2H), 5.01 (brs, 1H), 6.79 (s, 1H), 7.15-7.22 (m, 1H), 7.53-7.63 (m, 2H), 7.66 (d, 1H, J=2.2 Hz), 7.78-7.89 (m, 2H), 8.40 (s, 1H), 8.60 (s, 1H), 11.03-10.74 (brm, 1H)

ESI-MS (m/e): 432 [M+H]$^+$

Example 25

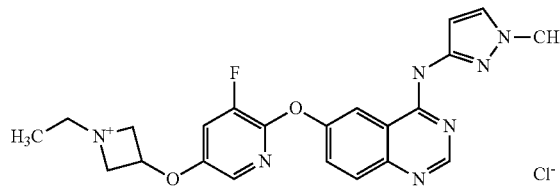

Preparation of 6-({5-[(1-ethylazetidin-3-yl)oxy]-3-fluoropyridin-2-yl}oxy)-N-(1-methyl-1H-pyrazol-3-yl)quinazoline-4-amine hydrochloride 1) Using 4-[(1-methyl-1H-pyrazol-3-yl)amino]quinazolin-6-ol, 5-[2-(1,3-dioxolan-2-yl)ethoxy]-2,3-difluoropyridine and tert-butyl 3-[(methylsulfonyl)oxy]azetidine-1-carboxylate, and in the same manner as in Example 6-5) or according to a method similar to it or according to a combination thereof with an ordinary method, 6-({5-[(1-ethylazetidin-3-yl)oxy]-3-fluoropyridin-2-yl}oxy)-N-(1-methyl-1H-pyrazol-3-yl)quinazoline-4-amine was obtained.

2) Using the amine product obtained in the above reaction and aqueous acetaldehyde solution, and in the same manner as in Example 6-6) and Example 24, or according to a method similar to it or according to a combination thereof with an ordinary method, the entitled compound (30 mg) was obtained as a pale yellow solid.

The analytical data of the entitled compound are shown below.

$^1$H-NMR (CD$_3$OD) δ: 1.21 (3H, t, J=7.2 Hz), 3.31 (2H, q, J=7.2 Hz), 3.83 (3H, s), 4.24-4.27 (2H, m), 4.58-4.60 (2H, m), 5.15-5.18 (1H, m), 6.67-6.69 (1H, m), 7.50 (1H, dd, J=2.7, 11.0 Hz), 7.53 (1H, d, J=2.7 Hz), 7.62 (1H, d, J=2.7 Hz), 7.65 (1H, dd, J=2.7, 9.0 Hz), 7.80 (1H, d, J=9.0 Hz), 8.08-8.10 (1H, m), 8.53 (1H, s).

ESI-MS (m/e): 436 [M+H]$^+$

Preparation of 5-[2-(1,3-dioxolan-2-yl)ethoxy]-2,3-difluoropyridine

Cesium carbonate (33 g, 100 mmol) and 2-(2-bromoethyl)-1,3-dioxolane (12 g, 67 mmol) were added to an N,N-dimethylformamide suspension (30 ml) of 5,6-difluoropyridin-3-ol (8.8 g, 67 mmol), and stirred at 100° C. for 1 hour. The reaction solution was cooled to room temperature, water was added, and extracted with ethyl acetate. The organic layer was washed with saturated saline water, dried over anhydrous sodium sulfate, and concentrated under reduced pressure. The obtained residue was purified by silica gel column chromatography (hexane:chloroform=1:1 to 0:1) to obtain 5-[2-(1,3-dioxolan-2-yl)ethoxy]-2,3-difluoropyridine (5.9 g, yield: 38%) as a pale yellow oil.

Example 26

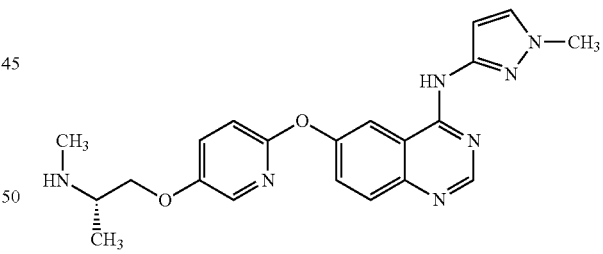

Preparation of 6-[(5-{[(2S)-2-(methylamino)propyl]oxy}pyridin-2-yl)oxy]-N-(1-methyl-1H-pyrazol-3-yl)quinazoline-4-amine 1) (2S)-2-(tetrahydro-2H-pyran-2-yloxy)propyl methanesulfonate (214 mg, 0.90 mmol) and potassium tert-butoxide (200 mg, 1.8 mmol) were added to a dimethyl sulfoxide solution (5 ml) of 6-({4-[(1-methyl-1H-pyrazol-3-yl)amino]quinazolin-6-yl}oxy)pyridin-3-ol (300 mg, 0.90 mmol) obtained in Example 6-3), and the reaction solution was stirred for 24 hours at 100° C. The reaction solution was cooled to room temperature, then water and aqueous 1 N hydrochloric acid solution (0.9 ml, 0.9 mmol) were added, and extracted with ethyl acetate. The organic layer was washed with saturated saline water, then dried over anhydrous sodium sulfate, and concentrated under reduced pressure. The obtained residue was purified by silica gel column chromatography (chloroform:methanol=99:1) to obtain N-(1-methyl-1H-pyrazol-3-yl)-6-[(5-{[(2R)-2-(tetrahydro-2H-pyran-2-yloxy)propyl]oxy}pyridin-2-yl)oxy]quinazoline-4-amine (322 mg, yield: 75%) as a pale brown solid.

2) P-toluenesulfonic acid pyridine salt (17 mg, 0.068 mmol) was added to an ethanol solution (5 ml) of the amine product (322 mg, 0.68 mmol) obtained in the above reaction, and the reaction solution was stirred for 24 hours at 80° C. The reaction solution was cooled to room temperature, then aqueous saturated sodium hydrogencarbonate solution was added, and extracted with a mixed solution of chloroform/methanol (10:1). The organic layer was washed with saturated saline water, dried over anhydrous sodium sulfate, and concentrated under reduced pressure. The obtained residue was purified by silica gel column chromatography (chloroform:methanol=92:8) to obtain (2R)-1-{[6-({4-[(1-methyl-1H-pyrazol-3-yl)amino]quinazolin-6-yl}oxy)pyridin-3-yl]oxy}propan-2-ol (227 mg, yield: 86%) as a pale brown solid.

3) With cooling with ice, triethylamine (0.036 ml, 0.26 mmol) and methanesulfonyl chloride (0.025 ml, 0.21 mmol) were added to a chloroform solution (2 ml) of the alcohol product (42 mg, 0.11 mmol) obtained in the above reaction, and stirred at room temperature for 4 hours. Aqueous saturated sodium hydrogencarbonate solution was added to the reaction solution, and extracted with chloroform. The organic layer was washed with saturated saline water, dried over anhydrous sodium sulfate, and concentrated under reduced pressure. The obtained residue was purified by thin-layer silica gel column chromatography (chloroform:methanol=95:5) to obtain (1R)-1-methyl-2-{[6-({4-[(1-methyl-1H-pyrazol-3-yl)amino]quinazolin-6-yl}oxy)pyridin-3-yl]oxy}ethyl methanesulfonate (18 mg, yield: 36%) as an oil.

4) 2 M methylamine/tetrahydrofuran solution (1 ml) was added to an N,N-dimethylformamide solution (1 ml) of the compound (18 mg, 0.038 mmol) obtained in the above reaction, and stirred at 80° C. in a sealed tube for 2 days. The reaction solution was cooled to room temperature, aqueous saturated sodium hydrogencarbonate solution was added, and extracted with chloroform. The organic layer was washed with saturated saline water, dried over anhydrous sodium sulfate, and concentrated under reduced pressure. The obtained residue was purified by amine-type thin-layer silica gel column chromatography (chloroform:methanol=95:5) to obtain the entitled compound (6 mg, yield: 39%) as a pale yellow amorphous solid.

The analytical data of the entitled compound are shown below.

$^1$HNMR (DMSO-d$_6$) δ: 1.99 (d, 3H, J=8.0 Hz), 2.26 (s, 3H), 2.77-2.82 (m, 1H), 3.13 (s, 3H), 3.77-3.87 (m, 2H), 6.73 (d, 1H, J=4.0 Hz), 7.05 (d, 1H, J=8.0 Hz), 7.50-7.54 (m, 2H), 7.59 (d, 1H, J=4.0 Hz), 7.73 (d, 1H, J=8.0 Hz), 7.85 (d, 1H, J=4.0 Hz), 8.28 (d, 1H, J=4.0 Hz), 8.50 (s, 1H), 10.24 (s, 1H).

ESI-MS (m/e): 406 [M+H]$^+$

Example 27

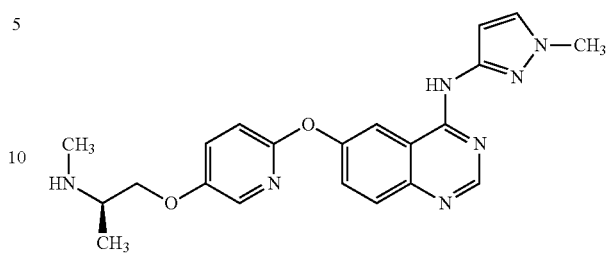

Preparation of 6-[(5-{[(2R)-2-(methylamino)propyl]oxy}pyridin-2-yl)oxy]-N-(1-methyl-1H-pyrazol-3-yl)quinazoline-4-amine Using 6-({4-[(1-methyl-1H-pyrazol-3-yl)amino]quinazolin-6-yl}oxy)pyridin-3-ol obtained in Example 6-3), (2R)-2-(tetrahydro-2H-pyran-2-yloxy)propyl methanesulfonate and 2 M methylamine/tetrahydrofuran solution, and in the same manner as in Example 26 or according to a method similar to it or according to a combination thereof with an ordinary method, the entitled compound (6 mg) was obtained as a pale yellow amorphous solid.

The analytical data of the entitled compound are shown below.

$^1$HNMR (DMSO-d$_6$) δ: 1.99 (d, 3H, J=8.0 Hz), 2.26 (s, 3H), 2.77-2.82 (m, 1H), 3.13 (s, 3H), 3.77-3.87 (m, 2H), 6.73 (d, 1H, J=4.0 Hz), 7.05 (d, 1H, J=8.0 Hz), 7.50-7.54 (m, 2H), 7.59 (d, 1H, J=4.0 Hz), 7.73 (d, 1H, J=8.0 Hz), 7.85 (d, 1H, J=4.0 Hz), 8.28 (d, 1H, J=4.0 Hz), 8.50 (s, 1H), 10.24 (s, 1H).

ESI-MS (m/e): 406 [M+H]$^+$

Example 28

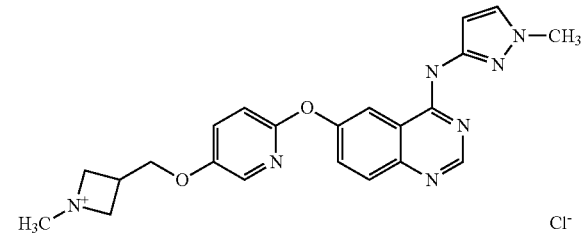

Preparation of 6-({5-[(1-methylazetidin-3-yl)methoxy]pyridin-2-yl}oxy)-N-(1-methyl-1H-pyrazol-3-yl)quinazoline-4-amine hydrochloride 1) Tert-butyl 3-(hydroxymethyl)azetidine-1-carboxylate (110 mg, 0.60 mmol), triphenyl phosphine (160 mg, 0.60 mmol) and diethyl azodicarboxylate (0.095 mmol, 0.60 mmol) were added to a tetrahydrofuran solution (3 ml) of 6-({4-[(1-methyl-1H-pyrazol-3-yl)amino]quinazolin-6-yl}oxy)pyridin-3-ol (100 mg, 0.30 mmol) obtained in Example 6-3), and the reaction solution was stirred at room temperature for 30 minutes. The reaction solution was diluted with chloroform, the organic layer was washed with water and saturated saline water, dried over anhydrous sodium sulfate, and concentrated under reduced pressure. The obtained residue was purified by silica gel column chromatography (chloroform:methanol=96:4) and amine-type silica gel column chromatography (hexane:ethyl acetate=50:50) to obtain tert-butyl 3-({[6-({4-[(1-methyl-1H-pyrazol-3-yl)amino]quinazolin-6-yl}oxy)pyridin-3-yl]oxy}methyl)azetidine-1-carboxylate (136 mg, yield: 90%) as a pale yellow amorphous solid.

2) Using tert-butyl 3-({[6-({4-[(1-methyl-1H-pyrazol-3-yl)amino]quinazolin-6-yl}oxy)pyridin-3-yl]oxy}methyl)azetidine-1-carboxylate obtained in the above reaction and 37% formaldehyde solution, and in the same manner as in Example 25 or according to a method similar to it or according to a combination thereof with an ordinary method, the entitled compound (23 mg) was obtained as a pale yellow amorphous solid.

The analytical data of the entitled compound are shown below.

¹HNMR (DMSO-d₆) δ: 2.80 (s, 3H), 3.12-3.38 (m, 3H), 3.81 (s, 3H), 4.01-4.29 (m, 4H), 6.77 (s, 1H), 7.17 (d, 1H, J=8.8 Hz), 7.60-7.69 (m, 3H), 7.83 (d, 1H, J=9.0 Hz), 7.97 (s, 1H), 8.39 (s, 1H), 8.63 (s, 1H), 10.90-10.66 (m, 2H)

ESI-MS (m/e): 418 [M+H]⁺

Example 29

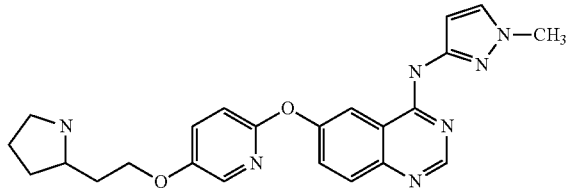 [SMILES: Cn1ccc(Nc2ncnc3ccc(Oc4ccc(OCCC5CCCN5)cn4)cc23)n1]

Preparation of N-(1-methyl-1H-pyrazol-3-yl)-6-{[5-(2-pyrrolidin-2-ylethoxy)pyridin-2-yl]oxy}quinazoline-4-amine 1) Tert-butyl 2-(2-hydroxyethyl)pyrrolidine-1-carboxylate (260 mg, 1.2 mmol), triphenyl phosphine (310 mg, 1.2 mmol) and diethyl azodicarboxylate (0.19 mmol, 1.2 mmol) were added to a tetrahydrofuran solution (6 ml) of 6-({4-[(1-methyl-1H-pyrazol-3-yl)amino]quinazolin-6-yl}oxy)pyridin-3-ol (200 mg, 0.60 mmol) obtained in Example 6, and the reaction solution was stirred at room temperature for 30 minutes. The reaction solution was diluted with chloroform, the organic layer was washed with water and saturated saline water, dried over anhydrous sodium sulfate, and concentrated under reduced pressure. The obtained residue was purified by silica gel column chromatography (chloroform:methanol=96:4) and amine-type silica gel column chromatography (hexane:ethyl acetate=50:50) to obtain tert-butyl 2-(2-{[6-({4-[(1-methyl-1H-pyrazol-3-yl)amino]quinazolin-6-yl}oxy)pyridin-3-yl]oxy}ethyl)pyrrolidine-1-carboxylate (290 mg, yield: 90.5%) as a pale yellow amorphous solid.

2) Trifluoroacetic acid (1.5 ml) was added to a chloroform solution (1.5 ml) of the amine product (87 mg, 0.16 mmol) obtained in the above reaction, and stirred at room temperature for 15 minutes. Saturated sodium hydrogencarbonate was added to the reaction solution, and extracted with a mixed solution of chloroform/methanol (5:1). The organic layer was washed with saturated saline water, dried over anhydrous sodium sulfate, and concentrated under reduced pressure. The obtained residue was purified by silica gel column chromatography (chloroform:methanol=70:30) and amine-type silica gel column chromatography (chloroform:methanol=95:5) to obtain the entitled compound (32 mg, yield: 45%) as a colorless solid.

The analytical data of the entitled compound are shown below.

¹HNMR (DMSO-d₆) δ: 1.20-1.27 (m, 1H), 1.54-1.84 (m, 5H), 2.65-2.71 (m, 1H), 2.77-2.84 (m, 1H), 2.99-3.07 (m, 1H), 3.79 (s, 3H), 4.07 (t, 2H, J=6.7 Hz), 6.78 (d, 1H, J=2.2 Hz), 7.10 (d, 1H, J=8.8 Hz), 7.59-7.52 (m, 2H), 7.64 (d, 1H, J=2.2 Hz), 7.78 (d, 1H, J=9.0 Hz), 7.88 (d, 1H, J=2.9 Hz), 8.33 (d, 1H, J=2.4 Hz), 8.54 (s, 1H), 10.28 (s, 1H)

ESI-MS (m/e): 432 [M+H]⁺

Example 30

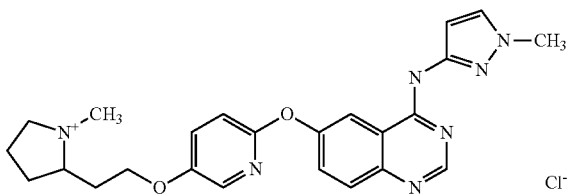 [SMILES: Cn1ccc(Nc2ncnc3ccc(Oc4ccc(OCCC5CCC[NH+]5C)cn4)cc23)n1 ; [Cl-]]

Preparation of N-(1-methyl-1H-pyrazol-3-yl)-6-({5-[2-(1-methylpyrrolidin-2-yl)ethoxy]pyridin-2-yl}oxy)quinazoline-4-amine hydrochloride Using N-(1-methyl-1H-pyrazol-3-yl)-6-{[5-(2-pyrrolidin-2-ylethoxy)pyridin-2-yl]oxy}quinazoline-4-amine obtained in Example 29 and 37% formaldehyde solution, and in the same manner as in Example 28 or according to a method similar to it or according to a combination thereof with an ordinary method, the entitled compound (21 mg) was obtained as a pale yellow amorphous solid.

The analytical data of the entitled compound are shown below.

¹HNMR (DMSO-d₆) δ: 1.68-2.07 (m, 4H), 2.19-2.44 (m, 2H), 2.81 (s, 3H), 3.04 (s, 1H), 3.38 (s, 1H), 3.54 (s, 1H), 3.79 (s, 3H), 4.07-4.20 (m, 2H), 6.79 (s, 1H), 7.14 (d, 1H, J=8.8 Hz), 7.55-7.61 (m, 2H), 7.65 (d, 1H, J=2.2 Hz), 7.79 (d, 1H, J=9.0 Hz), 7.92 (d, 1H, J=3.2 Hz), 8.35 (d, 1H, J=1.7 Hz), 8.56 (s, 1H), 10.30 (s, 2H)

ESI-MS (m/e): 446 [M+H]⁺

Example 31

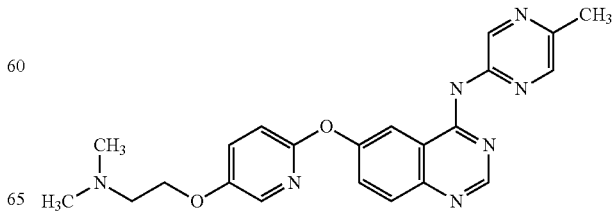

Preparation of 6-({5-[2-(dimethylamino)ethoxy]pyridin-2-yl}oxy)-N-(5-methylpyrazin-2-yl)quinazoline-4-amine 1) 5-(2,2-Diethoxyethoxy)-2-fluoropyridine (680 mg, 3.0 mmol) and potassium tert-butoxide (670 mg, 5.9 mmol) were added to a dimethyl sulfoxide solution (10 ml) of 4-[(5-methylpyrazin-2-yl)amino]quinazolin-6-ol (500 mg, 1.97 mmol), and stirred under a nitrogen atmosphere at 130° C. for 24 hours. The reaction solution was cooled to room temperature, and extracted with a mixed solution of chloroform/methanol (9:1). The organic layer was washed with aqueous saturated ammonium chloride solution and saturated saline water, dried over anhydrous sodium sulfate, and concentrated under reduced pressure. The obtained residue was purified by silica gel column chromatography (chloroform:methanol=95:5) to obtain 6-{[5-(2,2-diethoxyethoxy)pyridin-2-yl]oxy}-N-(5-methylpyrazin-2-yl)quinazoline-4-amine (730 mg, yield: 80%) as a yellow solid.

2) Trifluoroacetic acid (1 ml) and water (0.1 ml) were added to a chloroform solution (1 ml) of the acetal product (90 mg, 0.20 mmol) obtained in the above reaction, and stirred at room temperature for 30 minutes. The reaction solution was concentrated under reduced pressure, then diluted with chloroform and aqueous saturated sodium hydrogencarbonate solution added thereto. The organic layer was washed with saturated saline water, dried over anhydrous sodium sulfate and concentrated under reduced pressure to obtain a crude product of 6-{[5-(formylmethoxy)pyridin-2-yl]oxy}-N-(5-methylpyrazin-2-yl)quinazoline-4-amine.

3) 2 M dimethylamine/tetrahydrofuran solution (0.039 ml, 0.59 mmol) was added to a tetrahydrofuran (2 ml) solution of the crude aldehyde product obtained in the above reaction, then stirred for 30 minutes, and sodium triacetoxyborohydride (125 mg, 0.59 mmol) was added, and further stirred for 1 hour. Aqueous saturated ammonium chloride solution was added to the reaction solution, and extracted with chloroform. The organic layer was washed with water and saturated saline water, dried over anhydrous sodium sulfate, and concentrated under reduced pressure. The obtained residue was purified by amine-type thin-layer silica gel column chromatography (chloroform:methanol=95:5, and hexane:ethyl acetate=75:25) to obtain the entitled compound (27 mg, yield: 33%) as a pale yellow solid.

The analytical data of the entitled compound are shown below.

$^1$HNMR (DMSO-$d_6$) δ: 2.20 (s, 6H), 2.61 (t, 2H, J=5.6 Hz), 3.32 (s, 3H), 4.09 (t, 2H, J=5.6 Hz), 7.12 (d, 1H, J=8.8 Hz), 7.57 (dd, 1H, J=3.4, 8.8 Hz), 7.66 (d, 1H, J=8.8 Hz), 7.86-7.91 (m, 2H), 8.34 (s, 1H), 8.42 (m, 1H), 8.67 (s, 1H), 9.43 (s, 1H), 10.46 (s, 1H)

ESI-MS (m/e): 418 [M+H]$^+$

Example 32

Preparation of 6-({3-chloro-5-[2-(methylamino)ethoxy]pyridin-2-yl}oxy)-N-(5-methylpyrazin-2-yl)quinazoline-4-amine hydrochloride 1) 3-Chloro-5-(2,2-diethoxyethoxy)-2-fluoropyridine (460 mg, 1.74 mmol) and potassium tert-butoxide (160 mg, 1.4 mmol) were added to an N,N-dimethylacetamide suspension (0.9 ml) of 4-[(5-methylpyrazin-2-yl)amino]quinazolin-6-ol (180 mg, 0.71 mmol), and reacted under a nitrogen atmosphere at 200° C. for 30 minutes, using microwaves. The reaction solution was cooled to room temperature, then diluted with chloroform. The organic layer was washed with water and saturated saline water, dried over anhydrous sodium sulfate, and concentrated under reduced pressure. The obtained residue was purified by silica gel column chromatography (chloroform:methanol=96:4) and amine-type silica gel column chromatography (hexane:ethyl acetate=50:50) to obtain 6-{[3-chloro-5-(2,2-diethoxyethoxy)pyridin-2-yl]oxy}-N-(5-methylpyrazin-2-yl)quinazoline-4-amine (187 mg, yield: 53%) as a pale yellow solid.

2) Trifluoroacetic acid (2 ml) and water (0.2 ml) were added to a chloroform solution (2 ml) of the acetal product (100 mg, 0.20 mmol) obtained in the above reaction, and stirred at room temperature for 1 hour. The reaction solution was diluted with a mixed solution of chloroform/methanol (9:1). The organic layer was washed with aqueous saturated sodium hydrogencarbonate solution and saturated saline water, then dried over anhydrous sodium sulfate, and concentrated under reduced pressure to obtain a crude product of 6-{[3-chloro-5-(formylmethoxy)pyridin-2-yl]oxy}-N-(5-methylpyrazin-2-yl)quinazoline-4-amine.

3) 2 M methylamine/tetrahydrofuran solution (0.022 ml, 0.20 mmol) was added to a tetrahydrofuran (2 ml) solution of the crude aldehyde product obtained in the above reaction, then stirred for 30 minutes, and sodium triacetoxyborohydride (63 mg, 0.30 mmol) was added, and further stirred for 1 hour. 1 N sodium hydroxide was added to the reaction solution, and extracted with a mixed solution of chloroform/methanol (9:1). The organic layer was washed with saturated saline water, dried over anhydrous sodium sulfate, and concentrated under reduced pressure. The obtained residue was purified by thin-layer silica gel chromatography (chloroform:methanol=90:10) and amine-type thin-layer silica gel chromatography (chloroform:methanol=98:2) to obtain 6-({3-chloro-5-[2-(methylamino)ethoxy]pyridin-2-yl}oxy)-N-(5-methylpyrazin-2-yl)quinazoline-4-amine. This was dissolved in methanol, aqueous 5 M hydrochloric acid solution (0.0075 ml, 0.038 mmol) was added, and concentrated under reduced pressure to obtain the entitled compound (18 mg, yield: 38%) as a pale yellow solid.

The analytical data of the entitled compound are shown below.

$^1$HNMR (DMSO-$d_6$) δ: 2.49 (s, 3H), 2.61 (t, 3H, J=5.4 Hz), 3.32 (t, 2H, J=5.1 Hz), 4.35 (t, 2H, J=5.0 Hz), 7.78 (d, 1H, J=9.3 Hz), 7.90-7.96 (m, 3H), 8.38 (s, 1H), 8.48 (s, 1H), 8.75 (s, 1H), 8.99 (s, 2H), 9.34 (s, 1H)

ESI-MS (m/e): 438 [M+H]$^+$

Preparation of 3-chloro-5-(2,2-diethoxyethoxy)-2-fluoropyridine

Cesium carbonate (2.9 g, 8.9 mmol) and 2-(2-bromoethyl)-1,3-dioxolane (990 mg, 5.0 mmol) were added to an N,N-dimethylformamide suspension (10 ml) of 5-chloro-6-fluoropyridin-3-ol (570 mg, 3.9 mmol), and stirred at 100° C. for 4 hours. The reaction solution was cooled to room temperature, water was added, and extracted with ethyl acetate. The

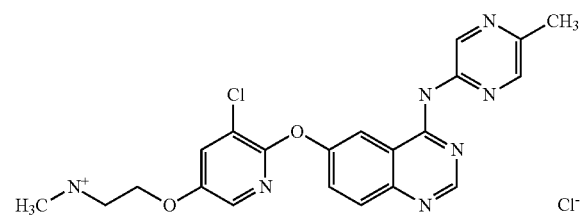

organic layer was washed with water and saturated saline water, dried over anhydrous sodium sulfate, and concentrated under reduced pressure. The obtained residue was purified by silica gel column chromatography (hexane:ethyl acetate=70:30) to obtain 3-chloro-5-(2,2-diethoxyethoxy)-2-fluoropyridine (640 mg, yield: 62%) as a colorless oil.

Example 33

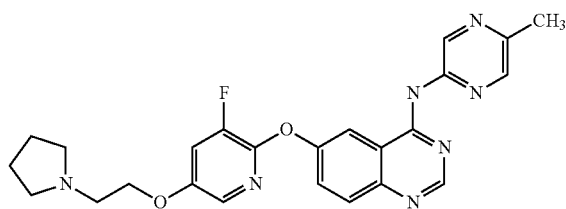 [SMILES: Cc1cnc(Nc2ncnc3ccc(Oc4ncc(OCCN5CCCC5)cc4F)cc23)cn1]

Preparation of 6-{[3-fluoro-5-(2-pyrrolidin-1-ylethoxy)pyridin-2-yl]oxy}-N-(5-methylpyrazin-2-yl)quinazoline-4-amine Using 4-[(5-methylpyrazin-2-yl)amino]quinazoline-6-ol, 5-(2,2-diethoxyethoxy)-2,3-difluoropyridine and pyrrolidine, and in the same manner as in Example 31 or according to a method similar to it or according to a combination thereof with an ordinary method, the entitled compound (27 mg) was obtained as a pale yellow solid.

The analytical data of the entitled compound are shown below.

$^1$HNMR (DMSO-d$_6$) δ: 1.66-1.68 (m, 4H), 2.49 (s, 3H), 2.78 (t, 2H, J=5.6 Hz), 3.29-3.31 (m, 4H), 4.15 (t, 2H, J=5.6 Hz), 7.76-7.80 (m, 4H), 7.89 (d, 1H, J=9.3 Hz), 8.35-8.38 (m, 2H) 8.67 (s, 1H), 9.43 (s, 1H), 10.44 (s, 1H)

ESI-MS (m/e): 462 [M+H]$^+$

Example 34

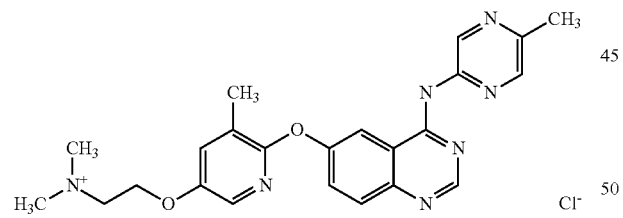

Preparation of 6-({5-[2-(dimethylamino)ethoxy]-3-methylpyridin-2-yl}oxy)-N-(5-methylpyrazin-2-yl)quinazoline-4-amine hydrochloride 1) Potassium tert-butoxide (443 mg, 3.95 mmol) and 5-(2,2-diethoxyethoxy)-2-fluoro-3-methylpyridine (1.06 g, 4.34 mmol) were added to an N,N-dimethylacetamide solution (1.25 ml) of 4-[(5-methylpyrazol-2-yl)amino]quinazolin-6-ol (500 mg, 1.97 mmol), then stirred for 15 hours under a nitrogen atmosphere at 190° C. in a sealed tube. The reaction solution was cooled with ice, water was added, and extracted with chloroform/methanol (10:1). The organic layer was washed with water, dried over anhydrous sodium sulfate, and concentrated under reduced pressure. The obtained residue was purified by amine-type silica gel column chromatography (Moritex NH, hexane:ethyl acetate=7:2 to 3:2) to obtain 6-{[5-(2,2-diethoxyethoxy)-3-methylpyridin-2-yl]oxy}-N-(5-methylpyrazin-2-yl)quinazoline-4-amine (303 mg, yield: 32%) as an orange solid.

2) Using 6-{[5-(2,2-diethoxyethoxy)-3-methylpyridin-2-yl]oxy}-N-(5-methylpyrazin-2-yl)quinazoline-4-amine obtained in the above reaction and 2 M methylamine/tetrahydrofuran solution, and in the same manner as in Example 31 and Example 33 or according to a method similar to it or according to a combination thereof with an ordinary method, the entitled compound (30 mg) was obtained as an orange solid.

The analytical data of the entitled compound are shown below.

$^1$H-NMR (DMSO-d$_6$) δ: 2.36 (3H, s), 2.54 (3H, s), 2.83-2.84 (6H, m), 3.49-3.53 (2H, m), 4.42 (2H, t, J=5.1 Hz), 7.61 (1H, d, J=2.0 Hz), 7.80 (1H, d, J=2.9 Hz), 7.85 (1H, d, J=9.3 Hz), 8.02 (1H, d, J=9.3 Hz), 8.47 (1H, s), 8.53 (1H, s), 8.91 (1H, s), 9.24 (1H, s), 10.63 (1H, brs).

ESI-MS (m/e): 432 [M+H]$^+$

Preparation of 5-(2,2-diethoxyethoxy)-2-fluoro-3-methylpyridine

1) Hydrogen peroxide water (4.37 ml, 42.8 mmol) was added to a tetrahydrofuran solution (50 ml) of 2-fluoro-3-methylpyridine-5-boronic acid (5.1 g, 32.9 mmol), and stirred overnight at room temperature. Water was added to the reaction solution, and extracted with ethyl acetate. The organic layer was washed with aqueous 5% sodium thiosulfate solution and saturated saline water, dried over anhydrous sodium sulfate, and concentrated under reduced pressure to obtain 6-fluoro-5-methylpyridin-3-ol (4.03 g, yield: 96%) as a pale yellow solid.

2) Bromoacetaldehyde diethyl acetal (5.68 ml, 37.8 mmol) and cesium carbonate (25.6 g, 79.0 mmol) were added to an N,N-dimethylacetamide solution (40 ml) of the phenol product (4.0 g, 31.5 mmol) obtained in the above reaction, and stirred under a nitrogen atmosphere at 100° C. for 4 hours. The reaction solution was cooled with ice, and diluted with water and ethyl acetate. The organic layer was washed with water and saturated saline water, dried over anhydrous sodium sulfate, and concentrated under reduced pressure. The obtained residue was purified by silica gel column chromatography (Moritex, hexane:ethyl acetate=19:1 to 7:1) to obtain 5-(2,2-diethoxyethoxy)-2-fluoro-3-methylpyridine (7.28 g, yield: 95%) as a pale yellow oil.

Example 35

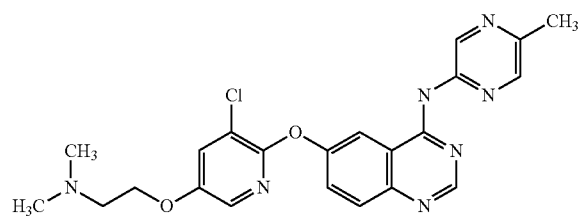

Preparation of 6-({3-chloro-5-[2-(dimethylamino)ethoxy]pyridin-2-yl}oxy)-N-(5-methylpyrazin-2-yl)quinazoline-4-amine Using 4-[(5-methylpyrazin-2-yl)amino]quinazolin-6-ol, 3-chloro-5-(2,2-diethoxyethoxy)-2-fluoropyridine and 2 M dimethylamine/tetrahydrofuran solution, and in the same manner as in Example 32 or according to a method similar to it or according to a combination thereof with an ordinary method, the entitled compound (14 mg) was obtained as a pale yellow amorphous solid.

The analytical data of the entitled compound are shown below.

$^1$HNMR (DMSO-d$_6$) δ: 2.19 (s, 6H), 2.60 (t, 2H, J=5.6 Hz), 3.32 (s, 3H), 4.13 (t, 2H, J=5.9 Hz), 7.71 (d, 1H, J=7.8 Hz), 7.89 (t, 3H, J=3.2 Hz), 8.34 (s, 1H), 8.41 (s, 1H), 8.68 (s, 1H), 9.43 (s, 1H), 10.44 (s, 1H)

ESI-MS (m/e): 452 [M+H]$^+$

Example 36

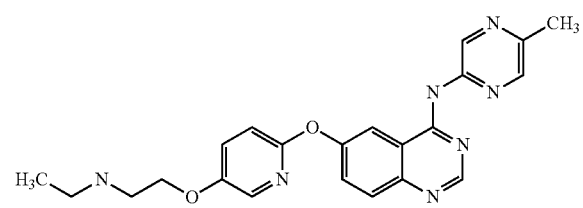 [SMILES: CCNCCOc1ccc(Oc2ccc3ncnc(Nc4cnc(C)cn4)c3c2)nc1]

Preparation of 6-({5-[2-(ethylamino)ethoxy]pyridin-2-yl}oxy)-N-(5-methylpyrazin-2-yl)quinazoline-4-amine Using 4-[(5-methylpyrazin-2-yl)amino]quinazolin-6-ol, 5-(2,2-diethoxyethoxy)-2-fluoropyridine and 2 Methylamine/tetrahydrofuran solution, and in the same manner as in Example 31 or according to a method similar to it or according to a combination thereof with an ordinary method, the entitled compound (52 mg) was obtained as a pale yellow amorphous solid.

The analytical data of the entitled compound are shown below.

$^1$HNMR (CDCl$_3$) δ: 1.12 (t, 3H, J=8.0 Hz), 2.51, 2.52 (s, 6H), 2.68-2.74 (m, 2H), 2.98-3.01 (m, 2H), 4.06-4.08 (m, 2H), 6.92-6.97 (m, 1H), 7.31-7.35 (m, 1H), 7.43-7.46 (m, 0.5H), 7.58-7.61 (m, 0.5H), 7.65-7.67 (m, 1H), 7.83-7.85 (m, 1H), 7.95 (d, 0.5H, J=8.0 Hz), 8.00 (s, 0.5H), 8.08 (s, 0.5H), 8.10 (s, 0.5H), 8.21 (d, 0.5H, J=4.0 Hz), 8.51 (s, 0.5H), 8.81 (s, 0.5H), 9.86 (s, 0.5H).

ESI-MS (m/e): 418 [M+H]$^+$

Example 37

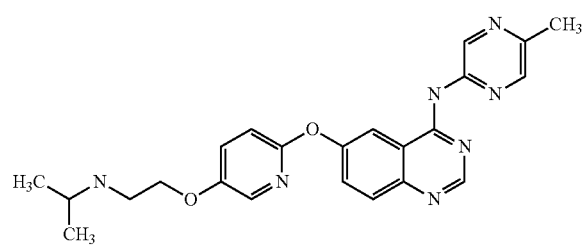 [SMILES: Cc1cnc(Nc2ncnc3ccc(Oc4ccc(OCCNC(C)C)cn4)cc23)cn1]

Preparation of 6-({5-[2-(isopropylamino)ethoxy]pyridin-2-yl}oxy)-N-(5-methylpyrazin-2-yl)quinazoline-4-amine Using 4-[(5-methylpyrazin-2-yl)amino]quinazolin-6-ol, 5-(2,2-diethoxyethoxy)-2-fluoropyridine and isopropylamine, and in the same manner as in Example 31 or according to a method similar to it or according to a combination thereof with an ordinary method, the entitled compound (62 mg) was obtained as a pale yellow solid.

The analytical data of the entitled compound are shown below.

$^1$HNMR (DMSO-d$_6$) δ: 0.96 (s, 6H), 2.48-2.49 (m, 3H), 2.66-2.79 (m, 1H), 2.85 (t, 2H, J=5.8 Hz), 4.04 (t, 2H, J=5.8 Hz), 7.12 (d, 1H, J=8.8 Hz), 7.57 (dd, 1H, J=2.9, 8.8 Hz), 7.65 (dd, 1H, J=2.2, 8.8 Hz), 7.85 (d, 1H, J=8.8 Hz), 7.90 (d, 1H, J=2.9 Hz), 8.34 (s, 1H), 8.39 (s, 1H), 8.63 (s, 1H), 9.40 (s, 1H)

ESI-MS (m/e): 432 [M+H]$^+$

Example 38

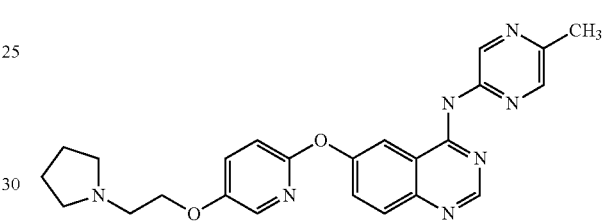

Preparation of N-(5-methylpyrazin-2-yl)-6-{[5-(2-pyrrolidin-1-ylethoxy)pyridin-2-yl]oxy}quinazoline-4-amine The compound of Example 38 was obtained as follows: Using 4-[(5-methylpyrazin-2-yl)amino]quinazolin-6-ol, 5-(2,2-diethoxyethoxy)-2-fluoropyridine and pyrrolidine, and in the same manner as in Example 31 or according to a method similar to it or according to a combination thereof with an ordinary method, the entitled compound (11 mg) was obtained as a pale yellow solid.

The analytical data of the entitled compound are shown below.

$^1$HNMR (DMSO-d$_6$) δ: 1.66-1.68 (m, 4H), 2.49 (s, 3H), 2.77-2.79 (m, 2H), 3.29-3.31 (m, 4H), 4.11 (t, 2H, J=5.9 Hz), 7.12 (d, 1H, J=8.8 Hz), 7.57 (dd, 1H, J=3.2, 8.8 Hz), 7.66 (d, 1H, J=8.8 Hz), 7.87-7.90 (m, 2H), 8.35 (s, 1H), 8.42 (s, 1H), 8.67 (s, 1H), 9.43 (s, 1H), 10.45 (s, 1H)

ESI-MS (m/e): 444 [M+H]$^+$

Example 39

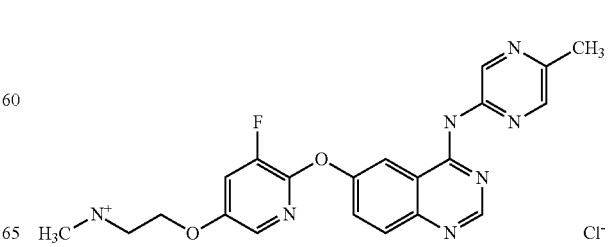

Preparation of 6-({3-fluoro-5-[2-(methylamino) ethoxy]pyridin-2-yl}oxy)-N-(5-methylpyrazin-2-yl) quinazoline-4-amine hydrochloride Using 4-[(5-methylpyrazin-2-yl)amino]quinazolin-6-ol, 5-(2,2-diethoxyethoxy)-2,3-difluoropyridine and 2 M methylamine/tetrahydrofuran solution, and in the same manner as in Example 32 or according to a method similar to it or according to a combination thereof with an ordinary method, the entitled compound (36 mg) was obtained as a pale yellow solid.

The analytical data of the entitled compound are shown below.

$^1$HNMR (DMSO-$d_6$) δ: 2.48 (s, 3H), 2.61 (s, 3H), 3.30-3.32 (m, 2H), 4.35 (t, 2H, J=4.9 Hz), 7.74 (dd, 1H, J=9.0, 2.4 Hz), 7.80-7.86 (m, 2H), 7.90 (d, 1H, J=9.0 Hz), 8.35 (s, 1H), 8.44 (d, 1H, J=2.4 Hz), 8.69 (s, 1H), 8.99 (brs, 2H), 9.43 (s, 1H), 10.45 (s, 1H)

ESI-MS (m/e): 422 [M+H]$^+$

Example 40

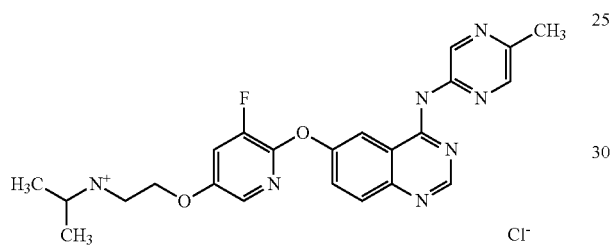

Preparation of 6-({3-fluoro-5-[2-(isopropylamino) ethoxy]pyridin-2-yl}oxy)-N-(5-methylpyrazin-2-yl) quinazoline-4-amine hydrochloride Using 4-[(5-methylpyrazin-2-yl)amino]quinazolin-6-ol, 5-(2,2-diethoxyethoxy)-2,3-difluoropyridine and isopropylamine, and in the same manner as in Example 32 or according to a method similar to it or according to a combination thereof with an ordinary method, the entitled compound (36 mg) was obtained as a yellow solid.

The analytical data of the entitled compound are shown below.

$^1$HNMR (DMSO-$d_6$) δ: 1.26 (d, 6H, J=6.6 Hz), 2.48-2.50 (m, 3H), 3.30-3.44 (m, 3H), 4.34 (t, 2H, J=5.0 Hz), 7.71-7.95 (m, 4H), 8.36 (s, 1H), 8.42-8.49 (m, 1H), 8.68-8.83 (m, 3H), 9.38-9.44 (m, 1H)

ESI-MS (m/e): 450 [M+H]$^+$

Example 41

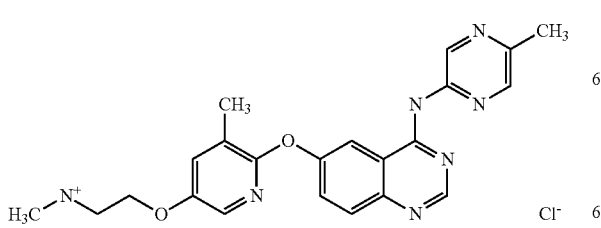

Preparation of 6-({3-methyl-5-[2-(methylamino) ethoxy]pyridin-2-yl}oxy)-N-(5-methylpyrazin-2-yl) quinazoline-4-amine hydrochloride Using 4-[(5-methylpyrazin-2-yl)amino]quinazolin-6-ol, 5-(2,2-diethoxyethoxy)-2,3-difluoropyridine and 2 M methylamine/tetrahydrofuran solution, and in the same manner as in Example 32 and Example 34 or according to a method similar to it or according to a combination thereof with an ordinary method, the entitled compound (29 mg) was obtained as an orange solid.

The analytical data of the entitled compound are shown below.

$^1$H-NMR (DMSO-$d_6$) δ: 2.37 (3H, s), 2.49-2.51 (3H, m), 2.61-2.63 (3H, m), 3.30-3.35 (2H, m), 4.30 (2H, t, J=5.1 Hz), 7.57 (1H, d, J=2.0 Hz), 7.73-7.78 (2H, m), 7.93 (1H, d, J=8.8 Hz), 8.40-8.44 (2H, m), 8.76 (1H, brs), 9.04 (2H, brs), 9.33 (1H, brs).

ESI-MS (m/e): 418 [M+H]$^+$

Example 42

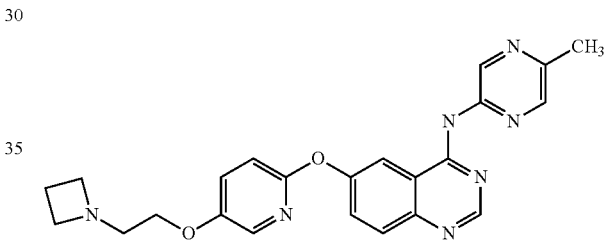

Preparation of 6-{[5-(2-azetidin-1-ylethoxy)pyridin-2-yl]oxy}-N-(5-methylpyrazin-2-yl)quinazoline-4-amine Using 4-[(5-methylpyrazin-2-yl)amino]quinazolin-6-ol, 5-(2,2-diethoxyethoxy)-2-fluoropyridine and azetidine, and in the same manner as in Example 31 or according to a method similar to it or according to a combination thereof with an ordinary method, the entitled compound (22 mg) was obtained as a pale yellow solid.

The analytical data of the entitled compound are shown below.

$^1$HNMR (DMSO-$d_6$) δ: 1.91-1.98 (m, 2H), 2.49 (s, 3H), 2.68 (t, 2H, J=5.6 Hz), 3.14-3.17 (m, 4H), 3.95 (t, 2H, J=5.6 Hz), 7.11 (d, 1H, J=8.8 Hz), 7.54 (dd, 1H, J=2.9, 8.8 Hz), 7.66 (d, 1H, J=7.8 Hz), 7.87-7.88 (m, 2H), 8.41 (s, 1H), 8.67 (s, 1H), 9.42 (s, 1H), 10.45 (s, 1H)

ESI-MS (m/e): 430 [M+H]$^+$

Example 43

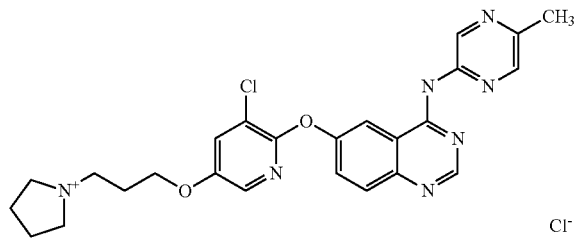 [SMILES: Cc1cnc(Nc2ncnc3ccc(Oc4ncc(OCCC[NH+]5CCCC5)cc4Cl)cc23)cn1 ; [Cl-]]

Preparation of 6-{[3-chloro-5-(3-pyrrolidin-1-ylpropoxy)pyridin-2-yl]oxy}-N-(5-methylpyrazin-2-yl)quinazoline-4-amine hydrochloride 1) Potassium tert-butoxide (0.89 g, 7.90 mmol) and 3-chloro-2-fluoro-5-[3-(tetrahydro-2H-pyran-2-yloxy)propoxy]pyridine (2.52 g, 8.69 mmol) were added to an N,N-dimethylacetamide solution (2.5 ml) of 4-[(5-methylpyrazin-2-yl)amino]quinazolin-6-ol (1.0 g, 3.95 mmol), and stirred at 180° C. for 14 hours under a nitrogen atmosphere in a sealed tube. The reaction solution was cooled with ice, water was added, and extracted with chloroform/methanol (10:1). The organic layer was washed with water, dried over anhydrous sodium sulfate, and concentrated under reduced pressure. The obtained residue was purified by amine-type silica gel column chromatography (Moritex NH, hexane:ethyl acetate=3:1 to 3:2) to obtain 6-({3-chloro-5-[3-(tetrahydro-2H-pyran-2-yloxy)propoxy]pyridin-2-yl}oxy)-N-(5-methylpyrazin-2-yl)quinazoline-4-amine (1.46 g, yield: 71%) as an orange oil.

2) Pyridinium p-toluenesulfonate (1.40 g, 5.58 mmol) was added to an ethanol solution (15 ml) of the compound (1.46 g, 2.79 mmol) obtained in the above reaction, and stirred under reflux for 2 hours. The reaction solution was cooled to room temperature, water was added, and extracted with chloroform. The organic layer was washed with saturated saline water, dried over anhydrous sodium sulfate, and concentrated under reduced pressure. The obtained residue was purified by amine-type silica gel column chromatography (Moritex NH, ethyl acetate:chloroform:methanol=100:20:2) to obtain 3-{[5-chloro-6-({4-[(5-methylpyrazin-2-yl)amino]quinazolin-6-yl}oxy)pyridin-3-yl]oxy}propan-1-ol (830 mg, yield: 68%) as a pale yellow solid.

3) Triethylamine (0.78 ml, 5.56 mmol) and methanesulfonyl chloride (0.29 ml, 3.70 mmol) were added to a chloroform solution (10 ml) of the hydroxy product (813 mg, 1.85 mmol) obtained in the above reaction, and stirred at room temperature for 35 minutes. Water was added to the reaction solution, and extracted with chloroform/methanol (10:1). The organic layer was dried over anhydrous sodium sulfate, then concentrated under reduced pressure to obtain a crude product (1.03 g) containing 3-{[5-chloro-6-({4-[(5-methylpyrazin-2-yl)amino]quinazolin-6-yl}oxy)pyridin-3-yl]oxy}propyl methanesulfonate as a pale orange amorphous solid.

4) Pyrrolidine (0.73 ml, 8.82 mmol) was added to a tetrahydrofuran solution (5 ml) of the methanesulfonate product (98 mg) obtained in the above reaction, and stirred under a nitrogen atmosphere at 55° C. for 3 days. Saturated saline water was added to the reaction solution, and extracted with chloroform/methanol (10:1). The organic layer was dried over anhydrous sodium sulfate, and concentrated under reduced pressure. The obtained residue was purified by amine-type thin-layer chromatography (hexane:ethyl acetate:chloroform=2:7:1) and thin-layer chromatography (chloroform:methanol=9:1) to obtain 6-{[3-chloro-5-(3-pyrrolidin-1-ylpropoxy)pyridin-2-yl]oxy}-N-(5-methylpyrazin-2-yl)quinazoline-4-amine (48 mg, yield: 55%, 2 steps) as a yellow amorphous solid.

5) 5 N hydrochloric acid (0.019 ml, 0.096 mmol) was added to a methanol solution (1 ml) of the pyrrolidine product (47 mg, 0.096 mmol) obtained in the above reaction, and stirred at room temperature for 5 minutes. The reaction solution was concentrated under reduced pressure to obtain the entitled compound (56 mg) as a yellow solid.

The analytical data of the entitled compound are shown below.

$^1$H-NMR (DMSO-d$_6$) δ: 1.88-1.89 (2H, m), 2.13-2.19 (2H, m), 2.50-2.51 (5H, m), 2.95-3.03 (2H, m), 3.23-3.29 (2H, m), 3.51-3.57 (2H, m), 4.19 (2H, t, J=5.9 Hz), 7.81 (1H, d, J=9.3 Hz), 7.89-7.97 (3H, m), 8.41 (1H, brs), 8.48 (1H, s), 8.79 (1H, s), 9.33 (1H, brs), 10.74 (1H, brs).

ESI-MS (m/e): 492 [M+H]$^+$

Preparation of 3-chloro-2-fluoro-5-[3-(tetrahydro-2H-pyran-2-yloxy)propoxy]pyridine 2-(3-Bromopropoxy)tetrahydro-2H-pyran (12.93 g, 57.9 mmol) and cesium carbonate (39.5 g, 121.0 mmol) were added to an N,N-dimethylacetamide solution (80 ml) of 5-chloro-6-fluoropyridin-3-ol (8.14 g, 55.2 mmol), and stirred overnight under a nitrogen atmosphere at 100° C. The reaction solution was cooled with ice, water was added, and extracted with ethyl acetate. The organic layer was washed with water and saturated saline water, dried over anhydrous sodium sulfate, and concentrated under reduced pressure. The obtained residue was purified by amine-type silica gel column chromatography (Moritex NH, hexane:ethyl acetate=18:1 to 11:1) to obtain 3-chloro-2-fluoro-5-[3-(tetrahydro-2H-pyran-2-yloxy)propoxy]pyridine (10.84 g, yield: 68%) as a pale yellow oil.

Example 44

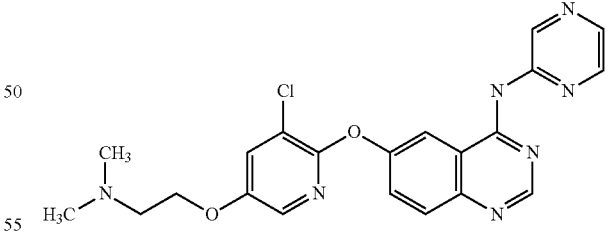

Preparation of 6-({3-chloro-5-[2-(dimethylamino)ethoxy]pyridin-2-yl}oxy)-N-pyrazin-2-ylquinazoline-4-amine 1) 2,3-Dichloro-5-(2,2-diethoxyethoxy)pyridine (810 mg, 2.9 mmol) and potassium tert-butoxide (350 mg, 3.1 mmol) were added to an N,N-dimethylacetamide suspension (3 ml) of 4-(pyrazin-2-ylamino)quinazolin-6-ol (300 mg, 1.25 mmol), and stirred for 24 hours in a sealed tube at 200° C. The reaction solution was cooled to room temperature, aqueous saturated ammonium chloride solution was added, filtered, and washed with a mixed solution of chloroform/methanol (9:1). The obtained filtrate was extracted with chloroform, the organic layer was washed with water and saturated saline water, dried over anhydrous sodium sulfate, and concentrated under reduced pressure. The obtained residue was purified by reversed-phase liquid chromatography (YMC CombiPrep Pro C18 AS-360-cc) to obtain 6-{[3-chloro-5-(2,2-diethoxyethoxy)pyridin-2-yl]oxy}-N-pyrazin-2-ylquinazoline-4-amine (60 mg, yield: 10%) as a pale yellow solid.

2) Trifluoroacetic acid (2 ml) and water (0.2 ml) were added to a chloroform solution (2 ml) of the acetal product (60 mg, 0.12 mmol) obtained in the above reaction, and stirred at room temperature for 30 minutes. The reaction solution was diluted with chloroform, the organic layer was washed with aqueous saturated sodium hydrogencarbonate solution and saturated saline water, dried over anhydrous sodium sulfate, and concentrated under reduced pressure to obtain a crude product of 6-{[3-chloro-5-(formylmethoxy)pyridin-2-yl]oxy}-N-pyrazin-2-ylquinazoline-4-amine.

3) 2 M dimethylamine/tetrahydrofuran solution (0.010 ml, 0.15 mmol) was added to a tetrahydrofuran (2 ml) solution of the crude aldehyde product obtained in the above reaction, stirred for 30 minutes, and then sodium triacetoxyborohydride (16 mg, 0.073 mmol) was added, and further stirred for 10 minutes. Aqueous saturated ammonium chloride solution was added to the reaction solution, and extracted with chloroform. The organic layer was washed with water and saturated saline water, dried over anhydrous sodium sulfate, and concentrated under reduced pressure. The obtained residue was purified by amine-type thin-layer silica gel column chromatography (chloroform:methanol=95:5 and hexane:ethyl acetate=75:25) to obtain the entitled compound (13 mg, yield: 41%) as a pale yellow solid.

The analytical data of the entitled compound are shown below.

$^1$HNMR (DMSO-$d_6$) δ: 2.18 (s, 6H), 2.61 (t, 2H, J=5.8 Hz), 4.08 (t, 2H, J=5.8 Hz), 7.73 (d, 1H, J=10.8 Hz), 7.82-7.92 (m, 3H), 8.36 (s, 1H), 8.44 (d, 2H, J=10.8 Hz), 8.72 (s, 1H), 9.59 (s, 1H), 10.56 (s, 1H)

ESI-MS (m/e): 438 [M+H]$^+$

Example 45

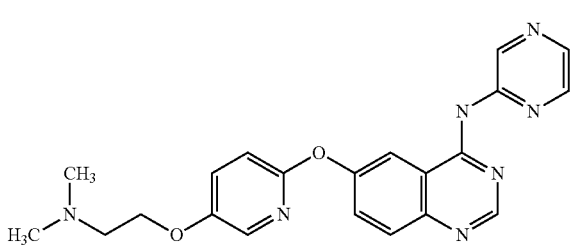 [SMILES: CN(C)CCOc1ccc(Oc2ccc3ncnc(Nc4cnccn4)c3c2)nc1]

Preparation of 6-({5-[2-(dimethylamino)ethoxy]pyridin-2-yl}oxy)-N-pyrazin-2-ylquinazoline-4-amine Using 4-(pyrazin-2-ylamino)quinazolin-6-ol, 5-(2,2-diethoxyethoxy)-2-fluoropyridine and 2 M dimethylamine/tetrahydrofuran solution, and in the same manner as in Example 31 or according to a method similar to it or according to a combination thereof with an ordinary method, the entitled compound (13 mg) was obtained as a pale yellow amorphous solid.

The analytical data of the entitled compound are shown below.

$^1$HNMR (DMSO-$d_6$) δ: 2.19 (s, 6H), 2.61 (t, 2H, J=5.8 Hz), 4.13 (t, 2H, J=5.8 Hz), 7.13 (d, 1H, J=8.8 Hz), 7.57 (dd, 1H, J=3.2, 8.8 Hz), 7.67 (d, 1H, J=8.8 Hz), 7.82-7.91 (m, 2H), 8.31-8.45 (m, 2H), 8.70 (s, 1H), 9.59 (s, 1H), 10.58 (s, 1H)

ESI-MS (m/e): 404 [M+H]$^+$

Example 46

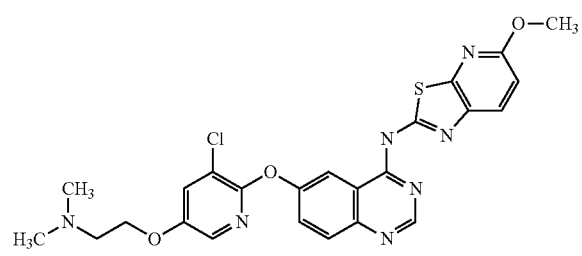

Preparation of 6-({3-chloro-5-[2-(dimethylamino)ethoxy]pyridin-2-yl}oxy)-N-(5-methoxy[1,3]thiazolo[5,4-b]pyridin-2-yl)quinazoline-4-amine 1) 2,3-Dichloro-5-(2,2-diethoxyethoxy)pyridine (240 mg, 0.85 mmol) and potassium tert-butoxide (100 mg, 0.92 mmol) were added to an N,N-dimethylacetamide suspension (1 ml) of 4-[(5-methoxy[1,3]thiazolo[5,4-b]pyridin-2-yl)amino]quinazolin-6-ol (120 mg, 0.37 mmol), and stirred for 24 hours at 200° C. in a sealed tube. The reaction solution was cooled to room temperature, then aqueous saturated ammonium chloride solution was added, filtered, and washed with a mixed solution of chloroform/methanol (9:1). The obtained filtrate was extracted with chloroform, the organic layer was washed with water and saturated saline water, dried over anhydrous sodium sulfate, and concentrated under reduced pressure. The obtained residue was purified by reversed-phase liquid chromatography (YMC CombiPrep Pro C18 AS-360-cc) to obtain 6-{[3-chloro-5-(2,2-diethoxyethoxy)pyridin-2-yl]oxy}-N-(5-methoxy[1,3]thiazolo[5,4-b]pyridin-2-yl)quinazoline-4-amine (5 mg, yield: 2%) as a pale yellow solid.

2) Trifluoroacetic acid (2 ml) and water (0.2 ml) were added to a chloroform solution (2 ml) of the acetal product (5 mg, 0.009 mmol) obtained in the above reaction, and stirred at room temperature for 30 minutes. The reaction solution was diluted with chloroform, the organic layer was washed with aqueous saturated sodium hydrogencarbonate solution and saturated saline water, dried over anhydrous sodium sulfate, and concentrated under reduced pressure to obtain a crude product of 6-{[3-chloro-5-(formylmethoxy)pyridin-2-yl]oxy}-N-(5-methoxy[1,3]thiazolo[5,4-b]pyridin-2-yl)quinazoline-4-amine 3) 2 M dimethylamine/tetrahydrofuran solution (0.001 ml, 0.009 mmol) was added to a tetrahydrofuran (2 ml) solution of the crude aldehyde product obtained in the above reaction, stirred for 30 minutes, and then sodium triacetoxyborohydride (2 mg, 0.009 mmol) was added, and further stirred for 10 minutes. Aqueous saturated ammonium chloride solution was added to the reaction solution, and extracted with chloroform. The organic layer was washed with water and saturated saline water, dried over anhydrous sodium sulfate, and concentrated under reduced pressure. The obtained residue was purified by amine-type thin-layer silica gel column chromatography (chloroform:methanol=95:5 and hexane:ethyl acetate=75:25) to obtain the entitled compound (2 mg, yield: 44%) as a pale yellow solid.

The analytical data of the entitled compound are shown below.

$^1$HNMR (DMSO-$d_6$) δ: 2.35 (s, 6H), 2.74 (t, 2H, J=5.1 Hz), 4.00 (s, 3H), 4.09 (t, 2H, J=5.1 Hz), 6.82 (d, 1H, J=8.8 Hz), 7.48 (d, 1H, J=2.4 Hz), 7.58 (s, 1H), 7.78 (q, 2H, J=2.9 Hz), 7.90 (t, 1H, J=5.4 Hz), 8.19 (s, 1H), 8.24 (d, 1H, J=2.9 Hz)

ESI-MS (m/e): 524 [M+H]$^+$

Preparation of 4-[(5-methoxy[1,3]thiazolo[5,4-b]pyridin-2-yl)amino]quinazolin-6-ol 1) Cesium carbonate (880 mg, 2.7 mmol) and 1,1'-binaphthalene-2,2'-diylbis(diphenylphosphine) (168 mg, 0.27 mmol) and tris(dibenzylideneacetone)dipalladium(0) (123 mg, 0.14 mmol) were successively added to a toluene solution (10 ml) of 4-chloro-6-quinazolinyl acetate (300 mg, 1.35 mmol) and 5-methoxy[1,3]thiazolo[5,4-b]pyridine-2-amine (244 mg, 1.35 mmol), and stirred under a nitrogen atmosphere at 120° C. for 2 hours. The reaction solution was cooled to room temperature, filtered, and washed with chloroform and methanol. The obtained filtrate was concentrated under reduced pressure to obtain 4-[(5-methoxy[1,3]thiazolo[5,4-b]pyridin-2-yl)amino]-6-quinazolinyl acetate (196 mg, yield: 40%) as a yellow solid.

2) 28% ammonia water (1 ml) was added to a methanol solution (5 ml) of the ester product (196 mg, 0.53 mmol) obtained in the above reaction, and stirred at 50° C. for 3 hours. Toluene was added to the reaction solution, concentrated under reduced pressure, suspended in a small amount of methanol, collected by filtration, and dried to obtain 4-[(5-methoxy[1,3]thiazolo[5,4-b]pyridin-2-yl)amino]quinazolin-6-ol (174 mg, yield: 100%) as a yellow solid.

Example 47 extracted with chloroform, the organic layer was washed with water and saturated saline water, dried over anhydrous sodium sulfate, and concentrated under reduced pressure. The obtained residue was purified by silica gel column chromatography (chloroform:methanol=90:10) to obtain 6-{[5-(2,2-diethoxyethoxy)pyridin-2-yl]oxy}-N-(3-methyl-1,2,4-thiadiazol-5-yl)quinazoline-4-amine (220 mg, yield: 40%) as a pale yellow solid.

2) Trifluoroacetic acid (1 ml) and water (0.1 ml) were added to a chloroform solution (1 ml) of the acetal product (30 mg, 0.064 mmol) obtained in the above reaction, and stirred at room temperature for 1 hour. The reaction solution was diluted with chloroform, then washed with aqueous saturated sodium hydrogencarbonate solution and saturated saline water, dried over anhydrous sodium sulfate, and concentrated under reduced pressure to obtain a crude product of 6-{[5-(formylmethoxy)pyridin-2-yl]oxy}-N-(3-methyl-1,2,4-thiadiazol-5-yl)quinazoline-4-amine.

3) 2 M dimethylamine/tetrahydrofuran solution (0.013 ml, 0.19 mmol) was added to a tetrahydrofuran (2 ml) solution of the crude aldehyde product obtained in the above reaction, stirred for 30 minutes, and then sodium triacetoxyborohydride (41 mg, 0.19 mmol) was added, and further stirred for 10 minutes. Aqueous saturated ammonium chloride solution was added to the reaction solution, and extracted with chloroform. The organic layer was washed with water and saturated saline water, dried over anhydrous sodium sulfate, and concentrated under reduced pressure. The obtained residue was purified by amine-type thin-layer silica gel column chromatography (chloroform:methanol=95:5 and hexane:ethyl acetate=2:1) to obtain the entitled compound (22 mg, yield: 81%) as a pale yellow solid.

The analytical data of the entitled compound are shown below.

$^1$HNMR (DMSO-$d_6$) δ: 2.28 (s, 6H), 2.48 (s, 3H), 2.73 (t, 2H, J=5.5 Hz), 4.14 (t, 2H, J=5.5 Hz), 7.17 (d, 1H, J=8.8 Hz), 7.60 (dd, 1H, J=3.4, 8.8 Hz), 7.71 (dd, 1H, J=3.4, 8.8 Hz), 7.92-7.95 (m, 2H), 8.34 (s, 1H), 8.87 (s, 1H)

ESI-MS (m/e): 424 [M+H]$^+$

Example 48

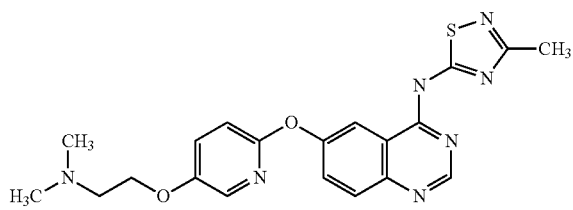

Preparation of 6-({5-[2-(dimethylamino)ethoxy]pyridin-2-yl}oxy)-N-(3-methyl-1,2,4-thiadiazol-5-yl)quinazoline-4-amine 1) 5-(2,2-diethoxyethoxy)-2-fluoropyridine (530 mg, 2.3 mmol) and potassium tert-butoxide (260 mg, 2.3 mmol) were added to an N,N-dimethylacetamide suspension (0.5 ml) of 4-[(3-methyl-1,2,4-thiadiazol-5-yl)amino]quinazolin-6-ol (300 mg, 1.2 mmol), and reacted at 200° C. for 30 minutes, using microwaves. The reaction solution was cooled to room temperature, aqueous saturated ammonium chloride solution was added, filtered, and washed with a mixed solution of chloroform/methanol (9:1). The obtained filtrate was

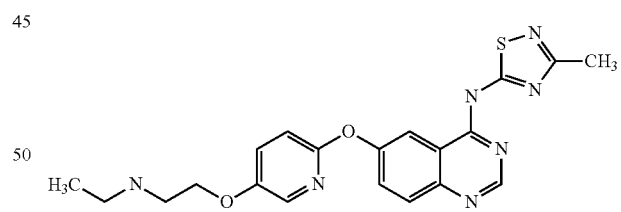

Preparation of 6-({5-[2-(ethylamino)ethoxy]pyridin-2-yl}oxy)-N-(3-methyl-1,2,4-thiadiazol-5-yl)quinazoline-4-amine Using 6-{[5-(2,2-diethoxyethoxy)pyridin-2-yl]oxy}-N-(3-methyl-1,2,4-thiadiazol-5-yl)quinazoline-4-amine obtained in Example 47 and 2 M ethylamine/tetrahydrofuran solution, and in the same manner as in Example 47 or according to a method similar to it or according to a combination thereof with an ordinary method, the entitled compound (24 mg) was obtained as a yellow solid.

The analytical data of the entitled compound are shown below.

$^1$HNMR (DMSO-d$_6$) δ: 1.13 (t, 3H, J=7.3 Hz), 2.34 (s, 3H), 2.87 (t, 2H, J=5.5 Hz), 3.17-3.19 (m, 2H), 4.22 (t, 2H, J=5.1 Hz), 7.17 (d, 1H, J=8.8 Hz), 7.61 (dd, 1H, J=2.9, 8.8 Hz), 7.74 (s, 1H), 8.00 (d, 1H, J=2.9 Hz), 8.66 (s, 1H)

ESI-MS (m/e): 424 [M+H]$^+$

Example 49

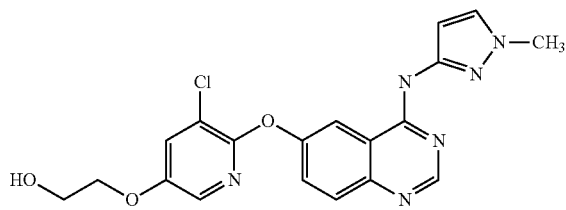

Preparation of 2-{[5-chloro-6-({4-[(1-methyl-1H-pyrazol-3-yl)amino]quinazolin-6-yl}oxy)pyridin-3-yl]oxy}ethanol With cooling with ice, sodium borohydride (9 mg, 0.25 mmol) was added to a tetrahydrofuran (3 ml)/water (0.3 ml) mixed solution containing {[5-chloro-6-({4-[(1-methyl-1H-pyrazol-3-yl)amino]quinazolin-6-yl}oxy)pyridin-3-yl]oxy}acetaldehyde obtained in Example 1, and the reaction solution was stirred for 15 minutes. Saturated saline water was added to the reaction solution, extracted with chloroform/methanol (9:1), the organic layer was dried over anhydrous sodium sulfate, and concentrated under reduced pressure. The obtained residue was purified by silica gel column chromatography (Biotage, chloroform:methanol=100:4 to 100:5) and reversed-phase liquid chromatography (YMC CombiPrep Pro C18 AS-360-CC), and the obtained solid was recrystallized from ethyl acetate to obtain the entitled compound (19 mg) as a white solid.

The analytical data of the entitled compound are shown below.

$^1$H-NMR (DMSO-d$_6$) δ: 3.72 (2H, q, J=5.0 Hz), 3.80 (3H, s), 4.09 (2H, t, J=4.9 Hz), 4.94 (1H, t, J=5.4 Hz), 6.79 (1H, d, J=2.4 Hz), 7.64 (2H, dd, J=2.7, 9.0 Hz), 7.81 (1H, d, J=8.8 Hz), 7.88 (1H, d, J=2.4 Hz), 7.91 (1H, d, J=2.9 Hz), 8.33 (1H, d, J=2.4 Hz), 8.57 (1H, s), 10.30 (1H, s).

ESI-MS (m/e): 413 [M+H]$^+$

Example 50

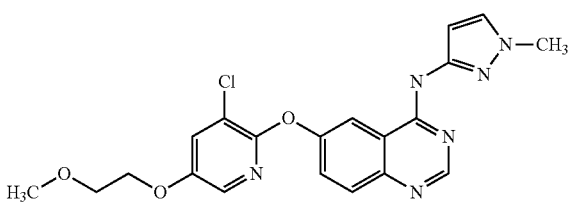

Preparation of 6-{[3-chloro-5-(2-methoxyethoxy)pyridin-2-yl]oxy}-N-(1-methyl-1H-pyrazol-3-yl)quinazoline-4-amine 2,3-Dichloro-5-(2-methoxyethoxy)pyridine (127 mg, 0.57 mmol) and potassium tert-butoxide (70 mg, 0.62 mmol) were added to an N,N-dimethylacetamide solution (2 ml) of 4-[(1-methyl-1H-pyrazol-3-yl)amino]quinazolin-6-ol (60 mg, 0.25 mmol), and stirred overnight at 180° C. under a nitrogen atmosphere in a sealed tube. The reaction solution was cooled with ice, then sodium chloride water and chloroform were added, the organic layer was washed with water, dried over anhydrous sodium sulfate, and concentrated under reduced pressure. The obtained residue was purified by reversed-phase liquid chromatography (YMC CombiPrep Pro C18 AS-360-CC) to obtain the entitled compound (30 mg, yield: 28%) as a pale orange amorphous solid.

The analytical data of the entitled compound are shown below.

$^1$H-NMR (DMSO-d$_6$) δ: 2.50-2.51 (2H, m), 3.31 (3H, s), 3.65-3.68 (2H, m), 3.81 (3H, s), 4.19-4.22 (2H, m), 6.80 (1H, brs), 7.63-7.66 (2H, m), 7.81 (1H, d, J=9.3 Hz), 7.90 (1H, d, J=2.9 Hz), 7.92 (1H, d, J=2.9 Hz), 8.33 (1H, s), 8.57 (1H, s), 10.31 (1H, s).

ESI-MS (m/e): 427 [M+H]$^+$

Preparation of 2,3-dichloro-5-(2-methoxyethoxy)pyridine

2-Bromoethyl methyl ether (0.44 ml, 4.57 mmol) and cesium carbonate (2.48 g, 7.62 mmol) were added to an N,N-dimethylacetamide solution (5 ml) of 5,6-dichloropyridin-3-ol (500 mg, 3.05 mmol), and stirred under a nitrogen atmosphere at 80° C. for 5 hours. The reaction solution was cooled with ice, then ammonium chloride water and ethyl acetate were added, the organic layer was washed with water, dried over anhydrous sodium sulfate, and concentrated under reduced pressure. The obtained residue was purified by silica gel column chromatography (Biotage, hexane:ethyl acetate=9:1) to obtain 2,3-dichloro-5-(2-methoxyethoxy)pyridine (573 mg, yield: 85%) as an orange oil.

Example 51

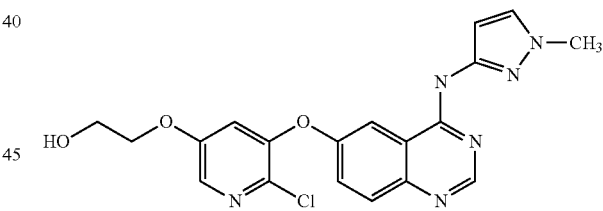

Preparation of 2-{[6-chloro-5-({4-[(1-methyl-1H-pyrazol-3-yl)amino]quinazolin-6-yl}oxy)pyridin-3-yl]oxy}ethanol Using {[6-chloro-5-({4-[(1-methyl-1H-pyrazol-3-yl)amino]quinazolin-6-yl}oxy)pyridin-3-yl]oxy}acetaldehyde obtained in Example 2, and in the same manner as in Example 49r according to a method similar to it or according to a combination thereof with an ordinary method, the entitled compound (4 mg) was obtained as a yellow solid.

The analytical data of the entitled compound are shown below.

$^1$H-NMR (DMSO-d$_6$) δ: 3.69 (2H, q, J=5.4 Hz), 3.79 (3H, s), 4.06 (2H, t, J=4.9 Hz), 4.90 (1H, t, J=5.4 Hz), 6.77 (1H, d, J=2.4 Hz), 7.38 (1H, d, J=2.9 Hz), 7.64-7.69 (2H, m), 7.84 (1H, d, J=8.8 Hz), 8.09 (1H, d, J=2.4 Hz), 8.12 (1H, d, J=2.9 Hz), 8.56 (1H, s), 10.33 (1H, s)

ESI-MS (m/e): 413 [M+H]$^+$.

Example 52

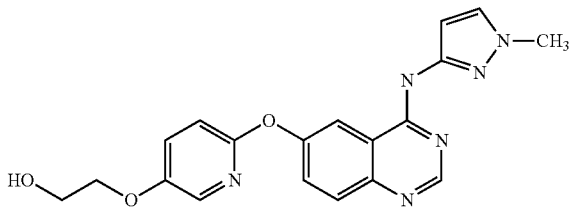 [SMILES: Cn1ccc(Nc2ncnc3ccc(Oc4ccc(OCCO)cn4)cc23)n1]

Preparation of 2-{[6-({4-[(1-methyl-1H-pyrazol-3-yl)amino]quinazolin-6-yl}oxy)pyridin-3-yl]oxy}ethanol Using {[6-({4-[(1-methyl-1H-pyrazol-3-yl)amino] quinazolin-6-yl}oxy)pyridin-3-yl]oxy}acetaldehyde obtained in Example 5, and in the same manner as in Example 49r according to a method similar to it or according to a combination thereof with an ordinary method, the entitled compound (36 mg) was obtained as a yellow solid.

The analytical data of the entitled compound are shown below.

$^1$H-NMR (DMSO-$d_6$) δ: 3.72 (2H, q, J=5.2 Hz), 3.80 (3H, s), 4.05 (2H, t, J=4.9 Hz), 4.92 (1H, t, J=5.6 Hz), 6.80 (1H, d, J=2.4 Hz), 7.12 (1H, d, J=8.8 Hz), 7.56-7.60 (2H, m), 7.65 (1H, d, J=2.4 Hz), 7.79 (1H, d, J=8.8 Hz), 7.92 (1H, d, J=2.9 Hz), 8.35 (1H, d, J=2.4 Hz), 8.56 (1H, s), 10.31 (1H, s).

ESI-MS (m/e): 379 [M+H]$^+$

Example 53

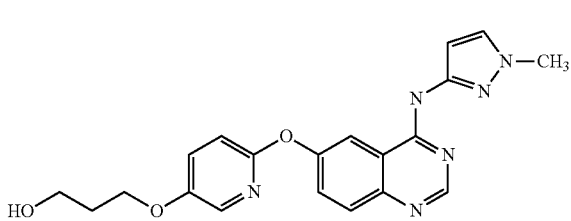 [SMILES: Cn1ccc(Nc2ncnc3ccc(Oc4ccc(OCCCO)cn4)cc23)n1]

Preparation of 3-{[6-({4-[(1-methyl-1H-pyrazol-3-yl)amino]quinazolin-6-yl}oxy)pyridin-3-yl]oxy}propan-1-ol As an intermediate (131 mg) in Example 4, the entitled compound was obtained as a pale yellow amorphous solid.

The analytical data of the entitled compound are shown below.

$^1$H-NMR (DMSO-$d_6$) δ: 1.84-1.90 (2H, m), 3.56 (2H, q, J=5.9 Hz), 3.80 (3H, s), 4.09 (2H, t, J=6.3 Hz), 4.57 (1H, t, J=5.1 Hz), 6.79 (1H, d, J=2.4 Hz), 7.12 (1H, d, J=8.8 Hz), 7.55-7.60 (2H, m), 7.65 (1H, d, J=2.4 Hz), 7.79 (1H, d, J=8.8 Hz), 7.90 (1H, d, J=3.4 Hz), 8.34 (1H, d, J=2.4 Hz), 8.56 (1H, s), 10.30 (1H, s).

ESI-MS (m/e): 393 [M+H]$^+$

Example 54

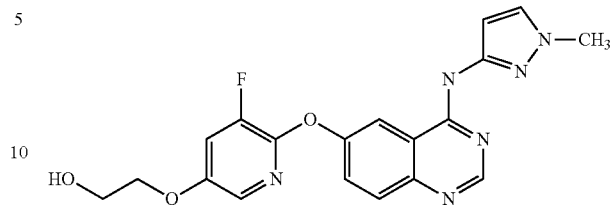

Preparation of 2-{[5-fluoro-6-({4-[(1-methyl-1H-pyrazol-3-yl)amino]quinazolin-6-yl}oxy)pyridin-3-yl]oxy}ethanol Using {5-fluoro-6-({4-[(1-methyl-1H-pyrazol-3-yl) amino]quinazolin-6-yl}oxy)pyridin-3-yl]oxy}acetaldehyde obtained in Example 19, and in the same manner as in Example 49 or according to a method similar to it or according to a combination thereof with an ordinary method, the entitled compound (8 mg) was obtained as a yellow amorphous solid.

The analytical data of the entitled compound are shown below.

$^1$H-NMR (DMSO-$d_6$) δ: 3.73 (2H, q, J=5.0 Hz), 3.80 (3H, s), 4.10 (2H, t, J=4.9 Hz), 4.95 (1H, t, J=5.6 Hz), 6.79 (1H, d, J=2.0 Hz), 7.64-7.82 (5H, m), 8.31 (1H, d, J=2.4 Hz), 8.56 (1H, s), 10.30 (1H, s).

ESI-MS (m/e): 397 [M+H]$^+$

Example 55

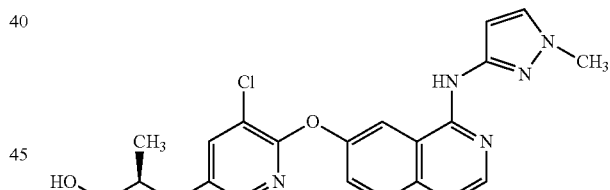

Preparation of (2R)-2-{[5-chloro-6-({4-[(1-methyl-1H-pyrazol-3-yl)amino]quinazolin-6-yl}oxy)pyridin-3-yl]oxy}propan-1-ol 1) (1S)-2-{[tert-butyl(dimethyl)silyl]oxy}-1-methylethyl methanesulfonate (79 mg, 0.29 mmol) and potassium tert-butoxide (55 mg, 0.49 mmol) were added to a dimethyl sulfoxide solution (3 ml) of 5-chloro-6-({4-[(1-methyl-1H-pyrazol-3-yl)amino]quinazolin-6-yl}oxy)pyridin-3-ol (90 mg, 0.24 mmol) obtained in Example 22, then stirred for 24 hours at 100° C. The reaction solution was cooled to room temperature, water was added, and extracted with ethyl acetate. The organic layer was washed with saturated saline water, dried over anhydrous sodium sulfate, and concentrated under reduced pressure. The obtained residue was purified by silica gel column chromatography (hexane:ethyl acetate=1:2 to 0:1) to obtain 6-{[5-((1R)-2-{[tert-butyl(dimethyl)silyl]

oxy}-1-methylethoxy)-3-chloropyridin-2-yl]oxy}-N-(1-methyl-1H-pyrazol-3-yl)quinazoline-4-amine (43 mg, yield: 33%) as a white solid.

2) 4 N hydrochloric acid/1,4-dioxane solution (3 ml, 12 mmol) was added to 1,4-dioxane solution (3 ml) of the silyl product (43 mg, 0.079 mmol) obtained in the above reaction, and stirred at room temperature for 2 hours. The reaction solution was concentrated under reduced pressure, and extracted with a mixed solution of chloroform/methanol (4:1). The organic layer was washed with aqueous saturated sodium hydrogencarbonate solution and saturated saline water, dried over anhydrous sodium sulfate, and concentrated under reduced pressure. The obtained residue was purified by silica gel column chromatography (chloroform:methanol=92:8) to obtain the entitled compound (30 mg, yield: 88%) as a white solid.

The analytical data of the entitled compound are shown below.

$^1$H-NMR (DMSO-D$_6$) δ: 1.21 (3H, d, J=6.3 Hz), 3.49-3.53 (2H, m), 3.79 (3H, s), 4.49-4.50 (1H, m), 4.91 (1H, t, J=5.9 Hz), 6.78 (1H, d, J=2.2 Hz), 7.61-7.64 (2H, m), 7.79 (1H, d, J=9.3 Hz), 7.86-7.88 (2H, m), 8.34 (1H, d, J=2.2 Hz), 8.56 (1H, s), 10.29 (1H, s).

ESI-MS (m/e): 427 [M+H]$^+$

Example 56

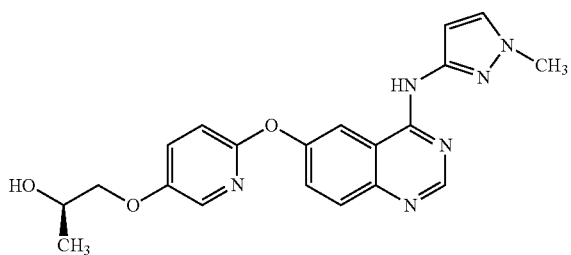 [SMILES: C[C@@H](O)COc1ccc(Oc2ccc3ncnc(Nc4ccn(C)n4)c3c2)nc1]

Preparation of (2R)-1-{[6-({4-[(1-methyl-1H-pyrazol-3-yl)amino]quinazolin-6-yl}oxy)pyridin-3-yl]oxy}propan-2-ol According to Example 26-1) and 26-2), the entitled compound (42 mg) was obtained as a pale yellow amorphous solid.

The analytical data of the entitled compound are shown below.

$^1$HNMR (DMSO-d$_6$) δ: 1.09 (d, 3H, J=4.0 Hz), 3.74 (s, 3H), 3.77-3.83 (m, 2H), 3.83-3.91 (m, 1H), 4.86 (d, 1H, J=4.0 Hz), 6.73 (d, 1H, J=4.0 Hz), 7.05 (d, 1H, J=12.0 Hz), 7.50-7.54 (m, 2H), 7.59 (d, 1H, J=4.0 Hz), 7.73 (d, 1H, J=12 Hz), 7.85 (d, 1H, J=4.0 Hz), 8.28 (d, 1H, J=4.0 Hz), 8.50 (s, 1H), 10.24 (s, 1H).

ESI-MS (m/e): 393 [M+H]$^+$

Example 57

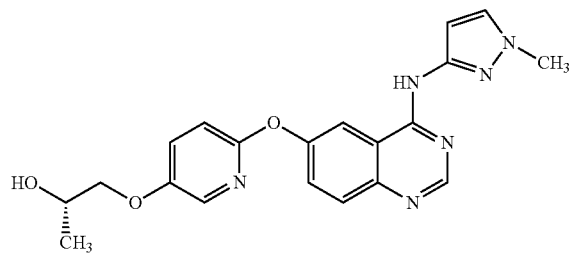 [SMILES: C[C@H](O)COc1ccc(Oc2ccc3ncnc(Nc4ccn(C)n4)c3c2)nc1]

Preparation of (2S)-1-{[6-({4-[(1-methyl-1H-pyrazol-3-yl)amino]quinazolin-6-yl}oxy)pyridin-3-yl]oxy}propan-2-ol Using 6-({4-[(1-methyl-1H-pyrazol-3-yl)amino]quinazolin-6-yl}oxy)pyridin-3-ol obtained in Example 6-3) and (2R)-2-(tetrahydro-2H-pyran-2-yloxy)propyl methanesulfonate, and in the same manner as in Example 26-1) and 26-2), the entitled compound (42 mg) was obtained as a pale yellow amorphous solid.

The analytical data of the entitled compound are shown below.

$^1$HNMR (DMSO-d$_6$) δ: 1.09 (d, 3H, J=4.0 Hz), 3.74 (s, 3H), 3.77-3.83 (m, 2H), 3.83-3.91 (m, 1H), 4.86 (d, 1H, J=4.0 Hz), 6.73 (d, 1H, J=4.0 Hz), 7.05 (d, 1H, J=12.0 Hz), 7.50-7.54 (m, 2H), 7.59 (d, 1H, J=4.0 Hz), 7.73 (d, 1H, J=12 Hz), 7.85 (d, 1H, J=4.0 Hz), 8.28 (d, 1H, J=4.0 Hz), 8.50 (s, 1H), 10.24 (s, 1H).

ESI-MS (m/e): 393 [M+H]$^+$

Example 58

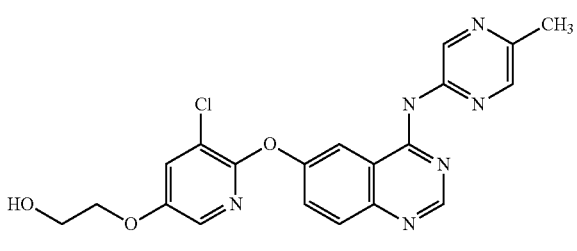 [SMILES: Cc1cnc(Nc2ncnc3ccc(Oc4ncc(OCCO)cc4Cl)cc23)cn1]

Preparation of 2-{[5-chloro-6-({4-[(5-methylpyrazin-2-yl)amino]quinazolin-6-yl}oxy)pyridin-3-yl]oxy}ethanol Using {[5-chloro-6-({4-[(5-methylpyrazin-2-yl)amino]quinazolin-6-yl}oxy)pyridin-3-yl]oxy}acetaldehyde obtained in Example 32, and in the same manner as in Example 49 or according to a method similar to it or according to a combination thereof with an ordinary method, the entitled compound (10 mg) was obtained as a pale yellow solid.

The analytical data of the entitled compound are shown below.

$^1$HNMR (DMSO-d$_6$) δ: 2.48-2.50 (m, 3H), 3.70 (q, 2H, J=4.9 Hz), 4.08 (t, 2H, J=4.9 Hz), 4.93 (t, 1H, J=4.9 Hz), 7.72

(dd, 1H, J=2.4, 8.8 Hz), 7.87-7.90 (m, 3H), 8.35 (s, 1H), 8.41 (s, 1H), 8.68 (s, 1H), 9.43 (d, 1H, J=1.5 Hz), 10.45 (s, 1H)
ESI-MS (m/e): 425 [M+H]⁺

Example 59

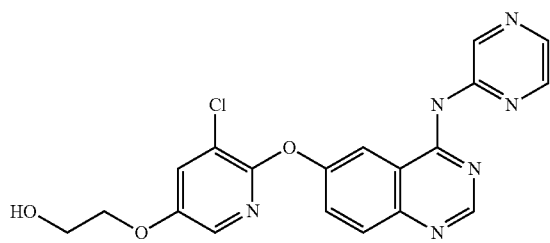 [SMILES: OCCOc1cnc(Oc2ccc3ncnc(Nc4cnccn4)c3c2)c(Cl)c1]

Preparation of 2-{[5-chloro-6-{[4-(pyrazin-2-ylamino)quinazolin-6-yl]oxy}pyridin-3-yl)oxy]ethanol Using [(5-chloro-6-{[4-(pyrazin-2-ylamino)quinazolin-6-yl]oxy}pyridin-3-yl)oxy]acetaldehyde obtained in Example 44 and in the same manner as in Example 49 or according to a method similar to it or according to a combination thereof with an ordinary method, the entitled compound (5 mg) was obtained as a yellow solid.
The analytical data of the entitled compound are shown below.
¹HNMR (DMSO-d₆) δ: 3.70 (q, 2H, J=5.0 Hz), 4.08 (t, 2H, J=5.0 Hz), 4.93 (t, 1H, J=5.0 Hz), 7.71-7.76 (m, 1H), 7.90-7.92 (m, 3H), 8.35 (s, 1H), 8.40-8.47 (m, 2H), 8.72 (s, 1H), 9.58-9.60 (m, 1H), 10.54-10.59 (m, 1H)
ESI-MS (m/e): 411 [M+H]⁺

Example 60

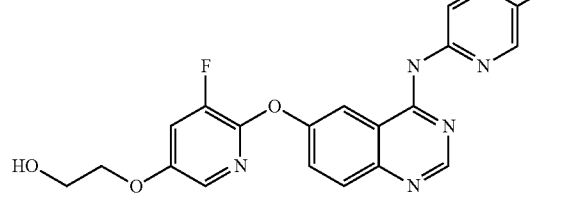

Preparation of 2-{[5-fluoro-6-({4-[(5-methylpyrazin-2-yl)amino]quinazolin-6-yl}oxy)pyridin-3-yl}oxy}ethanol Using {[5-fluoro-6-({4-[(5-methylpyrazin-2-yl)amino]quinazolin-6-yl}oxy)pyridin-3-yl]oxy}acetaldehyde obtained in Example 33, and in the same manner as in Example 49 or according to a method similar to it or according to a combination thereof with an ordinary method, the entitled compound (10 mg) was obtained as a white solid.
The analytical data of the entitled compound are shown below.
¹HNMR (DMSO-d₆) δ: 2.48-2.50 (m, 3H), 3.72 (q, 2H, J=5.0 Hz), 4.08 (t, 2H, J=4.6 Hz), 4.93 (t, 1H, J=5.4 Hz), 7.81-7.71 (m, 3H), 7.89 (d, 1H, J=8.8 Hz), 8.34 (s, 1H), 8.39 (d, 1H, J=2.4 Hz), 8.67 (s, 1H), 9.43 (d, 1H, J=1.5 Hz), 10.45 (s, 1H)
ESI-MS (m/e): 409 [M+H]⁺

Example 61

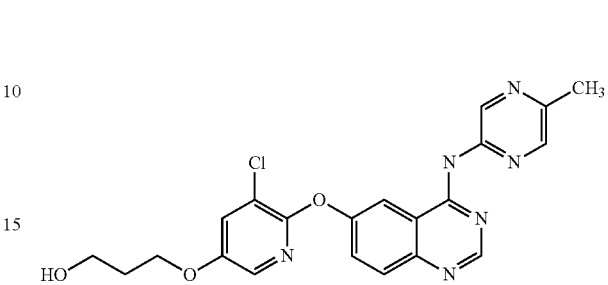

Preparation of 3-{[5-chloro-6-({4-[(5-methylpyrazin-2-yl)amino]quinazolin-6-yl}oxy)pyridin-3-yl]oxy}propan-1-ol In the same manner as in Example 43-1) and 43-2), the entitled compound (830 mg) was obtained as a pale yellow solid.
The analytical data of the entitled compound are shown below.
¹H-NMR (DMSO-d₆) δ: 1.84-1.90 (2H, m), 2.49-2.51 (3H, m), 3.55 (2H, q, J=5.9 Hz), 4.13 (2H, t, J=6.3 Hz), 4.58 (1H, t, J=5.1 Hz), 7.73 (1H, dd, J=2.4, 9.3 Hz), 7.87-7.91 (3H, m), 8.36 (1H, brs), 8.41 (1H, d, J=2.4 Hz), 8.69 (1H, s), 9.44 (1H, d, J=1.5 Hz), 10.45 (1H, s).
ESI-MS (m/e): 439 [M+H]⁺

Example 62

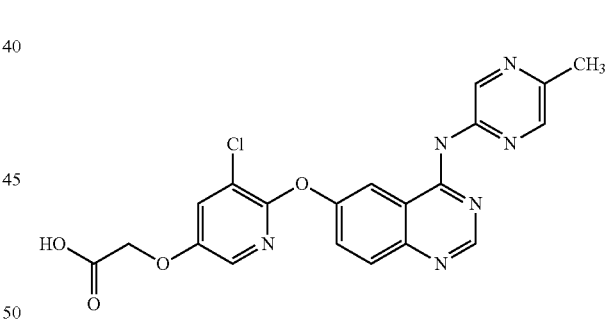

Preparation of {[5-chloro-6-({4-[(5-methylpyrazin-2-yl)amino]quinazolin-6-yl}oxy)pyridin-3-yl]oxy}acetic acid Sodium chlorite (30 mg, 0.33 mmol) was added to a water (0.3 ml)/2-methyl-2-propanol (1.2 ml) mixed solution of {[5-chloro-6-({4-[(5-methylpyrazin-2-yl)amino]quinazolin-6-yl}oxy)pyridin-3-yl]oxy}acetaldehyde (50 mg, 0.11 mmol) obtained in Example 32, 2-methyl-2-butene (0.051 ml, 0.48 mmol) and sodium dihydrogenphosphate (13 mg, 0.11 mmol), and the reaction solution was stirred at room temperature for 1 hour. Aqueous 1 N hydrochloric acid solution was added to the reaction solution, and extracted with chloroform/methanol (9:1). The organic layer was dried over anhydrous sodium sulfate, and concentrated under reduced pressure.

The obtained residue was recrystallized from ethyl acetate to obtain the entitled compound (37 mg, yield: 77%) as a yellow solid.

The analytical data of the entitled compound are shown below.

$^1$H-NMR (DMSO-$d_6$) δ: 2.49-2.51 (3H, m), 4.81 (2H, s), 7.74 (1H, dd, J=2.4, 8.8 Hz), 7.89-7.91 (3H, m), 8.36 (1H, brs), 8.47 (1H, d, J=2.4 Hz), 8.70 (1H, s), 9.45 (1H, brs), 10.48 (1H, s).

ESI-MS (m/e): 439 [M+H]$^+$

Example 63

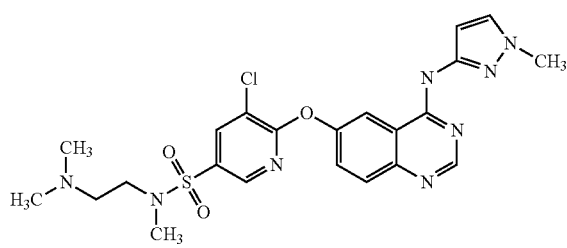

Preparation of 5-chloro-N-[2-(dimethylamino)ethyl]-N-methyl-6-({4-[(1-methyl-1H-pyrazol-3-yl)amino]quinazolin-6-yl}oxy)pyridine-3-sulfonamide 5,6-Dichloro-N-[2-(dimethylamino)ethyl]-N-methylpyridine-3-sulfonamide (104 mg, 0.33 mmol) and potassium tert-butoxide (58 mg, 0.52 mmol) were added to an N,N-dimethylacetamide solution (1 ml) of 4-[(1-methyl-1H-pyrazol-3-yl)amino]quinazolin-6-ol (50 mg, 0.21 mmol), and stirred under a nitrogen atmosphere at 100° C. for 2.5 hours. The reaction solution was cooled with ice, saline water was added, and extracted with chloroform. The organic layer was washed with water, dried over anhydrous sodium sulfate, and concentrated under reduced pressure. The obtained residue was purified by amine-type silica gel column chromatography (Biotage NH, hexane:ethyl acetate:chloroform=2:5:1 to 2:5:2) to obtain the entitled compound (65 mg, yield: 61%) as a pale orange amorphous solid.

The analytical data of the entitled compound are shown below.

$^1$H-NMR (DMSO-$d_6$) δ: 2.15 (6H, s), 2.58 (2H, t, J=5.6 Hz), 3.79 (3H, s), 4.11 (2H, t, J=5.6 Hz), 6.77 (1H, d, J=2.0 Hz), 7.41 (1H, d, J=2.4 Hz), 7.64-7.69 (2H, m), 7.84 (1H, d, J=8.8 Hz), 8.08 (1H, d, J=2.9 Hz), 8.13 (1H, d, J=2.4 Hz), 8.56 (1H, s), 10.33 (1H, s).

ESI-MS (m/e): 517 [M+H]$^+$

Preparation of 5,6-dichloro-N-[2-(dimethylamino)ethyl]-N-methylpyridine-3-sulfonamide 1) With cooling with ice, an aqueous solution (2.5 ml) of sodium nitrite (1.1 g, 16.0 mmol) was added to a hydrochloric acid solution (15 ml) of 5,6-dichloropyridine-3-amine (2.0 g, 12.3 mmol), stirred for 30 minutes, and the reaction solution was filtered. The filtrate was added to a mixed hydrochloric acid (35 ml)/water (8 ml) solution of sodium sulfite (3.87 g, 30.7 mmol) and copper sulfate (0.29 g, 1.84 mmol) along with an aqueous solution (8 ml) of sodium sulfite (3.87 g, 30.7 mmol) thereto, with cooling with ice, and stirred for 30 minutes. The reaction solution was extracted with chloroform, the organic layer was washed with saturated saline water, dried over anhydrous sodium sulfate, and concentrated under reduced pressure to obtain 5,6-dichloropyridine-3-sulfonyl chloride (2.41 g, yield: 80%) as a brown oil.

2) With cooling with ice, triethylamine (0.57 ml, 4.06 mmol) and N,N,N'-trimethylethane-1,2-diamine (0.30 ml, 2.23 mmol) were added to a tetrahydrofuran solution (5 ml) of 5,6-dichloropyridine-3-sulfonyl chloride (500 mg, 2.03 mmol) obtained in the above reaction, and stirred for 5 minutes. Saturated saline water was added to the reaction solution, extracted with chloroform, dried over anhydrous sodium sulfate, and concentrated under reduced pressure. The obtained residue was purified by amine-type silica gel column chromatography (Biotage NH, hexane:ethyl acetate=5:1 to 3:1) to obtain 5,6-dichloro-N-[2-(dimethylamino)ethyl]-N-methylpyridine-3-sulfonamide (460 mg, yield: 73%) as a red solid.

Example 64

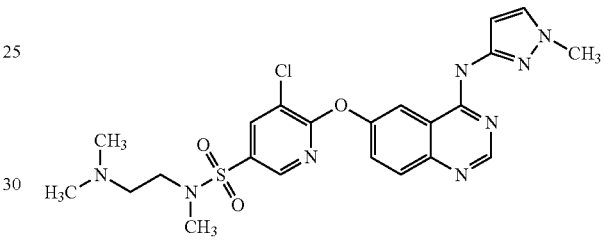

Preparation of 5-chloro-N-[3-(dimethylamino)propyl]-N-methyl-6-({4-[(1-methyl-1H-pyrazol-3-yl)amino]quinazolin-6-yl}oxy)pyridine-3-sulfonamide 5,6-Dichloro-N-[3-(dimethylamino)propyl]-N-methylpyridine-3-sulfonamide (122 mg, 0.37 mmol) and potassium tert-butoxide (58 mg, 0.52 mmol) were added to an N,N-dimethylacetamide solution (1 ml) of 4-[(1-methyl-1H-pyrazol-3-yl)amino]quinazolin-6-ol (50 mg, 0.21 mmol), and stirred under a nitrogen atmosphere at 100° C. for 2.5 hours. The reaction solution was cooled with ice, saline water was added, and extracted with chloroform/methanol (9:1). The organic layer was washed with water, dried over anhydrous sodium sulfate, and concentrated under reduced pressure. The obtained residue was purified by amine-type silica gel column chromatography (Biotage NH, hexane:ethyl acetate:chloroform to chloroform:methanol=2:4:1 to 100:2) to obtain the entitled compound (75 mg, yield: 68%) as a pale orange amorphous solid.

The analytical data of the entitled compound are shown below.

$^1$H-NMR (DMSO-$d_6$) δ: 1.58-1.65 (2H, m), 2.10 (6H, s), 2.19 (2H, t, J=6.8 Hz), 2.75 (3H, s), 3.05 (2H, t, J=7.1 Hz), 3.81 (3H, s), 6.82 (1H, d, J=2.0 Hz), 7.66 (1H, d, J=2.0 Hz), 7.79 (1H, dd, J=2.4, 8.8 Hz), 7.87 (1H, d, J=8.8 Hz), 8.48 (2H, brs), 8.59 (1H, d, J=2.4 Hz), 8.62 (1H, s), 10.34 (1H, s).

ESI-MS (m/e): 531 [M+H]$^+$

Preparation of 5,6-dichloro-N-[3-(dimethylamino)propyl]-N-methylpyridine-3-sulfonamide With cooling with ice, triethylamine (0.57 ml, 4.06 mmol) and N,N,N'-trimethylpropane-1,3-diamine (0.34 ml, 2.23 mmol) were added to a tetrahydrofuran solution (5 ml) of 5,6-dichloropyridin-3-sulfonyl chloride (500 mg, 2.03 mmol), and stirred for 5 minutes. Saturated saline water was added to the reaction solution, extracted with chloroform, and the organic layer was dried over anhydrous sodium sulfate, concentrated under reduced pressure. The obtained residue was purified by amine-type silica gel column chromatography (Biotage NH, hexane:ethyl acetate=6:1 to 4:1) to obtain 5,6-dichloro-N-[3-(dimethylamino)propyl]-N-methylpyridine-3-sulfonamide (454 mg, yield: 69%) as a red solid.

Example 65

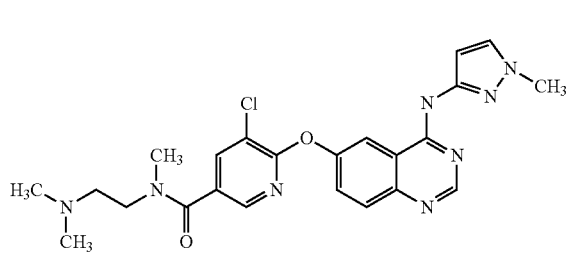

Preparation of 5-chloro-N-[2-(dimethylamino)ethyl]-N-methyl-6-({4-[(1-methyl-1H-pyrazol-3-yl)amino]quinazolin-6-yl}oxy)nicotinamide 5,6-Dichloro-N-[2-(dimethylamino)ethyl]-N-methylnicotinamide (126 mg, 0.46 mmol) and potassium tert-butoxide (58 mg, 0.52 mmol) were added to an N,N-dimethylacetamide solution (1 ml) of 4-[(1-methyl-1H-pyrazol-3-yl)amino]quinazolin-6-ol (50 mg, 0.21 mmol), and stirred overnight under a nitrogen atmosphere at 130° C. The reaction solution was cooled with ice, saline water was added, and extracted with chloroform. The organic layer was washed with water, then dried over anhydrous sodium sulfate, and concentrated under reduced pressure. The obtained residue was purified by amine-type silica gel column chromatography (Biotage NH, hexane:ethyl acetate to chloroform:methanol=1:4 to 100:2) to obtain the entitled compound (25 mg, yield: 25%) as a pale yellow solid.

The analytical data of the entitled compound are shown below.

$^1$H-NMR (DMSO-$d_6$) δ: 2.02 (3H, s), 2.19 (3H, s), 2.49-2.51 (2H, m), 2.98 (3H, s), 3.31-3.52 (2H, m), 3.80 (3H, s), 6.81 (1H, d, J=2.0 Hz), 7.66 (1H, d, J=2.4 Hz), 7.74 (1H, dd, J=2.4, 8.8 Hz), 7.84 (1H, d, J=8.8 Hz), 8.15 (1H, d, J=2.0 Hz), 8.20 (1H, brs), 8.54 (1H, d, J=2.4 Hz), 8.61 (1H, d, J=5.9 Hz), 10.34 (1H, s).

ESI-MS (m/e): 481 [M+H]$^+$

Preparation of 5,6-dichloro-N-[2-(dimethylamino)ethyl]-N-methylnicotinamide

N,N-dimethylformamide (0.05 ml, 0.65 mmol) was added to a thionyl chloride solution (10 ml) of 5-chloro-6-hydroxynicotinic acid (1.0 g, 5.76 mmol), and stirred under a nitrogen atmosphere at 90° C. for 1 hour. The reaction solution was concentrated under reduced pressure, and with cooling with ice, N,N,N'-trimethylethane-1,2-diamine (2.32 ml, 17.3 mmol) was added to an N,N-dimethylformamide solution (10 ml) of the obtained residue, and stirred at room temperature for 3 minutes. Saturated saline water was added to the reaction solution, extracted with chloroform, dried over anhydrous sodium sulfate, and concentrated under reduced pressure. The obtained residue was purified by amine-type silica gel column chromatography (Biotage NH, hexane:ethyl acetate=4:1 go 1:1) to obtain 5,6-dichloro-N-[2-(dimethylamino)ethyl]-N-methylnicotinamide (1.59 g, yield: 100%) as a colorless oil.

Example 66

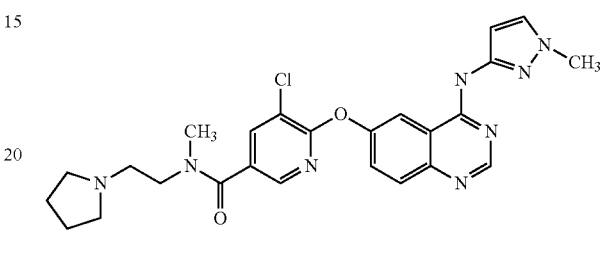

Preparation of 5-chloro-N-methyl-6-({4-[(1-methyl-1H-pyrazol-3-yl)amino]quinazolin-6-yl}oxy)-N-(2-pyrrolidin-1-ylethyl)nicotinamide Using 4-[(1-methyl-1H-pyrazol-3-yl)amino]quinazolin-6-ol and 5,6-dichloro-N-methyl-N-(2-pyrrolidin-1-ylethyl)nicotinamide, and in the same manner as in Example 65 or according to a method similar to it or according to a combination thereof with an ordinary method, the entitled compound (99 mg) was obtained as a pale yellow amorphous solid.

The analytical data of the entitled compound are shown below.

$^1$H-NMR (DMSO-$d_6$) δ: 1.62 (4H, brs), 2.27 (2H, brs), 2.49-2.58 (4H, m), 2.98 (3H, s), 3.31-3.54 (2H, m), 3.80 (3H, s), 6.81 (1H, d, J=2.0 Hz), 7.66 (1H, d, J=2.4 Hz), 7.74 (1H, dd, J=2.4, 9.3 Hz), 7.84 (1H, d, J=8.8 Hz), 8.15 (1H, d, J=2.0 Hz), 8.21 (1H, d, J=2.0 Hz), 8.54 (1H, d, J=2.4 Hz), 8.60 (1H, s), 10.34 (1H, s).

ESI-MS (m/e): 507 [M+H]$^+$

Preparation of 5,6-dichloro-N-methyl-N-(2-pyrrolidin-1-ylethyl)nicotinamide

Thionyl chloride (6 ml) was added to 5,6-dichloronicotinic acid (600 mg, 3.13 mmol), and stirred under a nitrogen atmosphere at 90° C. for 30 minutes. The reaction solution was concentrated under reduced pressure, and with cooling with ice, triethylamine (1.31 ml, 9.38 mmol) and N-methyl-2-pyrrolidin-1-ylethanamine (481 mg, 3.75 mmol) were added to a tetrahydrofuran solution (4 ml) of the obtained residue, and stirred at room temperature for 3 minutes. Saturated saline water and chloroform were added to the reaction solution, the organic layer was dried over anhydrous sodium sulfate, and concentrated under reduced pressure. The obtained residue was purified by amine-type silica gel column chromatography (Biotage NH, hexane:ethyl acetate=4:1 to 1:1) to obtain 5,6-dichloro-N-methyl-N-(2-pyrrolidin-1-ylethyl)nicotinamide 967 mg) as an orange oil.

Example 67

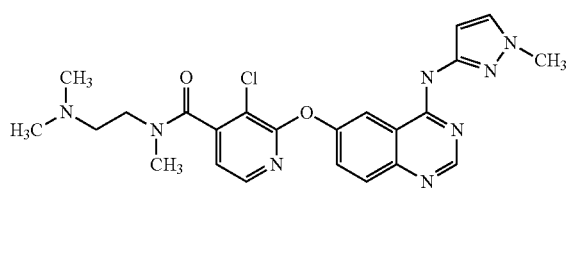

Preparation of 3-chloro-N-[2-(dimethylamino)ethyl]-N-methyl-2-({4-[(1-methyl-1H-pyrazol-3-yl)amino]quinazolin-6-yl}oxy)isonicotinamide 3-Chloro-N-[2-(dimethylamino)ethyl]-2-fluoro-N-methylisonicotinamide (116 mg, 0.45 mmol) and potassium tert-butoxide (70 mg, 0.62 mmol) were added to an N,N-dimethylacetamide solution (1 ml) of 4-[(1-methyl-1H-pyrazol-3-yl)amino]quinazolin-6-ol (650 mg, 0.25 mmol), and stirred under a nitrogen atmosphere at 80° C. for 2 hours. The reaction solution was cooled to room temperature, water was added, and extracted with chloroform. The organic layer was washed with water, dried over anhydrous sodium sulfate, and concentrated under reduced pressure. The obtained residue was purified by amine-type silica gel column chromatography (Biotage NH, hexane:ethyl acetate to chloroform:methanol=1:3 to 100:2) to obtain the entitled compound (101 mg, yield: 84%) as a pale yellow amorphous solid.

The analytical data of the entitled compound are shown below.

$^1$H-NMR (DMSO-$d_6$) δ: 2.04-2.23 (6H, m), 2.33-2.51 (2H, m), 2.89-3.06 (3H, m), 3.19-3.63 (2H, m), 3.80 (3H, s), 6.81 (1H, d, J=2.4 Hz), 7.18-7.24 (1H, m), 7.66 (1H, d, J=2.0 Hz), 7.72-7.76 (1H, m), 7.83-7.86 (1H, m), 8.13-8.15 (1H, m), 8.53-8.55 (1H, m), 8.60 (1H, brs), 10.34 (1H, d, J=3.4 Hz).

ESI-MS (m/e): 481 [M+H]$^+$

Preparation of 3-chloro-N-[2-(dimethylamino)ethyl]-2-fluoro-N-methylisonicotinamide N,N,N'-trimethylethane-1,2-diamine (0.92 ml, 6.84 mmol), 1-hydroxybenzotriazole monohydrate (1.05 g, 6.84 mmol) and 1-ethyl-3-(3-dimethylaminopropyl)carbodiimide hydrochloride (1.31 g, 6.84 mmol) were added to a chloroform solution (15 ml) of 3-chloro-2-fluoroisonicotinic acid (1.0 g, 5.70 mmol), and stirred under a nitrogen atmosphere at room temperature for 30 minutes. Saturated saline water was added to the reaction solution, and extracted with chloroform/methanol (9:1). The organic layer was dried over anhydrous sodium sulfate, and concentrated under reduced pressure. The obtained residue was purified by amine-type silica gel column chromatography (Biotage NH, hexane:ethyl acetate=4:1 to 1:1) to obtain 3-chloro-N-[2-(dimethylamino)ethyl]-2-fluoro-N-methylisonicotinamide (1.27 g, yield: 85%) as a colorless oil.

Example 68

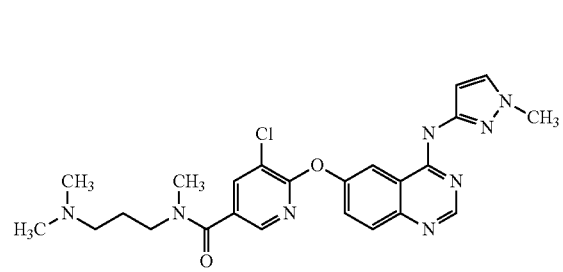

Preparation of 5-chloro-N-[3-(dimethylamino)propyl]-N-methyl-6-({4-[(1-methyl-1H-pyrazol-3-yl)amino]quinazolin-6-yl}oxy)nicotinamide Using 4-[(1-methyl-1H-pyrazol-3-yl)amino]quinazolin-6-ol and 5,6-dichloro-N-[3-(dimethylamino)propyl]-N-methylnicotinamide, and in the same manner as in Example 65 or according to a method similar to it or according to a combination thereof with an ordinary method, the entitled compound (58 mg) was obtained as a yellow amorphous solid.

The analytical data of the entitled compound are shown below.

$^1$H-NMR (DMSO-$d_6$) δ: 1.64-1.70 (2H, m), 2.04-2.10 (6H, m), 2.37-2.53 (2H, m), 2.96-2.98 (3H, m), 3.30-3.43 (2H, m), 3.80 (3H, s), 6.81 (1H, d, J=2.4 Hz), 7.66 (1H, d, J=2.0 Hz), 7.73 (1H, d, J=11.2 Hz), 7.85 (1H, d, J=8.8 Hz), 8.16 (1H, d, J=15.1 Hz), 8.23 (1H, s), 8.54 (1H, d, J=2.4 Hz), 8.60 (1H, s), 10.34 (1H, s).

ESI-MS (m/e): 495 [M+H]$^+$

Preparation of 5,6-dichloro-N-[3-(dimethylamino)propyl]-N-methylnicotinamide

Thionyl chloride (15 ml) was added to 5,6-dichloronicotinic acid (2.0 g, 10.4 mmol), and stirred under a nitrogen atmosphere at 90° C. for 30 minutes. The reaction solution was concentrated under reduced pressure, and with cooling with ice, triethylamine (4.36 ml, 31.3 mmol) and N,N,N'-trimethylpropane-1,3-diamine (2.39 ml, 15.6 mmol) were added to a tetrahydrofuran solution (30 ml) of the obtained residue, and stirred at room temperature for 3 minutes. Saturated saline water was added to the reaction solution, and extracted with chloroform. The organic layer was dried over anhydrous sodium sulfate, and concentrated under reduced pressure. The obtained residue was purified by amine-type silica gel column chromatography (Biotage NH, hexane:ethyl acetate=4:1 to 1:1) to obtain 5,6-dichloro-N-[3-(dimethylamino)propyl]-N-methylnicotinamide (3.21 mg) as an orange oil.

Example 69

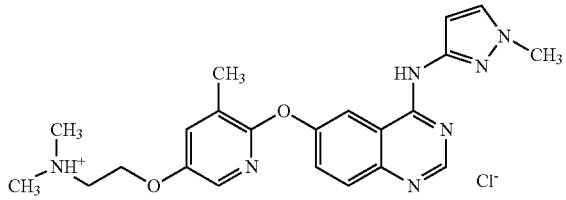

Preparation of N,N-dimethyl-2-{[5-methyl-6-({4-[(1-methyl-1H-pyrazol-3-yl)amino]quinazolin-6-yl}oxy)pyridin-3-yl]oxy}ethanamine hydrochloride The title compound (138 mg) was obtained as a pale yellow solid by the methods as in Examples 32 and 34, methods equivalent thereto or combinations of these with usual methods, using 4-[(1-methyl-1H-pyrazol-3-yl)amino]quinazolin-6-ol, 5-(2,2-diethoxyethoxy)-2-fluoro-3-methylpyridine and a 2M dimethylamine-tetrahydrofuran solution.

The analytical data of the title compound are shown below.
$^1$H-NMR(DMSO-$d_6$)δ:2.34(3H,s),2.81(6H,s),3.48(2H,t,J=4.9 Hz),3.79(3H,s),4.40(2H,t,J=5.1 Hz),6.78(1H,s),7.54-7.66(3H,m),7.74-7.81(2H,m),8.31(1H,s),8.55(1H,s),10.30 (1H,br s).
ESI-MS(m/e):420[M+H]$^+$

Example 70

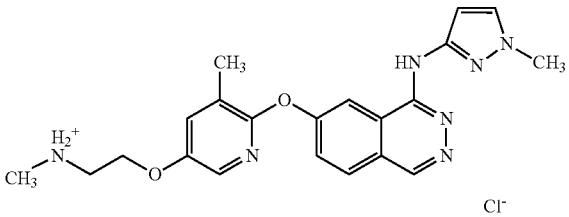

Preparation of N-methyl-2-{[5-methyl-6-({4-[(1-methyl-1H-pyrazol-3-yl)amino]quinazolin-6-yl}oxy)pyridin-3-yl]oxy}ethanamine hydrochloride The title compound (95 mg) was obtained as a pale yellow solid by the methods as in Examples 32 and 34, methods equivalent thereto or combinations of these with usual methods, using 4-[(1-methyl-1H-pyrazol-3-yl)amino]quinazolin-6-ol, 5-(2,2-diethoxyethoxy)-2-fluoro-3-methylpyridine and a 2M methylamine-tetrahydrofuran solution.

The analytical data of the title compound are shown below.
$^1$H-NMR(DMSO-$d_6$)δ:2.34(3H,s),2.60(3H,s),3.29-3.33 (2H,m),3.81(3H,s),4.30(2H,t,J=5.0 Hz),6.77(1H,s),7.55(1H, dd,J=2.9,0.7 Hz),7.64-7.69(2H,m),7.76(1H,d,J=2.4 Hz), 7.84(1H,d,J=9.0 Hz),8.37(1H,s),8.67(1H,s),9.10(2H,s), 10.79(1H, br s).
ESI-MS(m/e):406[M+H]$^+$

Example 71

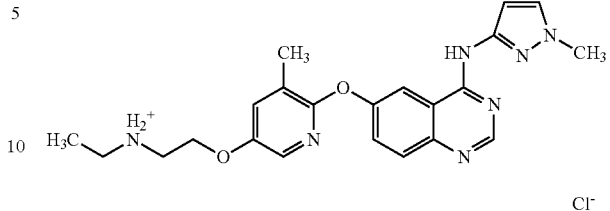

Preparation of N-ethyl-2-{[5-methyl-6-({4-[(1-methyl-1H-pyrazol-3-yl)amino]quinazolin-6-yl}oxy)pyridin-3-yl]oxy}ethanamine hydrochloride The title compound (117 mg) was obtained as a pale yellow solid by the methods as in Examples 32 and 34, methods equivalent thereto or combinations of these with usual methods, using 4-[(1-methyl-1H-pyrazol-3-yl)amino]quinazolin-6-ol, 5-(2,2-diethoxyethoxy)-2-fluoro-3-methylpyridine and a 2M ethylamine-tetrahydrofuran solution.

The analytical data of the title compound are shown below.
$^1$H-NMR(DMSO-$d_6$)δ:1.22(3H,t,J=7.2 Hz),2.35(3H,s), 2.98-3.05(2H,m),3.30-3.34(2H,m),3.80(3H,s),4.30(2H,t, J=5.0 Hz),6.77(1H,s),7.55(1H,dd,J=3.0,0.6 Hz),7.61(1H,dd, J=8.8, 2.2 Hz),7.66(1H,d,J=2.2 Hz),7.76(1H,d,J=2.7 Hz), 7.80(1H,d,J=9.0 Hz),8.34(1H,s),8.60(1H,s),9.04 (2H,s), 10.52(1H,br s).
ESI-MS(m/e):420[M+H]$^+$

Example 72

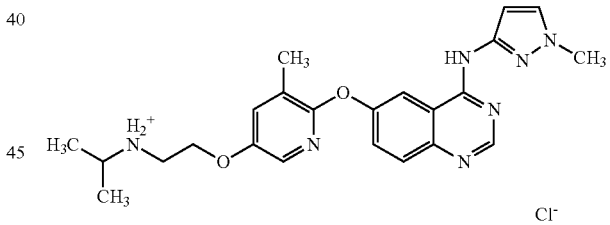

Preparation of N-(2-{[5-methyl-6-({4-[(1-methyl-1H-pyrazol-3-yl)amino]quinazolin-6-yl}oxy)pyridin-3-yl]oxy}ethyl)propan-2-amine hydrochloride The title compound (130 mg) was obtained as a pale yellow solid by the methods as in Examples 32 and 34, methods equivalent thereto or combinations of these with usual methods, using 4-[(1-methyl-1H-pyrazol-3-yl)amino]quinazolin-6-ol, 5-(2,2-diethoxyethoxy)-2-fluoro-3-methylpyridine and isopropylamine.

The analytical data of the title compound are shown below.
$^1$H-NMR(DMSO-$d_6$)δ:1.27(6H,d,J=6.4 Hz),2.35(3H,s), 2.98-3.06(1H,m),3.58-3.66(2H,m),3.80(3H,s),4.29-4.37 (2H,m),6.76(1H,s),7.56-7.67(3H,m),7.76-7.82(2H,m),8.34 (1H,s),8.61(1H,s),9.11(2H,s),10.58(1H,br s)
ESI-MS(m/e):434[M+H]$^+$.

Example 73

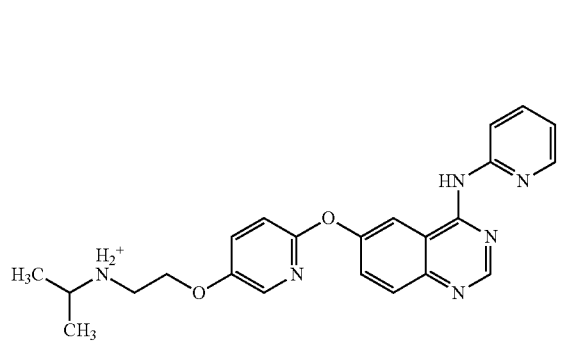

Preparation of N-{2-[(6-{[4-(pyridin-2-ylamino)quinazolin-6-yl]oxy}pyridin-3-yl)oxy]ethyl}propan-2-amine hydrochloride The title compound (16 mg) was obtained as a white solid by the methods as in Examples 32 and 34, methods equivalent thereto or combinations of these with usual methods, using 4-(pyridin-2-ylamino)quinazolin-6-ol, 5-(2,2-diethoxy-ethoxy)-2-fluoropyridine and isopropylamine.

The analytical data of the title compound are shown below.

$^1$H-NMR(DMSO-$d_6$)δ:1.27(6H,d,J=6.6 Hz),3.30-3.41(3H,m),4.35(2H,t,J=5.1 Hz),7.14-7.19(2H,m),7.63-7.68(2H,m),7.84-7.88(2H,m),7.96(1H,d,J=2.7 Hz),8.28(0.5H,brs),8.40(1H,dd,J=4.7,1.2 Hz),8.47(1H,s),8.66(1H,s), 9.15(1.5H, brs).

ESI-MS(m/e):417[M+H]$^+$

Preparation of 4-(pyridin-2-ylamino)quinazolin-6-ol

To a solution of pyridin-2-amine (101 mg, 1.08 mmol) and 4-chloroquinazolin-6-ylacetate (200 mg, 0.90 mmol) in toluene (4 ml), tris(dibenzylideneacetone)dipalladium (0) (82.0 mg, 0.090 mmol), (±)BINAP (112.0 mg, 0.180 mmol) and cesium carbonate (585 mg, 1.80 mmol) were added, and the mixture was stirred under nitrogen atmosphere at 120° C. for 2 hours. The reaction liquid was filtered, followed by vacuum concentration of the filtrate. The residue was suspended in water and then extracted with chloroform, and thereafter the combined organic layers were washed with water and a saturated saline solution and dried over anhydrous sodium sulfate, followed by being concentrated under reduced pressure. The resultant residue was dissolved in ammonia water (1 ml) and methanol (4 ml), and the solution was stirred at 50° C. for 2 hours. The reaction solution was cooled to room temperature and then concentrated under reduced pressure, the resultant residue was suspended in ether, and the precipitate was obtained through filtration, washed with ether and then dried to give 4-(pyridin-2-ylamino)quinazolin-6-ol (138 mg, yield: 64%) as a brown solid.

Example 74

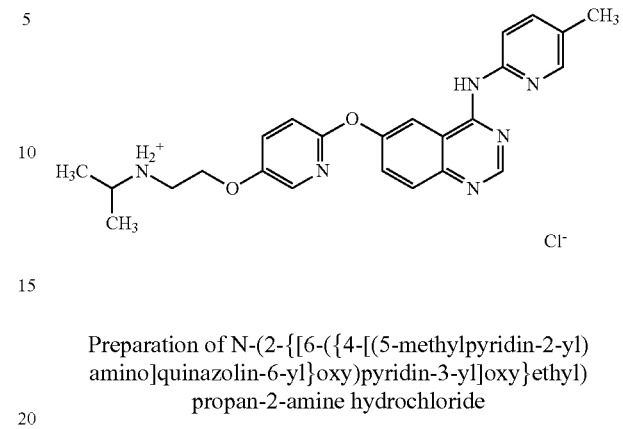

Preparation of N-(2-{[6-({4-[(5-methylpyridin-2-yl)amino]quinazolin-6-yl}oxy)pyridin-3-yl]oxy}ethyl)propan-2-amine hydrochloride The title compound (12 mg) was obtained as a white solid by the methods as in Examples 32 and 34, methods equivalent thereto or combinations of these with usual methods, using 4-[(5-methylpyridin-2-yl)amino]quinazolin-6-ol, 5-(2,2-diethoxyethoxy)-2-fluoropyridine and isopropylamine The analytical data of the title compound are shown below.

$^1$H-NMR(DMSO-$d_6$)δ:1.28(6H,d,J=6.6 Hz),2.34(3H, s), 3.30-3.44(3H, m),4.36(2H,t,J=4.9 Hz),7.22(1H,d,J=8.6 Hz), 7.67(1H,dd,J=9.0,3.1 Hz),7.79-8.08(5H,m),8.32(1H,s),8.55 (0.5H,brs),8.81(1H,s),9.19(1.5H,brs).

ESI-MS(m/e):431[M+H]$^+$

Preparation of 4-[(5-methylpyridin-2-yl)amino]quinazolin-6-ol

Using 5-methylpyridin-2-amine (97 mg, 0.90 mmol) and 4-chloroquinazolin-6-ylacetate (200 mg, 0.90 mmol), 4-[(5-methylpyridin-2-yl)amino]quinazolin-6-ol (163 mg, yield: 69%) was obtained as a brown solid by the method as in Example 73.

Example 75

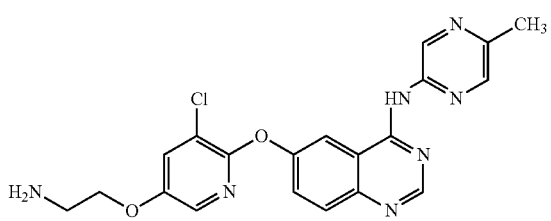 [SMILES: Cc1cnc(Nc2ncnc3ccc(Oc4ncc(OCCN)cc4Cl)cc23)cn1]

Preparation of 6-{[5-(2-aminoethoxy)-3-chloropyridin-2-yl]oxy}-N-(5-methylpyrazin-2-yl)quinazolin-4-amine 1) Using 4-[(5-methylpyrazin-2-yl)amino]quinazolin-6-ol and 3-chloro-5-[2-(1,3-dioxolan-2-yl)ethoxy]-2-fluoropyridine, 5-chloro-6-({4-[(5-methylpyrazin-2-yl)amino]quinazolin-6-yl}oxy)pyridin-3-ol (194 mg) was obtained as a brown solid by the methods as in Example 6-2) and Example 6-3), methods equivalent thereto or combinations of these with usual methods.

2) To a solution of an alcohol compound (50 mg, 0.13 mmol), obtained in the above reaction, in tetrahydrofuran (2 ml), were added tert-butyl(2-hydroxyethyl)carbamate (42 mg, 0.26 mmol), triphenylphosphine (69 mg, 0.26 mmol) and diethyl azodicarboxylate (0.042 ml, 0.26 mmol), and the reaction liquid was stirred at room temperature for 18 hours. The reaction liquid was concentrated under reduced pressure, and the resultant residue was purified by silica gel column chromatography (chloroform:methanol=90:10) to give tert-butyl(2-{[5-chloro-6-({4-[(5-methylpyrazin-2-yl)amino]quinazolin-6-yl}oxy)pyridin-3-yl]oxy}ethyl)carbamate (67 mg, yield: 97%) as a pale yellow oily substance.

3) To a solution of the carbamate compound (67 mg, 0.13 mmol), obtained in the above reaction, in chloroform (1 ml), was added trifluoroacetate (0.5 ml), and the reaction liquid was stirred at room temperature for 2 hours. To the reaction liquid was added a saturated aqueous sodium bicarbonate solution, and the mixture was extracted with chloroform-methanol (5:1). The organic layer was washed with water and a saturated saline solution, dried over anhydrous sodium sulfate, and then concentrated under reduced pressure. The resultant residue was purified by thin layer silica gel chromatography based on amine (chloroform:methanol=97:3) to yield the title compound (24 mg) as a pale yellow solid.

The analytical data of the title compound are shown below.
$^1$H-NMR(DMSO-$d_6$)δ:2.48(3H, s),2.86(2H,t,J=5.6 Hz), 4.00(2H, t,J=5.6 Hz),7.70(1H,dd,J=9.0,2.7 Hz),7.84-7.91 (3H,m),8.31-8.40(2H,m),8.64(1H,s),9.35(1H, br s).
ESI-MS(m/e):424[M+H]$^+$ Example 76

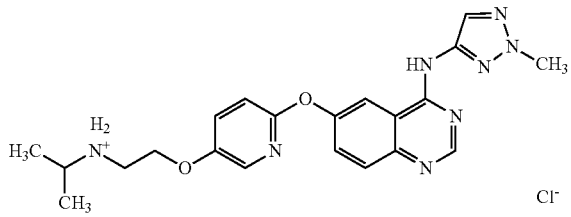

Preparation of N-(2-{[6-({4-[(2-methyl-2H-1,2,3-triazol-4-yl)amino]quinazolin-6-yl}oxy)pyridin-3-yl]oxy}ethyl)propan-2-amine hydrochloride The title compound (12 mg) was obtained as a white solid by the methods as in Examples 32 and 34, methods equivalent thereto or combinations of these with usual methods, using 4[(2-methyl-2H-1,2,3-triazol-4-yl)amino]quinazolin-6-ol, 5-(2,2-diethoxyethoxy)-2-fluoro-3-methylpyridine and isopropylamine.

The analytical data of the title compound are shown below.
$^1$H-NMR(CD$_3$OD)δ:1.16(3H,s),1.18(3H,s),2.91-2.98 (1H,m),3.05(2H,t,J=5.3 Hz),4.17(3H,s),4.19(2H,t,J=5.3 Hz),7.13(1H,d,J=8.9 Hz),7.60-7.62(1H,m),7.67(1H,d,J=8.9 Hz),7.88(1H,d,J=10.2 Hz),7.95(1H,d,J=3.1 Hz),8.12(1H,s), 8.27(1H,brs), 8.66(1H,brs).
ESI-MS(m/e):421[M+H]$^+$ Preparation of 4-[(2-methyl-2H-1,2,3-triazol-4-yl)amino]quinazolin-6-ol To 2-methyl-2H-1,2,3-triazol-4-amine hydrochloride (1.5 g, 11.2 mmol) and 4-chloroquinazolin-6-ylacetate (2.48 g, 11.2 mmol) was added phenol (3.15 g, 33.4 mmol), followed by stirring the mixture at 130° C. for 30 minutes. The reaction liquid was cooled to room temperature, methanol (0.5 ml) and ammonia water (1 ml) were then added, and the mixture was stirred overnight at room temperature. The resultant precipitate was obtained through filtration, washed with methanol-water (1:1), and then dried under reduced pressure to give 4-[(2-methyl-2H-1,2,3-triazol-4-yl)amino]quinazolin-6-ol (2.10 g, yield: 78%) as a gray solid.

Example 77

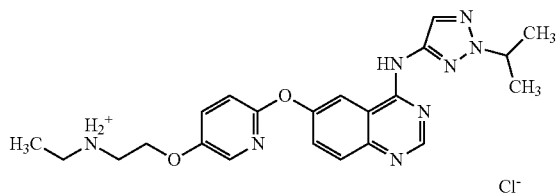

Preparation of N-ethyl-2-({6-[(4-{[2-(propan-2-yl)-2H-1,2,3-triazol-4-yl]amino}quinazolin-6-yl)oxy]pyridin-3-yl}oxy)ethanamine hydrochloride The title compound (34 mg) was obtained as a pale yellow solid by the methods as in Examples 32 and 34, methods equivalent thereto or combinations of these with usual methods, using 4-{[2-(propan-2-yl)-2H-1,2,3-triazol-4-yl]amino}quinazolin-6-ol, 5-(2,2-diethoxyethoxy)-2-fluoro-3-methylpyridine and 2M ethylamine-tetrahydrofuran solution.

The analytical data of the title compound are shown below.
$^1$H-NMR (CD$_3$OD)δ:1.42(3H,t,J=7.2 Hz),1.61(6H,d, J=6.6 Hz),3.23(2H,q,J=7.3 Hz),3.53(2H,t,J=5.0H z),4.40 (2H,t,J=5.0 Hz),4.80-4.87(1H,m),7.20(1H,d,J=9.0 Hz),7.70 (1H,dd,J=9.0,3.1 Hz),7.75(1H,dd,J=9.0,2.3 Hz),7.92(1H,d, J=9.0 Hz),8.01(1H,d,J=3.1 Hz),8.25(1H,d,J=2.3 Hz),8.31 (1H,brs),8.77(1H,brs).
ESI-MS(m/e):435[M+H]$^+$ Preparation of 4-{[2-(propan-2-yl)-2H-1,2,3-triazol-4-yl]amino}quinazolin-6-ol Using 2-(propan-2-yl)-2H-1,2,3-triazol-4-amine (1.15 g, 9.12 mmol) and 4-chloroquinazolin-6-ylacetate (2.0 g, 8.98 mmol), 4-{[2-(propan-2-yl)-2H-1,2,3-triazol-4-yl]

Example 78

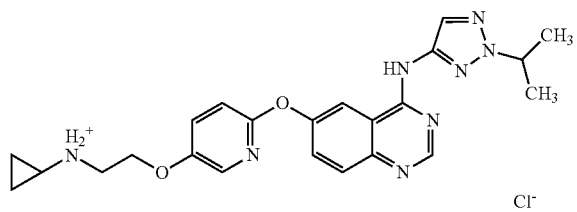

Preparation of N-[2-({6-[(4-{[2-(propan-2-yl)-2H-1,2,3-triazol-4-yl]amino}quinazolin-6-yl)oxy]pyridin-3-yl}oxy)ethyl]cyclopropane amine hydrochloride The title compound (73 mg) was obtained as a pale yellow solid by the methods as in Examples 32 and 34, methods equivalent thereto or combinations of these with usual methods, using 4-{[2-(propan-2-yl)-2H-1,2,3-triazol-4-yl]amino}quinazolin-6-ol, 5-(2,2-diethoxyethoxy)-2-fluoro-3-methylpyridine and cyclopropylamine.

The analytical data of the title compound are shown below.
$^1$H-NMR(CD$_3$OD)δ:0.48-0.52(1H,m),0.72-0.76(1H,m), 0.98-1.02(1H,m),1.61(6H,d,J=6.6 Hz),2.64-2.69(1H,m), 2.89-2.94(1H,m),3.65(2H,t,J=5.0 Hz),4.43(2H,t,J=5.0 Hz), 4.80-4.87(1H,m),7.20(1H,d,J=9.0 Hz),7.70(1H,dd,J=9.0,3.1 Hz),7.75(1H,dd,J=9.0,2.7 Hz),7.91(1H,d,J=9.0 Hz),8.01 (1H,d,J=2.7 Hz),8.25(1H,d,J=2.3 Hz),8.31(1H,s),8.77(1H, s).
ESI-MS (m/e):447[M+H]$^+$

Example 79

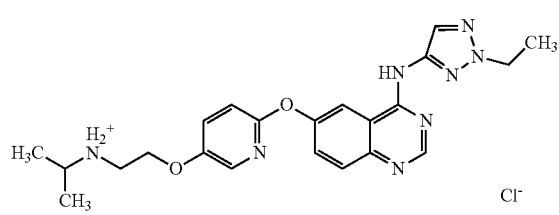

Preparation of N-(2-{[6-({4-[(2-ethyl-2H-1,2,3-triazol-4-yl)amino]quinazolin-6-yl})oxy)pyridin-3-yl]oxy}ethyl)propan-2-amine hydrochloride The title compound (124 mg) was obtained as a pale yellow solid by the methods as in Examples 32 and 34, methods equivalent thereto or combinations of these with usual methods, using 4-[(2-ethyl-2H-1,2,3-triazol-4-yl)amino]quinazolin-6-ol, 5-(2,2-diethoxyethoxy)-2-fluoro-3-methylpyridine and isopropylamine The analytical data of the title compound are shown below.
$^1$H-NMR(CD$_3$OD)δ:1.45(6H,d,J=6.6 Hz),1.55-1.59(3H, m),3.53-3.60(1H,m),3.54(2.0H,t,J=5.1 Hz),4.39-4.49(4H, m),7.18(1H,dd,J=9.1,3.9 Hz),7.67-7.72(2H,m),7.88(1H,t, J=9.1 Hz),8.00(1H,d,J=2.7 Hz),8.17-8.20(1H,m),8.27(1H,d, J=6.6 Hz),8.70(1H,d,J=7.8 Hz).
ESI-MS(m/e):435[M+H]$^+$ Preparation of 4-[(2-ethyl-2H-1,2,3-triazol-4-yl)amino]quinazolin-6-ol 1) To a solution of 4-nitro-2H-1,2,3-triazole (2.02 g, 17.7 mmol) in N,N-dimethylformamide (40 ml), sodium hydride (1.06 g, 26.6 mmol) was added at 0° C., and the mixture was stirred at room temperature for 10 minutes. To the reaction solution was added ethyl iodide (4.15 g, 26.6 mmol), followed by stirring the mixture overnight at room temperature. To the reaction solution was added a saturated aqueous sodium bicarbonate solution, the mixture was then extracted with ethyl acetate, and the combined organic layers were washed with water and a saturated saline solution, then dried over anhydrous sodium sulfate, and then concentrated under reduced pressure. The resultant residue was purified by silica gel column chromatography (Biotage, hexane:ethyl acetate=5:1 to 1:4) to give 2-ethyl-4-nitro-2H-1,2,3-triazole (1.35 g, yield: 53%) as a pale yellow oily substance.

2) To a solution of nitro intermediate (1.35 g, 9.46 mmol), obtained in the above reaction, in methanol (30 ml), was added palladium carbon (500 mg, 50% wet, 4.70 mmol), followed by overnight stirring the mixture under hydrogen atmosphere at room temperature under a pressure of one atmosphere. The reaction solution was filtered through Celite to remove palladium carbon, and the solvent was concentrated under reduced pressure to give 2-ethyl-2H-1,2,3-triazol-4-amine (979 mg, yield: 92%) as a red oily substance.

3) Using 2-ethyl-2H-1,2,3-triazol-4-amine (979 mg, 8.73 mmol) obtained in the above reaction and 4-chloroquinazolin-6-ylacetate (1.94 g, 8.73 mmol), 4-[(2-ethyl-2H-1,2,3-triazol-4-yl)amino]quinazolin-6-ol (1.52 g, yield: 68%) was obtained as a gray solid by the method as in Example 76.

Example 80

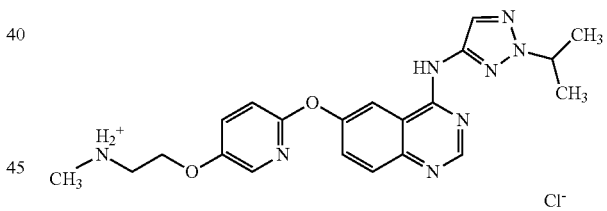

Preparation of N-methyl-2-({6-[(4-{[2-(propan-2-yl)-2H-1,2,3-triazol-4-yl]amino}quinazolin-6-yl)oxy]pyridin-3-yl}oxy)ethanamine hydrochloride The title compound (32 mg) was obtained as a pale yellow solid by the methods as in Examples 32 and 34, methods equivalent thereto or combinations of these with usual methods, using 4-{[2-(propan-2-yl)-2H-1,2,3-triazol-4-yl]amino}quinazolin-6-ol, 5-(2,2-diethoxyethoxy)-2-fluoro-3-methylpyridine and 2M methylamine-tetrahydrofuran solution.

The analytical data of the title compound are shown below.
$^1$H-NMR (CD$_3$OD)δ:1.60(6H,d,J=7.0 Hz),2.86(3H,s), 3.53(2H,t,J=4.9 Hz),4.40(2H,t,J=4.9 Hz),4.79-4.86(1H,m), 7.19(1H,d,J=9.0 Hz),7.68-7.73(2H,m),7.90(1H,d,J=9.0 Hz), 8.00(1H,d,J=3.1 Hz),8.22(1H,d,J=2.7 Hz),8.30(1H,brs),8.73 (1H, brs)
ESI-MS(m/e):421[M+H]$^+$.

Example 81

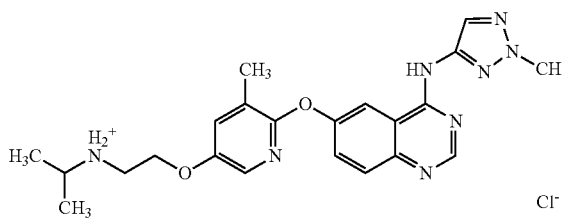

Preparation of N-(2-{[5-methyl-6-({4-[(2-methyl-2H-1,2,3-triazol-4-yl)amino]quinazolin-6-yl}oxy)pyridin-3-yl]oxy}ethyl)propan-2-amine hydrochloride The title compound (71 mg) was obtained as a pale yellow solid by the methods as in Examples 32 and 34, methods equivalent thereto or combinations of these with usual methods, using 4-[(2-methyl-2H-1,2,3-triazol-4-yl)amino]quinazolin-6-ol, 5-(2,2-diethoxyethoxy)-2-fluoro-3-methylpyridine and isopropylamine The analytical data of the title compound are shown below.
$^1$H-NMR(CD$_3$OD)δ:1.45(6H,d,J=6.6 Hz),2.44(3H,s),3.52-3.58(1H,m),3.53(2H,t,J=4.9 Hz),4.19(3H,s),4.40(2H,t,J=4.9 Hz),7.59(1H,d,J=2.7 Hz),7.77(1H,dd,J=9.0,2.3 Hz),7.82(1H,d,J=2.7 Hz),7.92(1H,dd,J=9.2,2.3 Hz),8.20(1H,s),8.29(1H,s),8.78(1H,s).
ESI-MS(m/e):435[M+H]$^+$

Example 82

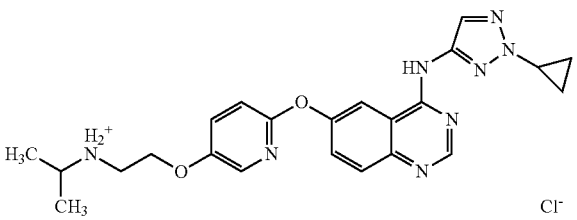

Preparation of N-(2-{[6-({4-[(2-cyclopropyl-2H-1,2,3-triazol-4-yl)amino]quinazolin-6-yl}oxy)pyridin-3-yl]oxy}ethyl)propan-2-amine hydrochloride The title compound (51 mg) was obtained as a pale yellow solid by the methods as in Examples 32 and 34, methods equivalent thereto or combinations of these with usual methods, using 4-[(2-cyclopropyl-2H-1,2,3-triazol-4-yl)amino]quinazolin-6-ol, 5-(2,2-diethoxyethoxy)-2-fluoro-3-methylpyridine and isopropylamine The analytical data of the title compound are shown below.
$^1$H-NMR(CD$_3$OD)δ:1.11-1.17(2H,m),1.30-1.35(2H,m),1.45(6H,d,J=6.6 Hz),3.51-3.58(3H,m),4.02-4.08(1H,m),4.40(2H,t,J=4.9 Hz),7.19(1H,d,J=9.0 Hz),7.68-7.74(2H,m),7.90(1H,d,J=8.2 Hz),8.00(1H,d,J=3.1 Hz),8.21(1H,t,J=2.0 Hz),8.28(1H,s),8.73(1H,s)
ESI-MS(m/e):447[M+H]$^+$.

Preparation of 4-[(2-cyclopropyl-2H-1,2,3-triazol-4-yl)amino]quinazolin-6-ol 1) To a solution of 4-nitro-2H-1,2,3-triazole (1.0 g, 8.77 mmol), cyclopropylboronic acid (1.51 g, 17.5 mmol), copper (II) acetate (1.59 g, 8.77 mmol) and N,N-dimethylpyridin-4-amine (3.21 g, 26.3 mmol) in toluene (20 ml) was added sodium 1,1,1,3,3,3-hexamethyldisilazan-2-id (14.6 ml, 0.6M toluene solution) under oxygen atmosphere, and the mixture was stirred at 95° C. for 2 days. The reaction solution was cooled to room temperature, water was then added, the mixture was extracted with chloroform, then dried over anhydrous sodium sulfate, and concentrated under reduced pressure. The resultant residue was purified by silica gel column chromatography (Biotage, hexane:ethyl acetate=5:1 to 3:1) to give 2-cyclopropyl-4-nitro-2H-1,2,3-triazole (249 mg, yield: 18%) as a yellow oily substance.

2) To a solution of nitro intermediate (249 mg, 1.62 mmol), obtained in the above reaction, in tetrahydrofuran (3 ml), were added methanol (1.5 ml), water (0.75 ml), aqueous saturated ammonium chloride solution (0.75 ml) and iron powder (451 mg, 8.08 mmol), and the mixture was stirred at 85° C. for 90 minutes. The reaction liquid was cooled and then filtered, the residue was washed with methanol, and the filtrate was then concentrated under reduced pressure. The resultant residue was suspended in a saturated aqueous sodium bicarbonate solution, then extracted with chloroform, dried over anhydrous sodium sulfate, and then concentrated under reduced pressure. To the resultant product were added 1N hydrochloric acid (1.62 ml, 1.62 mmol) and methanol (5 ml), and the mixture was concentrated under reduced pressure again to give 2-cyclopropyl-2H-1,2,3-triazol-4-amine hydrochloride (160 mg, yield: 62%) as a brown solid.

3) Using 2-cyclopropyl-2H-1,2,3-triazol-4-amine hydrochloride (160 mg, 1.00 mmol) obtained in the above reaction and 4-chloroquinazolin-6-ylacetate (230 mg, 1.03 mmol), 4[(2-cyclopropyl-2H-1,2,3-triazol-4-yl)amino]quinazolin-6-ol (149 mg, yield: 54%) was obtained as a light brown solid by the method as in Example 76.

Example 83

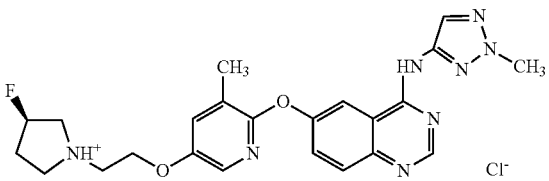 [SMILES: Cc1cc(OCC[NH+]2CC[C@@H](F)C2)cnc1Oc1ccc2ncnc(Nc3cnn(C)n3)c2c1 ; [Cl-]]

Preparation of (3R)-3-fluoro-1-(2-{[5-methyl-6-({4-[(2-methyl-2H-1,2,3-triazol-4-yl)amino]quinazolin-6-yl}oxy)pyridin-3-yl]oxy}ethyl)pyrrolidine hydrochloride The title compound (42 mg) was obtained as a pale yellow solid by the methods as in Examples 32 and 34, methods equivalent thereto or combinations of these with usual methods, using 4-[(2-methyl-2H-1,2,3-triazol-4-yl)amino]quinazolin-6-ol, 5-(2,2-diethoxyethoxy)-2-fluoro-3-methylpyridine and (3R)-3-fluoropyrrolidine.

The analytical data of the title compound are shown below.

$^1$H-NMR(CD$_3$OD)δ:2.44(3H,s),2.44-2.60(2H,m),3.67-3.99(6H,m),4.19(3H,s),4.48(2H,t,J=4.9 Hz),5.53(1H,d, J=53.2 Hz),7.62(1H,d,J=2.7 Hz),7.78(1H,dd, J=9.0,2.3 Hz), 7.83(1H,d,J=2.7 Hz),7.92(1H,d,J=9.0 Hz),8.21(1H,s),8.30 (1H,s),8.80(1H,s).

ESI-MS(m/e):465[M+H]$^+$

Example 84

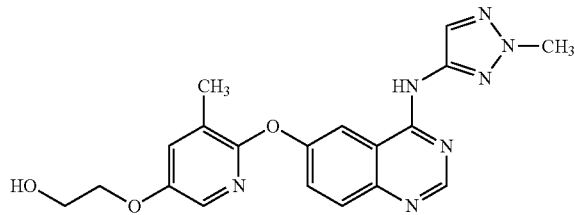 [SMILES: Cc1cc(OCCO)cnc1Oc1ccc2ncnc(Nc3cnn(C)n3)c2c1]

Preparation of 2-{[5-methyl-6-({4-[(2-methyl-2H-1, 2,3-triazol-4-yl)amino]quinazolin-6-yl}oxy)pyridin-3-yl]oxy}ethanol The title compound (258 mg) was obtained as a white solid by the methods as in Examples 1 and 49, methods equivalent thereto or combinations of these with usual methods, using 4-[(1-methyl-1H-pyrazol-3-yl)amino]quinazolin-6-ol and 5-(2,2-diethoxyethoxy)-2-fluoro-3-methylpyridine.

The analytical data of the title compound are shown below.

$^1$H-NMR(DMSO-d$_6$)δ:2.32(3H,s),3.70(2H,t,J=5.0 Hz), 4.02(2H,t,J=5.0 Hz),4.11(3H,s),4.89(1H,t,J=5.0 Hz),7.49 (1H, d,J=2.4 Hz),7.61(1H,dd,J=2.4,9.0 Hz),7.70(1H,d,J=2.4 Hz),7.82(1H,d,J=9.0 Hz),8.23(1H,s),8.28(1H,d,J=2.4 Hz), 8.64(1H,s),10.68(1H,brs).

ESI-MS(m/e):394[M+H]$^+$

INDUSTRIAL APPLICABILITY

Heteroaryloxyquinazoline derivatives of the formula (I) and their pharmaceutically-acceptable salts of the invention have an excellent effect of glucokinase activation, and are useful in the field of medicines for remedy and/or prevention of diabetes, complications of diabetes or obesity.

What is claimed is:

1. A compound represented by a formula (I):

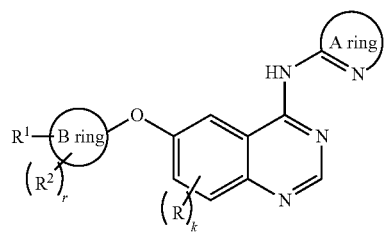

wherein the A ring represents a pyrazinyl group, which may have one or two substituent groups selected from the group consisting of lower alkyl, lower alkoxy, halogen, hydroxy, and C$_{3-7}$ cycloalkyl, wherein the alkyl substituent group may have 1-3 identical or different substituent groups selected from the group consisting of lower alkoxy groups, halogen atoms and hydroxy groups;

the B ring represents a 5- or 6-membered heteroaryl group having 1-3 identical or different hetero atoms selected from the group consisting of nitrogen, sulfur and oxygen atoms;

R represents a substituent group selected from the group consisting of lower alkyl, lower alkoxy, halogen, hydroxy and lower alkyl having 1-3 identical or different substituent groups selected from the group consisting of: lower alkoxy groups, halogen atoms or hydroxy groups;

k represents an integer of from 0 to 3;

R$^1$ denotes a group represented by a formula (II-1), (II-2), (II-3) or II-4):

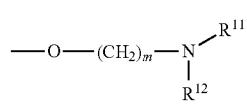

wherein R$^{11}$ and R$^{12}$ each independently represent hydrogen, lower alkyl or C$_{3-7}$ cycloalkyl, or R$^{11}$ and R$^{12}$, together with the nitrogen atom to which they are bound, constitute a 4- to 7-membered nitrogen-containing aliphatic ring (which may be substituted with 1-3 identical or different halogen atoms), or any carbon atom of (CH$_2$)$_m$, together with R$^{11}$ or R$^{12}$, may constitute a 4- to 7-membered nitrogen-containing aliphatic ring;

any carbon atom in (CH$_2$)$_m$ may be substituted with a lower alkyl group;

the nitrogen atom to which R$^{11}$ and R$^{12}$ are bound may form N-oxide; and m represents an integer of from 2 to 6, a group represented by a formula (II-2)

wherein:

R$^{13}$ represents lower alkoxy, hydroxy or carboxyl;

n represents an integer of from 1 to 6;

upon R$^{13}$ being lower alkoxy, the lower alkoxy, together with any carbon atom of (CH$_2$)$_n$, may form a 5- to 7-membered aliphatic rings; and any carbon atom in (CH$_2$)$_n$ may be substituted with a lower alkyl group, a group represented by a formula (II-3)

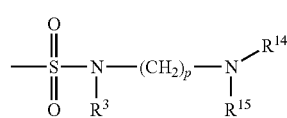

wherein R$^{14}$ and R$^{15}$ are synonymous with the above R$^{11}$ and R$^{12}$;

p represents an integer of from 2 to 6; and

R$^3$ represents a hydrogen atom or a lower alkyl group, or a group represented by a formula (II-4)

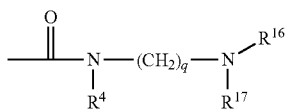

wherein:
$R^{16}$ and $R^{17}$ are synonymous with the above $R^{11}$ and $R^{12}$;
q represents an integer of from 2 to 6; and
$R^4$ represents a hydrogen atom or a lower alkyl group,
$R^2$ is a group selected from the group consisting of: lower alkyl, lower alkoxy, halogen, hydroxy, cyano, carboxyl, alkoxycarbonyl, N-alkylcarbamoyl, N,N-dialkylcarbamoyl, lower alkylsulfonyl and lower alkyl having 1-3 identical or different substituents independently selected from lower alkoxy groups, halogen atoms, hydroxy groups, cyano groups, carboxyl groups, alkoxycarbonyl groups, N-alkylcarbamoyl groups, N,N-dialkylcarbamoyl groups or lower alkylsulfonyl groups, and
r represents an integer of from 0 to 3,
or a pharmaceutically acceptable salt thereof.

2. The compound according to claim 1 wherein the B ring is selected from the group consisting of pyridinyl, pyrazinyl, pyrimidinyl, pyridazinyl, thiazolyl, thiadiazolyl, imidazolyl and isoxazolyl groups, or a pharmaceutically acceptable salt thereof.

3. The compound according to claim 1 wherein $R^1$ is a group represented by the formula (II-1) or (II-2), or a pharmaceutically acceptable salt thereof.

4. The compound according to claim 1 wherein $R^1$ is a group represented by the formula (II-1), or a pharmaceutically acceptable salt thereof.

5. The compound according to claim 1 wherein $R^1$ is a group represented by the formula (II-2), or a pharmaceutically acceptable salt thereof.

6. The compound according to claim 1 wherein $R^1$ is a group represented by the formula (II-3), or a pharmaceutically acceptable salt thereof.

7. The compound according to claim 1 wherein $R^1$ is a group represented by the formula (II-4), or a pharmaceutically acceptable salt thereof.

8. The compound according to claim 4, wherein one of $R^{11}$ and $R^{12}$ is a hydrogen atom; and the other is a lower alkyl or $C_{3-7}$ cycloalkyl group, or a pharmaceutically acceptable salt thereof.

9. The compound according to claim 4, wherein $R^{11}$ and $R^{12}$ each independently are lower alkyl or $C_{3-7}$ cycloalkyl groups, or a pharmaceutically acceptable salt thereof.

10. The compound according to claim 4, wherein $R^{11}$ and $R^{12}$ represent a 4- to 7-membered nitrogen-containing aliphatic rings formed by $R^{11}$ and $R^{12}$ together with the nitrogen atom to which they are bound, wherein the 4- to 7-membered nitrogen-containing aliphatic rings may be substituted with 1-3 identical or different halogen atoms, or a pharmaceutically acceptable salt thereof.

11. The compound according to claim 4, wherein $R^{11}$ and $R^{12}$ represent a 4- to 7-membered nitrogen-containing aliphatic ring formed by either $R^{11}$ or $R^{12}$ together with any carbon atom of $(CH_2)_m$, and further wherein any carbon atom in $(CH_2)_m$ may be substituted with a lower alkyl group, or a pharmaceutically acceptable salt thereof.

12. The compound according to claim 1, wherein the compound represented by the formula (I) is:
6-({3-chloro-5-[2-(methylamino)ethoxy]pyridin-2-yl}oxy)-N-(5-methylpyrazin-2-yl)quinazolin-4-amine,
6-({5-[2-(dimethylamino)ethoxy]-3-methylpyridin-2-yl}oxy)-N-(5-methylpyrazin-2-yl)quinazolin-4-amine,
6-({3-fluoro-5-[2-(methylamino)ethoxy]pyridin-2-yl}oxy)-N-(5-methylpyrazin-2-yl)quinazolin-4-amine,
6-({3-fluoro-5-[2-(isopropylamino)ethoxy]pyridin-2-yl}oxy)-N-(5-methylpyrazin-2-yl)quinazolin-4-amine,
6-({3-methyl-5-[2-(methylamino)ethoxy]pyridin-2-yl}oxy)-N-(5-methylpyrazin-2-yl)quinazolin-4-amine,
6-{[3-chloro-5-(3-pyrrolidin-1-ylpropoxy)pyridin-2-yl]oxy}-N-(5-methylpyrazin-2-yl)quinazolin-4-amine,
or a pharmaceutically acceptable salt thereof.

13. A pharmaceutical composition comprising the compound according to claim 1 or the pharmaceutically acceptable salt thereof in combination with a pharmaceutically acceptable carrier.

14. The compound according to claim 1 wherein the B ring is a pyridinyl group, or a pharmaceutically acceptable salt thereof.

15. A compound which is 6-({3-chloro-5-[2-(methylamino)ethoxy]pyridin-2-yl}oxy)-N-(5-methylpyrazin-2-yl)quinazolin-4-amine, or a pharmaceutically acceptable salt thereof.

16. A compound which is 6-({3-chloro-5-[2-(methylamino)ethoxy]pyridin-2-yl}oxy)-N-(5 -methylpyrazin-2-yl)quinazolin-4-amine.

* * * * *